US010875883B2

(12) United States Patent
Liu et al.

(10) Patent No.: US 10,875,883 B2
(45) Date of Patent: Dec. 29, 2020

(54) METHOD FOR SYNTHESIZING NOVEL CHIRAL LIGAND, METAL CHELATE, A VARIETY OF NON-NATURAL AMINO ACIDS, MARAVIROC AND KEY INTERMEDIATE THEREOF

(71) Applicant: SHANGHAI INSTITUTE OF MATERIA MEDICA, CHINESE ACADEMY OF SCIENCES, Shanghai (CN)

(72) Inventors: Hong Liu, Shanghai (CN); Jiang Wang, Shanghai (CN); Shengbin Zhou, Shanghai (CN); Panfeng Peng, Shanghai (CN); Yong Nian, Shanghai (CN); Shuni Wang, Shanghai (CN); Shuangjie Shu, Shanghai (CN); Hao Shen, Shanghai (CN); Hualiang Jiang, Shanghai (CN); Kaixian Chen, Shanghai (CN)

(73) Assignee: SHANGHAI INSTITUTE OF MATERIA MEDICA, CHINESE ACADEMY OF SCIENCES, Shanghai (CN)

( * ) Notice: Subject to any disclaimer, the term of this patent is extended or adjusted under 35 U.S.C. 154(b) by 0 days.

(21) Appl. No.: 16/337,338

(22) PCT Filed: Sep. 19, 2017

(86) PCT No.: PCT/CN2017/102327
§ 371 (c)(1),
(2) Date: Mar. 27, 2019

(87) PCT Pub. No.: WO2018/059279
PCT Pub. Date: Apr. 5, 2018

(65) Prior Publication Data
US 2019/0233456 A1 Aug. 1, 2019

(30) Foreign Application Priority Data
Sep. 29, 2016 (CN) .......................... 2016 1 0871043

(51) Int. Cl.
C07D 498/04 (2006.01)
C07D 231/56 (2006.01)
C07F 15/04 (2006.01)
C07D 207/16 (2006.01)
C07D 401/04 (2006.01)
C07D 409/12 (2006.01)
C07C 227/34 (2006.01)
C07C 229/34 (2006.01)

(52) U.S. Cl.
CPC .......... *C07F 15/045* (2013.01); *C07C 227/34* (2013.01); *C07C 229/34* (2013.01); *C07D 207/16* (2013.01); *C07D 401/04* (2013.01); *C07D 409/12* (2013.01); *C07F 15/04* (2013.01); *Y02P 20/55* (2015.11)

(58) Field of Classification Search
CPC ............................. C07F 15/04; C07D 207/16
USPC .......................................................... 514/230
See application file for complete search history.

(56) References Cited

U.S. PATENT DOCUMENTS

2008/0161264 A1* 7/2008 Tung ................... C07D 451/04
514/50

FOREIGN PATENT DOCUMENTS

CN 1437599 8/2003
WO 2012029067 * 3/2012

OTHER PUBLICATIONS

Wang, Shuni et al., Chemical resolution of C, N-unprotected a-substituted beta-amino acids using stable and recyclable proline-derived chiral ligands; Journal of Organic Chemistry (2018), 83 (17), 9870-9878.*
International Search Report corresponding to PCT/CN2017/102327 dated Dec. 22, 2017; 3 pages.
Haycock-Lewandowski, S. J. et al., "Development of a Bulk Enabling Route to Maraviroc (UK-427,857), a CCR-5 Receptor Antagonist," *Organic Process Research & Development* (2008); vol. 12, No. 6, pp. 1094-1103.
Zhao, G. et al., "Asymmetric Synthesis of Maraviroc (UK-427,857)," *Adv. Synth. Catal.* (2010); vol. 352, pp. 2291-2298.
Extended European Search Report corresponding to EP 17854729.5 dated Feb. 28, 2020; 10 pages.
Sorochinsky, Alexander E. et al., "Chemical deracemization and (S) to ® interconversion to some fluorine-containing α-amino acids," *Journal of Fluorine Chemistry* (2013; available online Mar. 5, 2013) 152:114-118.

(Continued)

*Primary Examiner* — Mark L Shibuya
*Assistant Examiner* — Ebenezer O Sackey
(74) *Attorney, Agent, or Firm* — Mintz Levin Cohn Ferris Glovsky and Popeo PC

(57) ABSTRACT

Disclosed is a method for synthesizing a novel chiral ligand, a metal chelate, a variety of non-natural amino acids, Maraviroc and a key intermediate thereof. In the invention, (R)-2-methyl proline is selected and used as a starting raw material, (S)-β³-amino acid is obtained by asymmetric resolution induced by using a nickel chelate, and Maraviroc is synthesized by using (S)-3-amino-3-phenylpropionic acid as a key intermediate with a high yield and the ee value reaching 98.2% or more. The method of the present invention has widely available materials, mild synthetic process conditions, is easy to control, and produces a product of a high optical purity.

4 Claims, No Drawings

(56) References Cited

OTHER PUBLICATIONS

Sorochinsky, Alexander E. et al., "Asymmetric synthesis of α-amino acids via homologation of Ni(II) complexes of glycine Schiff bases; Part 1: alkyl halide alkylations," *Amino Acids* (2013; published online Jul. 6, 2013) 45:691-718.

Zhou, Shengbin et al., "Chemical Kinetic Resolution of Unprotected β-Amino Acids Using Recyclable Chiral Ligands," *Angew. Chem. Int. Ed.* (2014; published online Jun. 10, 2014) 53:7883-7886.

\* cited by examiner

METHOD FOR SYNTHESIZING NOVEL CHIRAL LIGAND, METAL CHELATE, A VARIETY OF NON-NATURAL AMINO ACIDS, MARAVIROC AND KEY INTERMEDIATE THEREOF

TECHNICAL FIELD

The invention relates to the field of medicine technology, in particular to a method for synthesizing a novel chiral ligand, metal chelate, various unnatural amino acids, Maraviroc and key intermediates thereof.

BACKGROUND ART 4,4-difluoro-N-[(1S)-3-[exo-3-(3-isopropyl-5-methyl-4H-1,2,4-triazol-4-yl)-8-azabicyclo[3.2.1]octan-8-yl]-1-phenylpropyl]cyclohexane-1-carboxamide, also known as Maraviroc, is a novel anti-HIV medicament developed by Pfizer Inc and approved by US FDA in August 2007. It is the first CC-chemokine receptor 5 (CCR5) antagonist drug for the treatment of HIV and often used in a monomeric form. Maraviroc can bind to the CCR5 receptor on the cell surface, block CCR5 tropic HIV-1 into the cell and inhibit HIV infection, so it can significantly hinder and delay the occurrence and development of AIDS.

The construction of chiral amino acids is the main point of the synthetic route during the preparation of the Maraviroc.

The literature (Organic Process Research & Development 2008, 12, 1094-1103) obtains racemic beta amino acid by the condensation of benzaldehyde, ammonium acetate and malonic acid, which is esterified to give the corresponding amino acid methyl ester, which is then subjected to L-(+)-tartaric acid resolution to give the tartrate of the key intermediate methyl (S)-3-amino-3-phenylpropionate. The overall yield of the reaction route is only 10%, and the ee value of the final product after two recrystallizations is greater than 95%. The chemical reaction route is as follows.

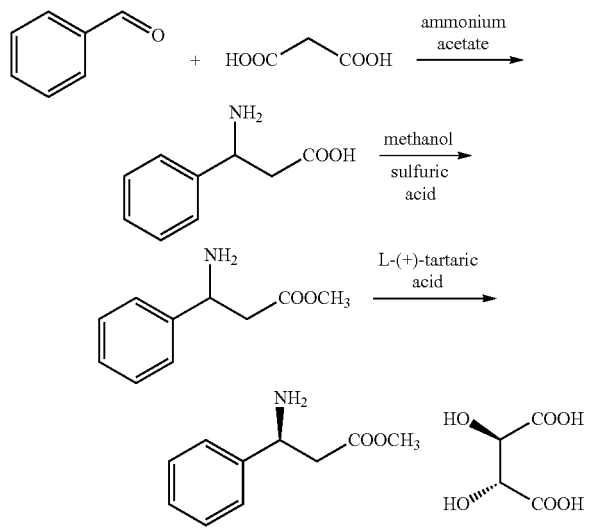

The method uses tartaric acid for resolution, which results in low total reaction yield, poor optical purity, low ee value and greatly increased cost. And the reaction uses concentrated sulfuric acid and generates a large amount of acidic wastewater, which is not conducive to environmental protection and has a large operational hazard.

Therefore, there is still a need in the art to develop a novel method for the synthesis of Maraviro Maraviroc and key intermediates thereof.

In addition, nickel chelate-induced asymmetric synthesis of non-natural chiral amino acid is a research hotspot of non-natural chiral amino acid asymmetric synthesis methods in recent years, but no better synthesis methods have been developed for asymmetric resolution methods for non-natural α-substituted-β amino acids. In the existing chiral ligands, substituted proline is used as the chiral control moiety. Although the resolution of non-natural alpha amino acids and non-natural beta-substituted-beta amino acids can be achieved, there is a possibility of self-racemization of the chiral center of proline. Therefore, it is urgent to develop a novel chiral ligand to solve the problem of self-racemization and apply the novel chiral ligand to the asymmetric resolution of non-natural chiral α-substituted-β amino acids.

SUMMARY OF THE INVENTION

The object of the present invention is to provide a method for synthesizing a novel chiral ligand, metal chelate, various unnatural amino acids, Maraviroc and key intermediates thereof, to improve optical purity and yield and to save synthesis cost.

The first aspect of the present invention provides a synthesis method for a novel quaternary carbon chiral ligand, comprising the step of synthesizing a compound of formula VI,

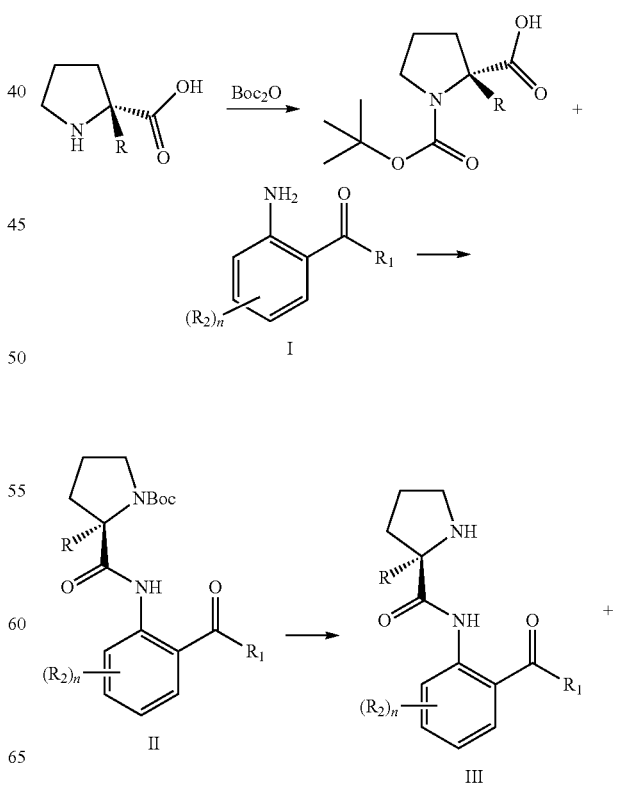

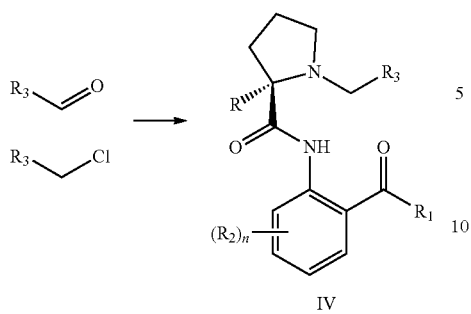

IV wherein n is an integer from 1 to 4;

R is selected from the group consisting of C1-C4 alkyl, C1-C4 haloalkyl and unsubstituted or substituted phenyl, wherein the substituted phenyl means that the phenyl has 1-5 substituents, and each substituent is independently selected from the group consisting of amino, halogen, hydroxyl, C1-C4 alkyl and C1-C4 haloalkyl;

$R_1$ is selected from the group consisting of H, C1-C4 alkyl, C1-C4 haloalkyl and unsubstituted or substituted phenyl, wherein the substituted phenyl means that the phenyl has 1-5 substituents, and each substituent is independently selected from the group consisting of amino, halogen, hydroxyl, C1-C4 alkyl and C1-C4 haloalkyl;

$R_2$ is selected from the group consisting of H, halogen, amino, hydroxyl, C1-C4 alkyl and C1-C4 haloalkyl;

$R_3$ is selected from the group consisting of H, C1-C4 alkyl, C1-C4 haloalkyl, unsubstituted or substituted phenyl and —(C1-C4 alkylene)-(unsubstituted or substituted phenyl); wherein the substituted phenyl means that the phenyl has 1-5 substituents, and each substituent is independently selected from the group consisting of amino, halogen, hydroxyl, C1-C4 alkyl and C1-C4 haloalkyl.

The second aspect of the present invention provides a novel resolution method for an alpha amino acid, an alpha substituted beta amino acid and a beta substituted beta amino acid, comprising the step of the hydrolysis of a compound of formula VI to obtain the alpha amino acid, the alpha substituted beta amino acid and the beta substituted beta amino acid of formula VII,

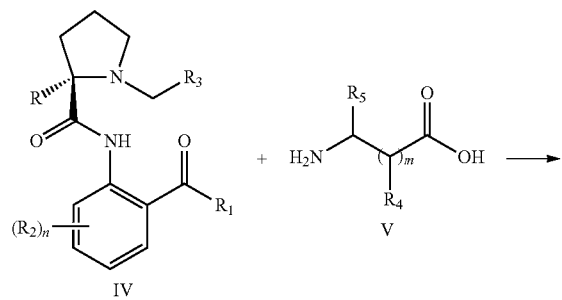

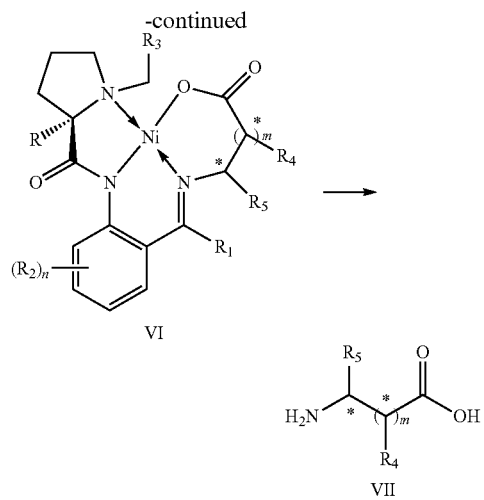

wherein n is an integer from 1 to 4, m is an integer from 0 to 1;

R is selected from the group consisting of C1-C4 alkyl, C1-C4 haloalkyl and unsubstituted or substituted phenyl, wherein the substituted phenyl means that the phenyl has 1-5 substituents, and each substituent is independently selected from the group consisting of amino, halogen, hydroxyl, C1-C4 alkyl and C1-C4 haloalkyl;

$R_1$ is selected from the group consisting of H, C1-C4 alkyl, C1-C4 haloalkyl and unsubstituted or substituted phenyl, wherein the substituted phenyl means that the phenyl has 1-5 substituents, and each substituent is independently selected from the group consisting of amino, halogen, hydroxyl, C1-C4 alkyl and C1-C4 haloalkyl;

$R_2$ is selected from the group consisting of H, halogen, amino, hydroxyl, C1-C4 alkyl and C1-C4 haloalkyl;

$R_3$ is selected from the group consisting of H, C1-C4 alkyl, C1-C4 haloalkyl, unsubstituted or substituted phenyl and —(C1-C4 alkylene)-(unsubstituted or substituted phenyl); wherein the substituted phenyl means that the phenyl has 1-5 substituents, and each substituent is independently selected from the group consisting of amino, halogen, hydroxyl, C1-C4 alkyl and C1-C4 haloalkyl;

$R_4$ is selected from the group consisting of H, unsubstituted or substituted C6-C10 aryl, unsubstituted or substituted C3-C6 heteroaryl and unsubstituted or substituted C3-C6 cycloalkyl, wherein the "substituted" means that there are 1-5 substituents, and each substituent is independently selected from the group consisting of amino, halogen, hydroxyl, nitro, cyano, C1-C4 alkyl, C1-C4 alkoxy and C1-C4 haloalkyl.

$R_5$ is selected from the group consisting of H, unsubstituted or substituted C6-C10 aryl, unsubstituted or substituted C3-C6 heteroaryl and unsubstituted or substituted C3-C6 cycloalkyl, wherein the "substituted" means that there are 1-5 substituents, and each substituent is independently selected from the group consisting of amino, halogen, hydroxyl, nitro, cyano, C1-C4 alkyl, C1-C4 alkoxy and C1-C4 haloalkyl.

* is a chiral center and contains various configurations, S configuration or R configuration.

In another preferred embodiment, the compound of formula VI is synthesized by the following step:

reacting a compound of formula IV with an unnatural amino acid of formula V under the action of a nickel salt to form the compound of formula VI,

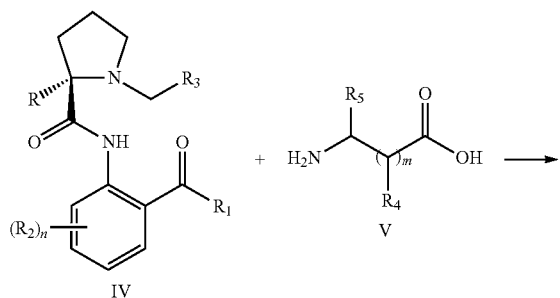

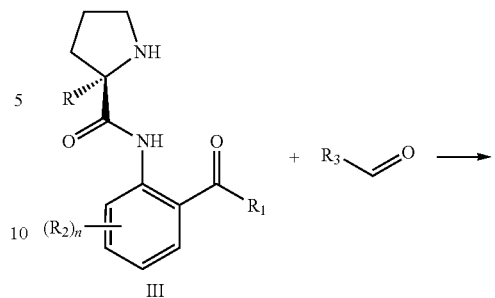

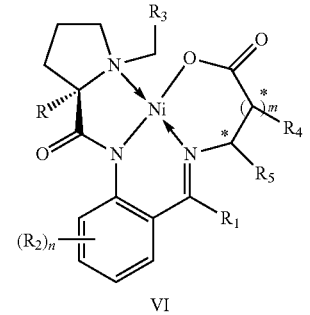

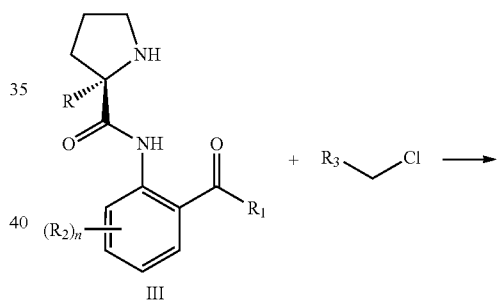

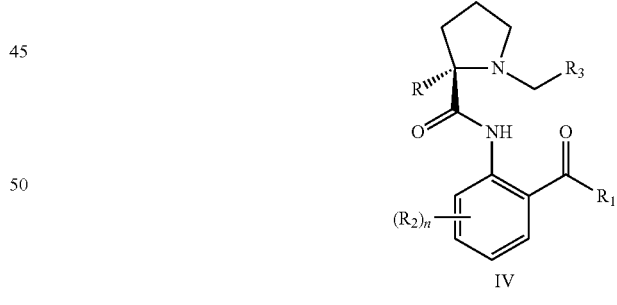

wherein n, m, R, $R_1$, $R_2$, $R_3$, $R_4$ and $R_5$ are as defined above.

In another preferred embodiment, the compound of formula V is a variety of non-natural alpha amino acids, alpha substituted beta amino acids, and beta substituted beta amino acids, such as alanine, phenylalanine, phenylalanine, 3-methoxyphenylalanine, 3-methylphenylalanine, 4-fluorophenylalanine, 3-methoxyphenylglycine, 3-bromophenylglycine, 2-amino-3-(3,5-diiodo-4-hydroxyphenyl)propionic acid, 2-amino-3-(naphth-1-yl)propionic acid, 2-amino-3-(benzothiophen-3-yl)propionic acid, 2-amino-3-(thiophen-3-yl)propionic acid, 2-amino-2-cyclobutylacetic acid, 2-amino-4,4,4-trifluorobutyric acid, 2-aminovaleric acid, 2-amino-3-methylbutyric acid, 2-amino-4-methylthiobutyric acid, 2-amino-3-(1H-indenyl)propionic acid, 2-amino-5-methyl-4-hexenoic acid, 2-aminoglutaric acid, 2,5-diamino-5-pentanone acid, homocysteine, 3-amino-2-benzylpropionic acid, 3-amino-2-(4-fluorobenzyl)propionic acid, 3-amino-2-(4-methoxybenzyl)propionic acid, 3-amino-2-methylpropionic acid, 2-(aminomethyl)-4-methylpentanoic acid, 3-amino-2-cyclohexylpropionic acid, 3-amino-2-phenylpropionic acid, 3-amino-2-(4-chlorophenyl)propionic acid, 3-amino-2-(4-methoxyphenyl)propionic acid, 3-amino-2-(naphth-1-yl)propionic acid 3-amino-propionic acid, 3-amino-3-phenylpropionic acid, 3-amino-3-(4-methyl)phenylpropionic acid, 3-amino-3-(3-methyl)phenylpropionic acid, 3-amino-3-(2-methyl)phenylpropionic acid, 3-amino-3-(2-fluoro)phenylpropionic acid, 3-amino-3-(4-chloro)phenylpropionic acid, 3-amino-3-(3,4-dimethoxy)phenylpropionic acid, 3-amino-3-(4-methoxy)phenylpropionic acid, 3-amino-3-(3-methoxy)phenylpropionic acid, 3-amino-3-(pyridin-4-yl)propionic acid, 3-amino-3-(thiophen-2-yl)propionic acid, 3-amino-3-cyclohexylpropionic acid, 3-amino-3-(naphthyl-2-yl)propionic acid or 3-amino-3-(2,4,5-trifluoro)phenylpropionic acid.

In another preferred embodiment, the compound of formula IV is synthesized by the following steps:

a compound of formula III and $R_3CHO$ are subjected to a reduction reaction to form the compound of formula IV, wherein n, R, $R_1$, $R_2$ and $R_3$ are as defined above.

In another preferred embodiment, the compound of formula IV is synthesized by the following steps:

a compound of formula III and $R_3CH_2Cl$ are subjected to a substitution reaction to form the compound of formula IV, wherein n, R, $R_1$, $R_2$ and $R_3$ are as defined above.

In another preferred embodiment, the compound of formula III is synthesized by the following steps:

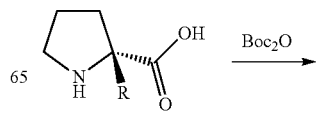

-continued

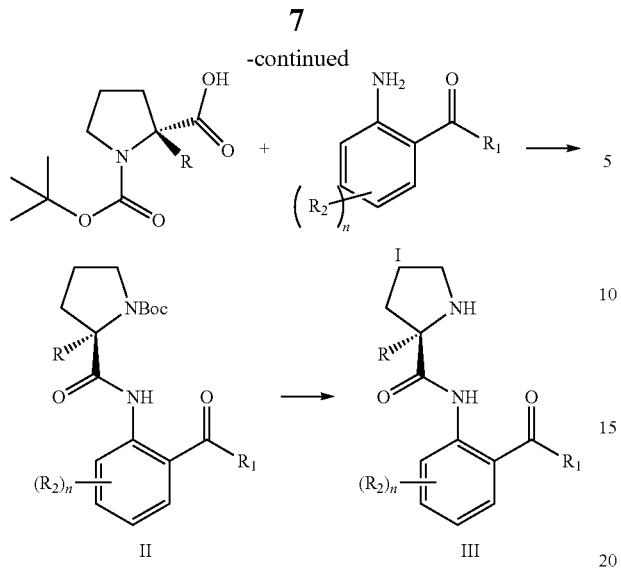

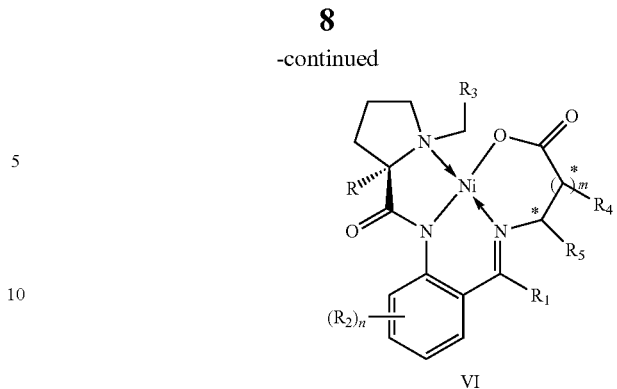

(i) reacting (R)-2-substituted proline with di-tert-butyl dicarbonate to form (R)-1-(tert-butoxycarbonyl)-2-methyl-proline;

(ii) subjecting (R)-1-(tert-butoxycarbonyl)-2-substituted proline to a condensation reaction with a compound of formula I to obtain a compound of formula II;

(iii) removing tert-butoxycarbonyl from the compound of formula II to obtain the compound of formula III, wherein n, R, $R_1$ and $R_2$ are as defined above.

In another preferred embodiment, $R_4$ is phenyl.

The third aspect of the present invention provides a Maraviroc intermediate having a structure of formula VI:

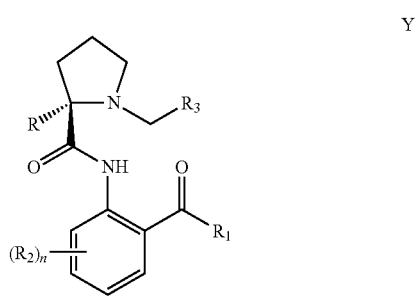

wherein n, m, $R_1$, $R_2$, $R_3$, $R_4$ and $R_5$ are as defined above.

In another preferred embodiment, the synthesis method comprises the following step:

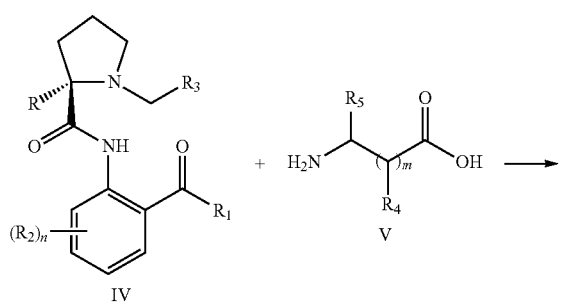

reacting a compound of formula IV with a non-natural amino acid of formula V under the action of a nickel salt to form the compound of VI, wherein n, m, $R_1$, $R_2$, $R_3$, $R_4$ and $R_5$ are as defined above.

The fourth aspect of the present invention provides a novel chiral ligand having a structure of formula Y:

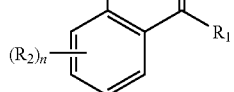

wherein n, R, $R_1$, $R_2$ and $R_3$ are as defined above.

The fifth aspect of the present invention provides a method for synthesizing Maraviroc, comprising the step of synthesizing a Maraviroc intermediate, wherein the Maraviroc intermediate is:

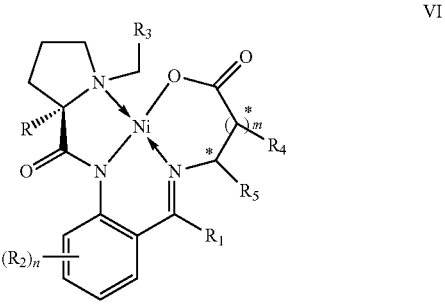

the step of synthesizing the Maraviroc intermediate is as defined above.

wherein n, $R_1$, $R_2$ and $R_3$ are as defined above, and $R_4$ is phenyl.

The sixth aspect of the present invention provides a method of synthesizing a plurality of unnatural amino acids, comprising the following steps:

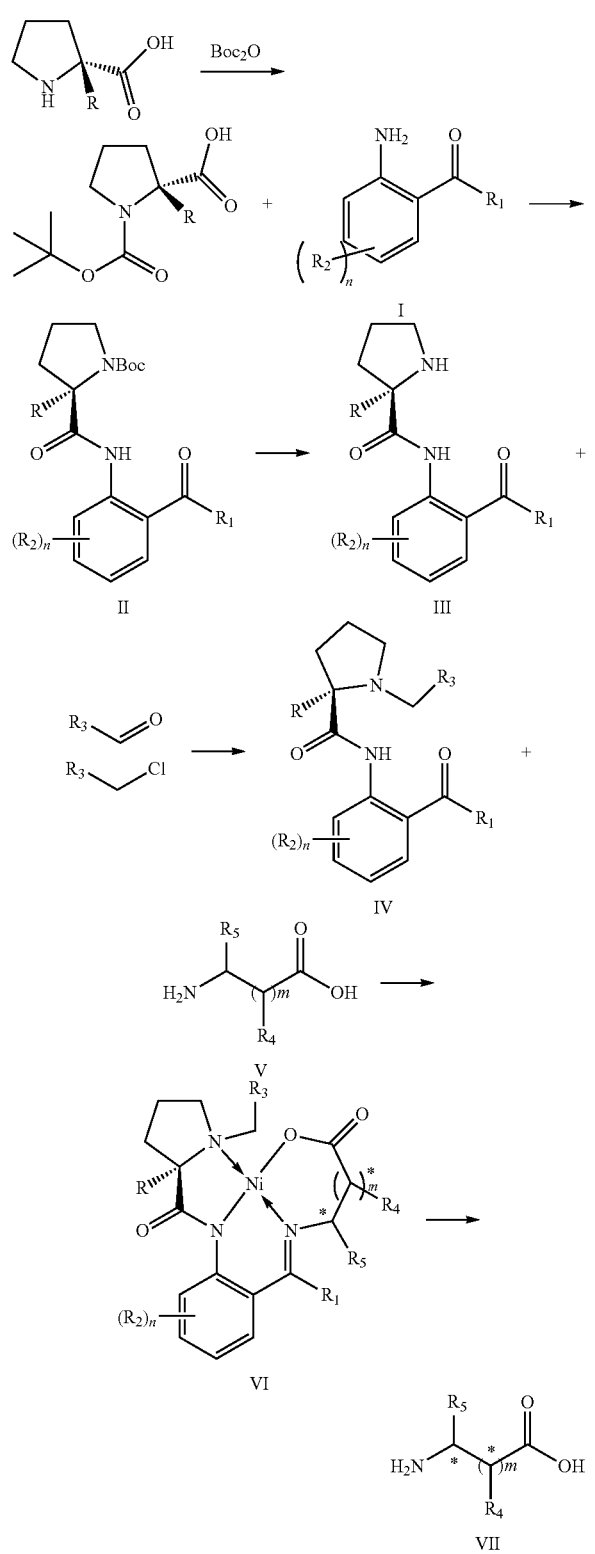

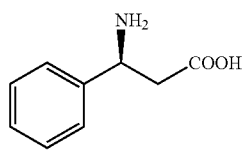 [SMILES: N[C@@H](CC(=O)O)c1ccccc1]

(i) reacting (R)-2-substituted proline with di-tert-butyl dicarbonate to form (R)-1-(tert-butoxycarbonyl)-2-methylproline;

(ii) subjecting (R)-1-(tert-butoxycarbonyl)-2-substituted proline to a condensation reaction with a compound of formula I to obtain a compound of formula II;

(iii) removing tert-butoxycarbonyl from the compound of formula II to obtain a compound of formula III;

(iv) subjecting the compound of formula III to a reductive amination reaction with $R_3CHO$ or $R_3CH_2Cl$ to obtain a compound of formula IV;

(v) reacting the compound of formula IV with a non-natural amino acid of formula V under the action of a nickel salt to form a compound of VI;

(vi) hydrolyzing the compound of VI to form a compound of VII, wherein n, m, R, $R_1$, $R_2$, $R_3$, $R_4$ and $R_5$ are as defined above.

In another preferred embodiment, $R_4$ is phenyl.

The seventh aspect of the present invention provides a method for synthesizing a key intermediate of Maraviroc, wherein the key intermediate of Maraviroc is:

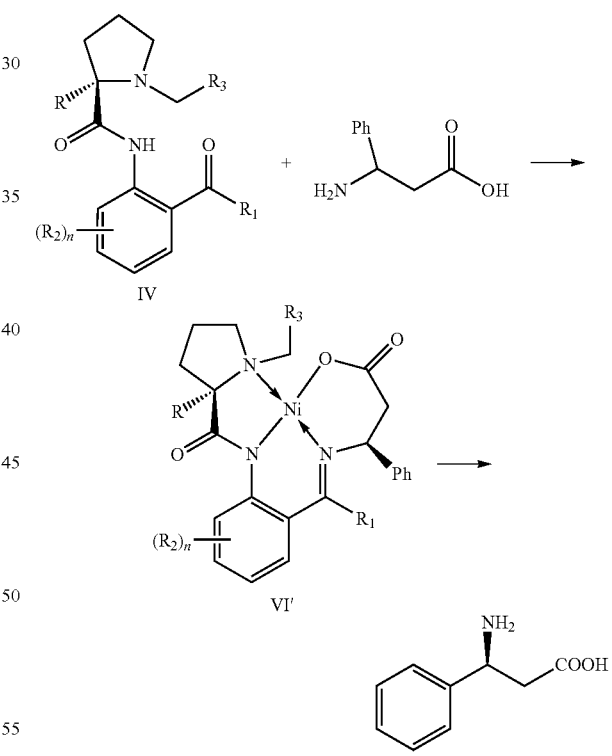

and the synthesis method includes the following steps:

(i) reacting the compound IV with 3-amino-3-phenylpropionic acid under the action of a nickel salt to obtain a compound of formula VI';

(ii) hydrolyzing the compound of formula VI' to obtain a compound of formula VII, wherein n, R, $R_1$, $R_2$ and $R_3$ are as defined above.

The eighth aspect of the present invention provides a method for synthesizing Maraviroc, comprising the step of synthesizing a key intermediate of Maraviroc, wherein the key intermediate of Maraviroc is:

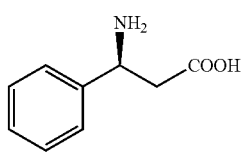 [SMILES: N[C@@H](CC(=O)O)c1ccccc1]

and the step of synthesizing the key intermediate of Maraviroc is as described in the fifth aspect.

The ninth aspect of the present invention provides a method for synthesizing Maraviroc, and the method further comprises the following steps:

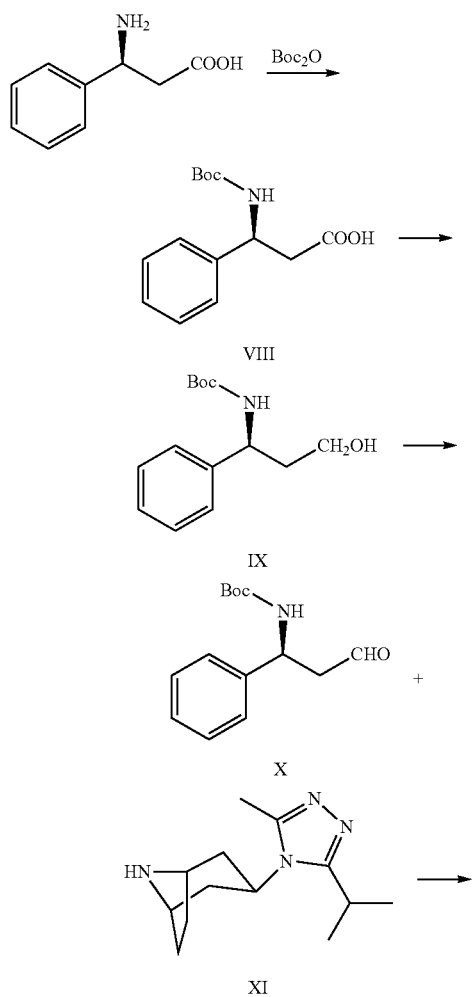

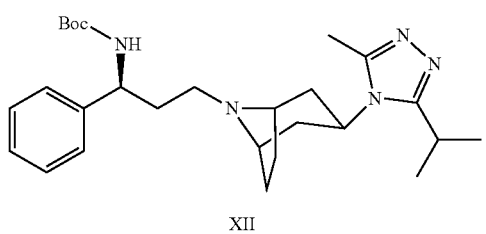

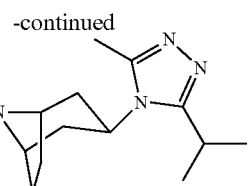

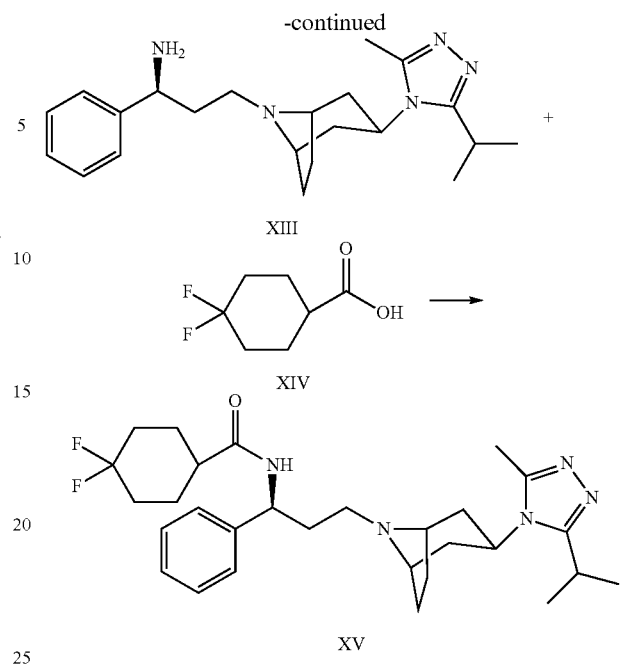

(i) reacting (S)-β³-phenylalanine with di-tert-butyl dicarbonate to obtain a compound of formula VIII;

(ii) subjecting the compound of formula VIII to a reduction reaction to obtain a compound of formula IX;

(iii) subjecting the compound of formula IX to an oxidation reaction to obtain a compound of formula X;

(iv) subjecting the compound of formula X to a reductive amination reaction with a compound of formula XI to obtain a compound of formula XII;

(v) removing tert-butoxycarbonyl from the compound of formula XII to obtain a compound of formula XIII;

(vi) subjecting the compound of formula XIII to a condensation reaction with a compound of formula XIV to obtain Maraviroc having formula XV.

The present invention adopts asymmetric resolution method of metal nickel chelate, and can efficiently, rapidly and highly stereoselectively prepare non-natural chiral amino acids, key intermediates of Maraviroc to realize the synthesis of Maraviroc and intermediates thereof, effectively shortens the synthetic route, improves the synthesis efficiency, and ensures the stereoselectivity of the final product, Maraviroc. It is an efficient and rapid synthesis method for Maraviroc and key intermediates thereof.

It is to be understood that within the scope of the present invention, above various technical features of the present invention and the various technical features specifically described hereinafter (as in the embodiments) may be combined with each other to form a novel or preferred technical solution. Due to space limitations, they will not be repeated herein.

DETAILED DESCRIPTION OF THE INVENTION

Based on the extensive and intensive studies, the inventors have developed for the first time a novel synthesis method for (S)-β3-amino acid, Maraviroc and key intermediates thereof. The invention adopts (R)-2-methylproline as a starting material, uses a nickel chelate to induce asymmetric resolution to obtain (S)-β³-amino acid, and uses (S)-3-amino-3-phenylpropionic acid as a key intermediate and raw material to synthesize Maraviroc, and the yield is high, and the ee value is above 98.2%. On the basis of this, the present invention has been completed.

Intermediate

An intermediate is a product formed during the production of a desired product. In the present invention, a plurality of intermediates are obtained, and the structures are respectively shown in formula VI and formula Y:

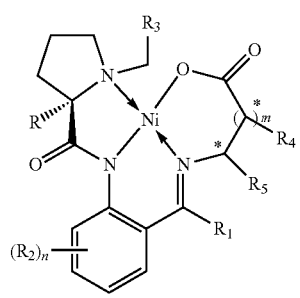

VI

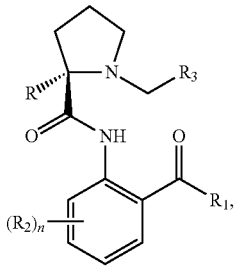

Y wherein n is an integer from 1 to 4, m is an integer from 0 to 1;

R is selected from the group consisting of C1-C4 alkyl, C1-C4 haloalkyl and unsubstituted or substituted phenyl, wherein the substituted phenyl means that the phenyl has 1-5 substituents, and each substituent is independently selected from the group consisting of amino, halogen, hydroxyl, C1-C4 alkyl and C1-C4 haloalkyl;

$R_1$ is selected from the group consisting of H, C1-C4 alkyl, C1-C4 haloalkyl and unsubstituted or substituted phenyl, wherein the substituted phenyl means that the phenyl has 1-5 substituents, and each substituent is independently selected from the group consisting of amino, halogen, hydroxyl, C1-C4 alkyl and C1-C4 haloalkyl;

$R_2$ is selected from the group consisting of H, halogen, amino, hydroxyl, C1-C4 alkyl and C1-C4 haloalkyl;

$R_3$ is selected from the group consisting of H, C1-C4 alkyl, C1-C4 haloalkyl, unsubstituted or substituted phenyl and —(C1-C4 alkylene)-(unsubstituted or substituted phenyl); wherein the substituted phenyl means that the phenyl has 1-5 substituents, and each substituent is independently selected from the group consisting of amino, halogen, hydroxyl, C1-C4 alkyl and C1-C4 haloalkyl;

$R_4$ is selected from the group consisting of H, unsubstituted or substituted C6-C10 aryl, unsubstituted or substituted C3-C6 heteroaryl and unsubstituted or substituted C3-C6 cycloalkyl, wherein the "substituted" means that there are 1-5 substituents, and each substituent is independently selected from the group consisting of amino, halogen, hydroxyl, nitro, cyano, C1-C4 alkyl, C1-C4 alkoxy and C1-C4 haloalkyl.

$R_5$ is selected from the group consisting of H, unsubstituted or substituted C6-C10 aryl, unsubstituted or substituted C3-C6 heteroaryl and unsubstituted or substituted C3-C6 cycloalkyl, wherein the "substituted" means that there are 1-5 substituents, and each substituent is independently selected from the group consisting of amino, halogen, hydroxyl, nitro, cyano, C1-C4 alkyl, C1-C4 alkoxy and C1-C4 haloalkyl.

In another preferred embodiment, n is 1, 2 or 3.

In another preferred embodiment, R is selected from the group consisting of methyl, trifluoromethyl, ethyl, propyl, difluoromethyl, dichloromethyl, trichloromethyl, benzyl, cyano, F, Cl, Br and I.

In another preferred embodiment, $R_1$ is selected from the group consisting of methyl, trifluoromethyl, ethyl, propyl, difluoromethyl, dichloromethyl and trichloromethyl.

In another preferred embodiment, $R_2$ is selected from the group consisting of H, F, Cl, Br, I, trifluoromethyl, methyl, ethyl, propyl, difluoromethyl, dichloromethyl and trichloromethyl.

In another preferred embodiment, $R_3$ is methyl, ethyl, phenyl, $C_6H_5CH_2$—, $C_6H_5CH_2CH_2$—, $C_6H_3Cl_2CH_2$—, or $C_6H_3Cl_2CH_2CH_2$—.

In another preferred embodiment, $R_4$ is phenyl, pyridyl, naphthyl, thienyl, methoxy phenyl or halophenyl.

In another preferred embodiment, the compound of formula Y is a compound of formula II, a compound of formula III or a compound of formula IV:

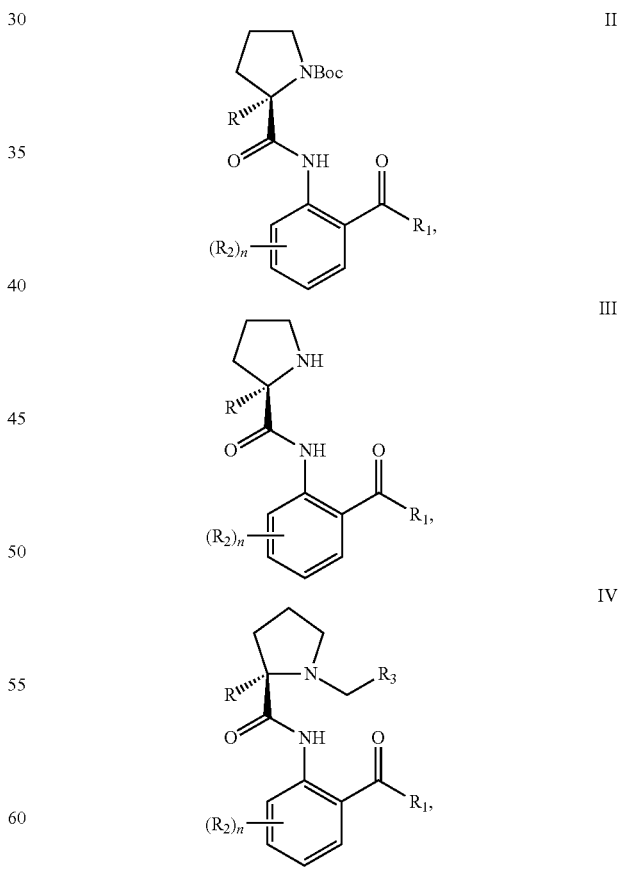

wherein n, $R_1$, $R_2$ and $R_3$ are as defined above.

Synthesis Method

In the present invention, the compound of formula II is synthesized by the following steps:

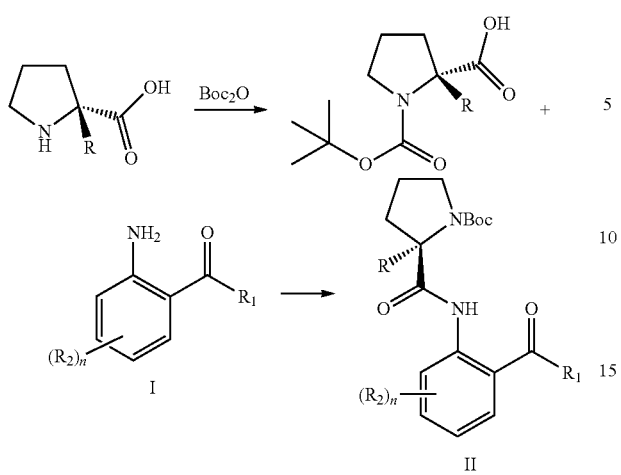

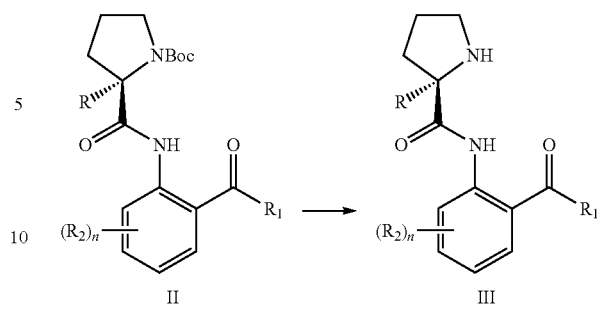

(i) (R)-2-substituted proline is reacted with di-tert-butyl dicarbonate to form (R)-1-(tert-butoxycarbonyl)-2-methylproline;

(ii) (R)-1-(tert-butoxycarbonyl)-2-substituted proline and a compound of formula I are subjected to a condensation reaction to obtain a compound of formula II;

wherein n, $R_1$ and $R_2$ are as defined above.

In another preferred embodiment, the compound of formula I is selected from the group consisting of 2-aminobenzophenone, (2-amino-5-chlorophenyl)benzophenone, (2-amino-5-fluorophenyl)benzophenone, (2-amino-5-bromophenyl)benzophenone, (2-amino-5-iodophenyl)benzophenone, (2-amino-5-trifluoromethylphenyl)benzophenone, 1-(2-amino-5-phenyl)ethanone, 1-(2-amino-5-chlorophenyl)ethanone, 1-(2-amino-5-phenyl)-2,2,2-trifluoroethanone, and 1-(2-amino-5-chlorophenyl)-2,2,2-trifluoroethanone.

In another preferred embodiment, step i) is carried out in an organic solvent in the presence of a base. In another preferred embodiment, the organic solvent is one or a mixed solvent of two or more selected from the group consisting of dichloromethane, methanol, ethanol, isopropanol, acetonitrile, tetrahydrofuran, 1,4-dioxane, DMSO and DMF. In another preferred embodiment, the base is one or a combination of two or more of potassium hydroxide, sodium hydroxide, lithium hydroxide, cesium carbonate, potassium carbonate, potassium hydrogencarbonate, sodium hydrogencarbonate, DBU, DIPEA, triethylamine and tetramethyl hydroxylamine.

In another preferred embodiment, step ii) is carried out in an organic solvent in the presence of a base and an acyl chloride. In another preferred embodiment, the organic solvent is one or a mixed solvent of two or more selected from the group consisting of dichloromethane, tetrahydrofuran, 1,4-dioxane, DMSO and DMF. In another preferred embodiment, the acyl chloride reagent is one or a combination of two or more selected from the group consisting of methanesulfonyl chloride, dichlorosulfoxide and oxalyl chloride. In another preferred embodiment, the base is one or a combination of two or more selected from the group consisting of N-methylimidazole, imidazole, potassium hydroxide, sodium hydroxide, lithium hydroxide, cesium carbonate, potassium carbonate, potassium hydrogencarbonate, sodium hydrogencarbonate, DBU, DIPEA, triethylamine and tetramethylhydroxylamine.

As shown in the above reaction formula, tert-butoxycarbonyl is removed from a compound of formula II to afford a compound of formula III.

In another preferred embodiment, the removal of the tert-butoxycarbonyl group is carried out in an organic solvent in the presence of an acid. In another preferred embodiment, the organic solvent is one or a mixed solvent of two or more selected from the group consisting of dichloromethane, 1,2-dichlorohexane, tetrahydrofuran, methanol, ethanol, 1,4-dioxane, DMSO and DMF. In another preferred embodiment, the acid is one or a combination of two or more selected from the group consisting of trifluoroacetic acid, hydrochloric acid, sulfuric acid and nitric acid.

In the present invention, the compound of formula IV is synthesized by the following step:

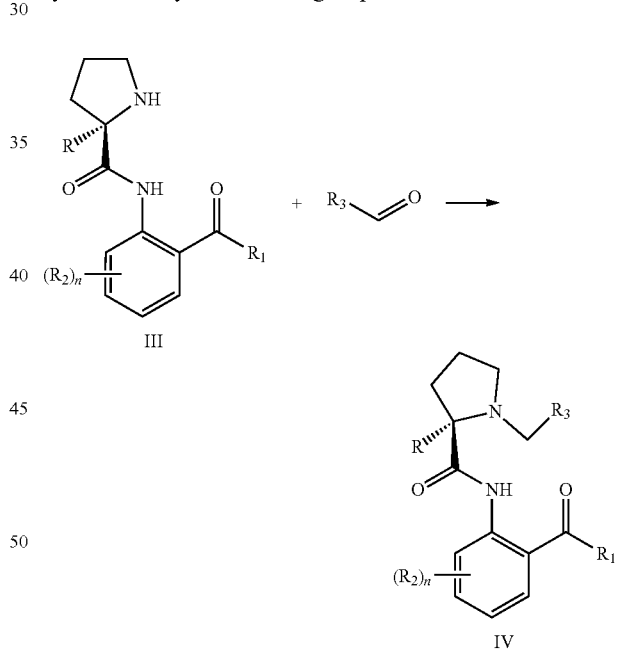

a compound of formula III is subjected to a reductive amination reaction with $R_3CHO$ to form the compound of formula IV, wherein n, R, $R_1$, $R_2$ and $R_3$ are as defined above.

In another preferred embodiment, $R_3CHO$ is acetaldehyde, propionaldehyde, benzaldehyde, phenylacetaldehyde, phenylpropanal, 3,4-dichlorophenylacetaldehyde or 3,4-dichlorophenylpropanal.

In another preferred embodiment, $R_3CHO$ is acetaldehyde, propionaldehyde, benzaldehyde, phenylacetaldehyde, phenylpropanal or 3,4-dichlorophenylacetaldehyde.

In another preferred embodiment, the reductive amination reaction is carried out in an organic solvent in the presence of a catalytic amount of an acid and a reducing reagent.

In another preferred embodiment, the organic solvent is one or a mixed solvent of two or more selected from the group consisting of dichloromethane, 1,2-dichlorohexane and tetrahydrofuran. In another preferred embodiment, the acid is one or a combination of two or more selected from the group consisting of formic acid, acetic acid, propionic acid and butyric acid. In another preferred embodiment, the reducing agent is one or a combination of two or more selected from the group consisting of sodium borohydride, sodium triacetoxyborohydride and sodium cyanoborohydride.

In the present invention, the compound of formula IV is synthesized by the following step:

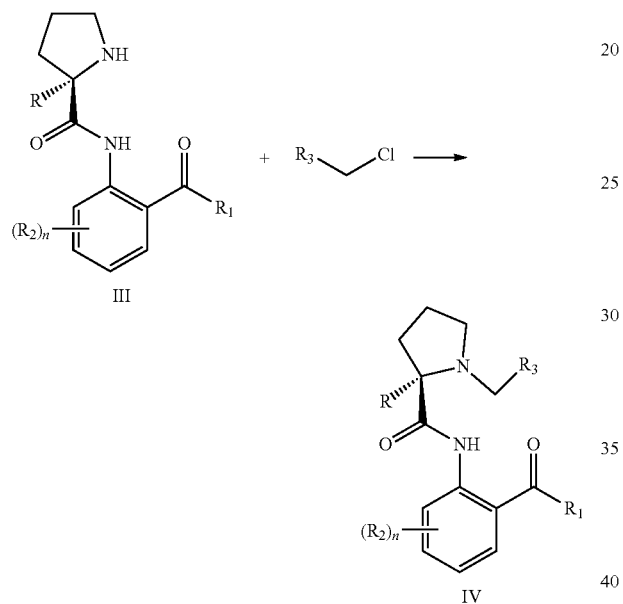

a compound of formula III is subjected to a substitution reaction with $R_3CH_2Cl$ to afford the compound of formula IV, wherein n, R, $R_1$, $R_2$ and $R_3$ are as defined above.

In another preferred embodiment, $R_3CH_2Cl$ is benzyl chloride, 1,2-dichloro-4-(chloromethyl)phenyl, 1-chloro-4-(chloromethyl)phenyl, 1-fluoro-4-(chloromethyl)phenyl, 1-bromo-4-(chloromethyl)phenyl, 1-iodo-4-(chloromethyl)phenyl, 2-chloro-4-(chloromethyl)phenyl, 3-chloro-4-(chloromethyl)phenyl, 2-fluoro-4-(chloromethyl)phenyl, 2-bromo-4-(chloromethyl)phenyl, 3-fluoro-4-(chloromethyl)phenyl, 3-bromo-4-(chloromethyl)phenyl, 1-chloroethane or 1-chloropropane.

In another preferred embodiment, $R_3CH_2Cl$ is benzyl chloride, 1,2-dichloro-4-(chloromethyl)phenyl, 1-chloro-4-(chloromethyl)phenyl, 1-fluoro-4-(chloromethyl)phenyl, 2-chloro-4-(chloromethyl)phenyl, 3-chloro-4-(chloromethyl)phenyl, 2-fluoro-4-(chloromethyl)phenyl, 3-fluoro-4-(chloromethyl)phenyl, 1-chloroethane or 1-chloropropane.

In another preferred embodiment, the substitution reaction is carried out in the presence of a base in an organic solvent. In another preferred embodiment, the organic solvent is one or a mixed solvent of two or more selected from the group consisting of dichloromethane, 1,2-dichlorohexane and tetrahydrofuran. In another preferred embodiment, the base is one or a mixture of two or more selected from the group consisting of sodium hydroxide, potassium hydroxide, sodium carbonate and cesium carbonate.

The structure of novel quaternary carbon ligand is as follows.

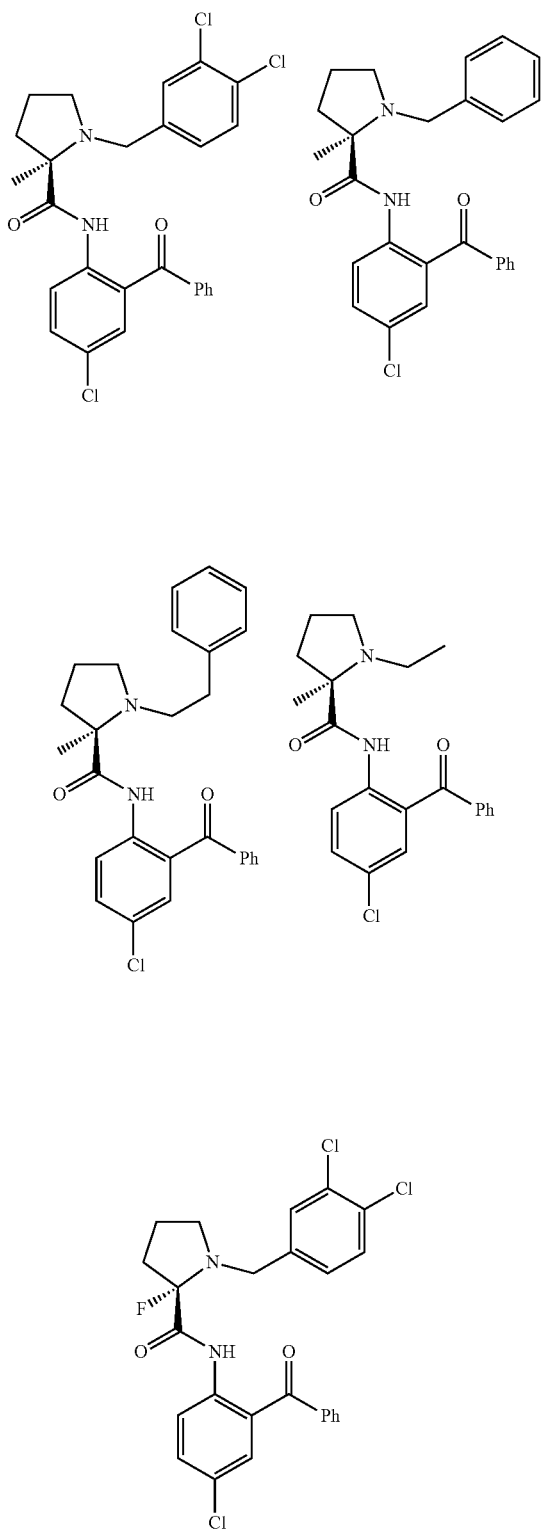

-continued
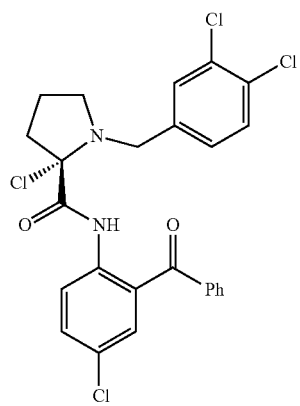
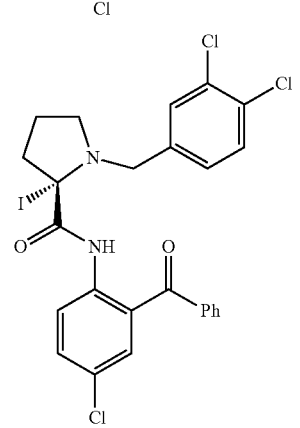
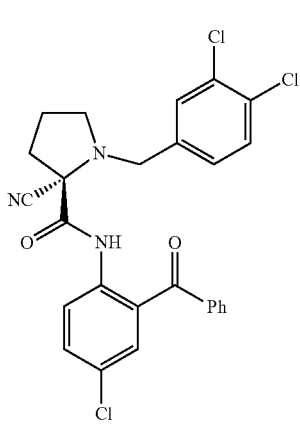
-continued
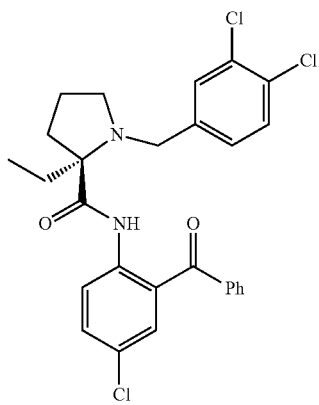
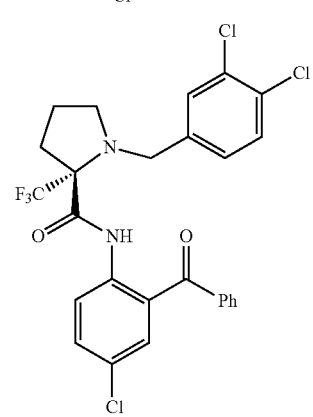
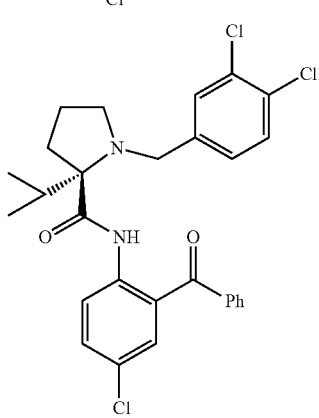
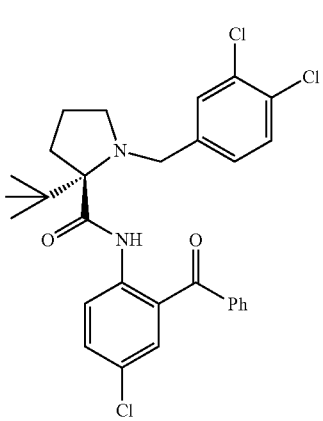

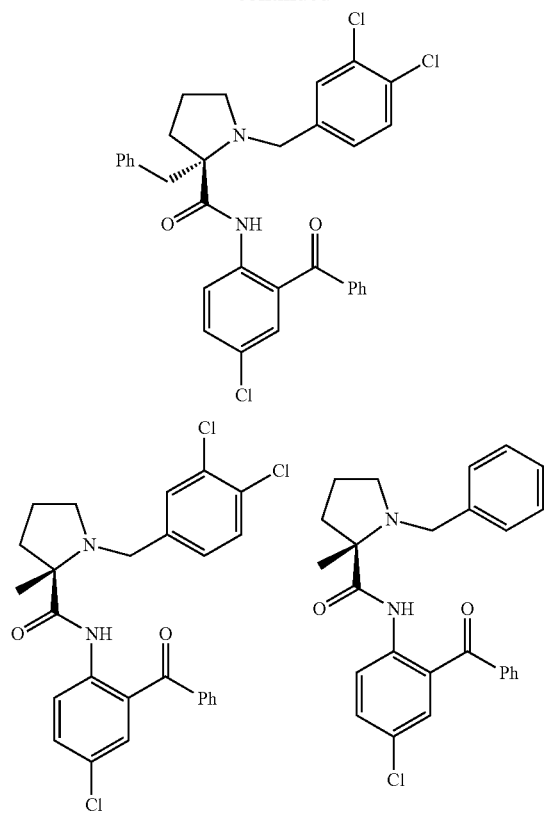
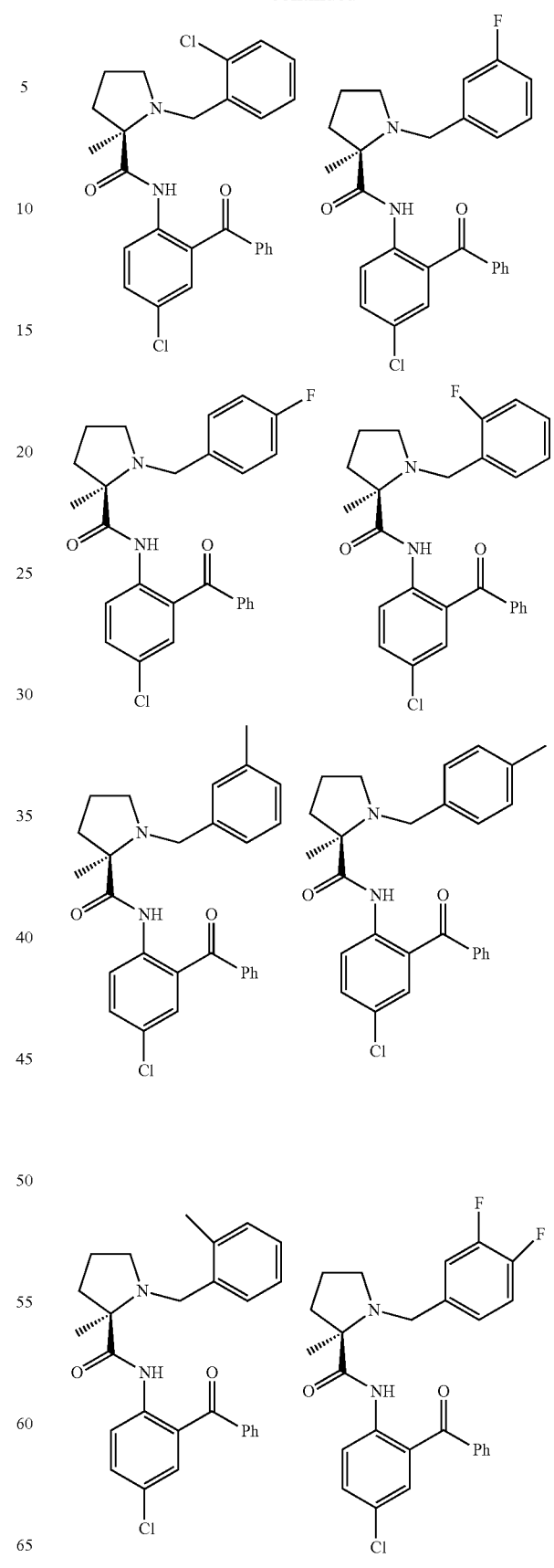

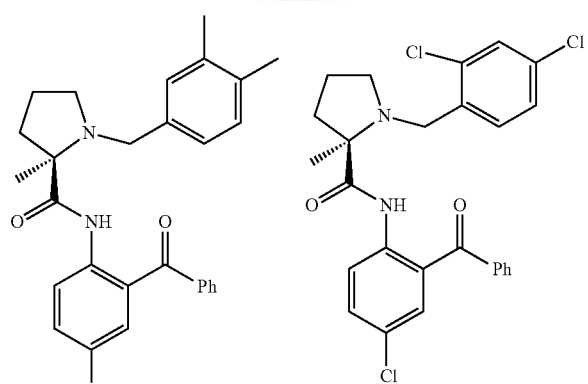
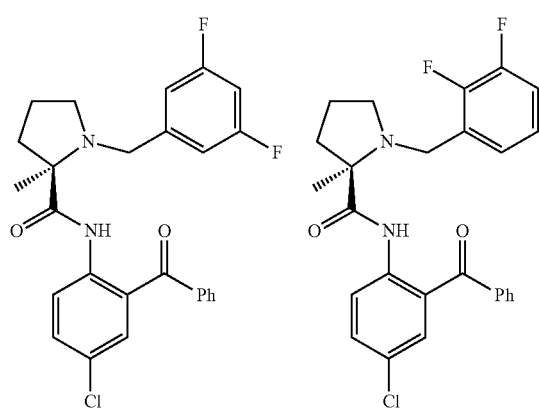
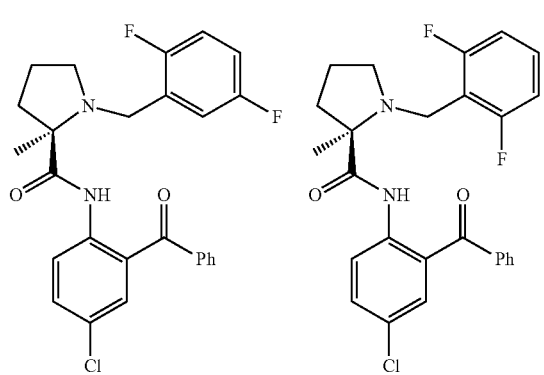
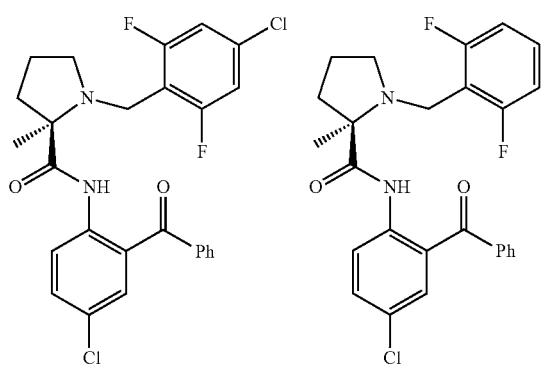
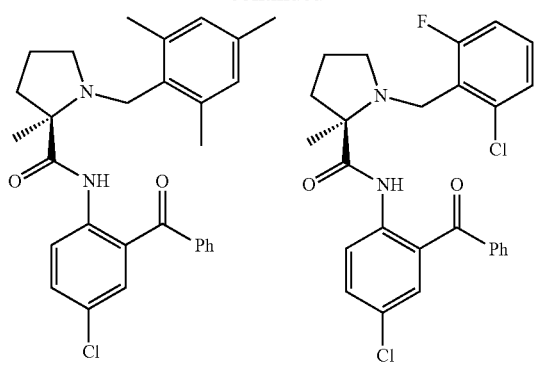
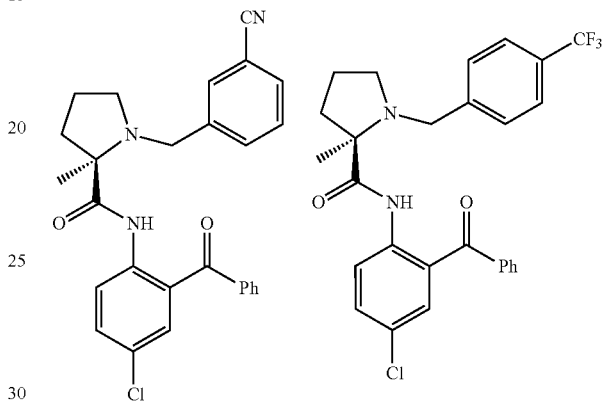
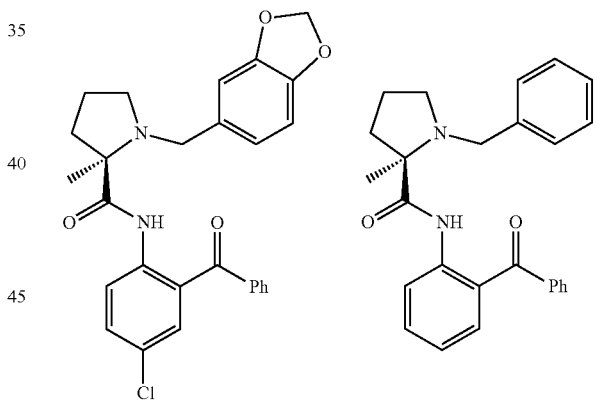
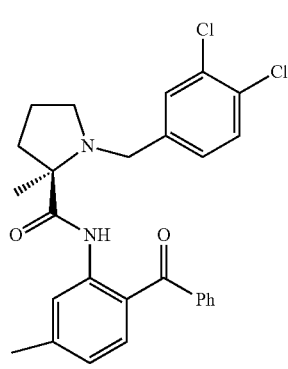

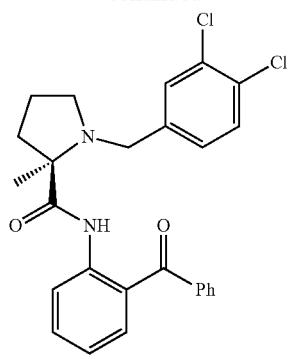
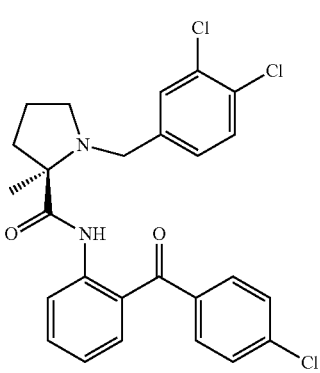
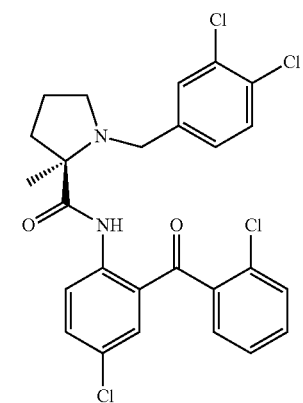
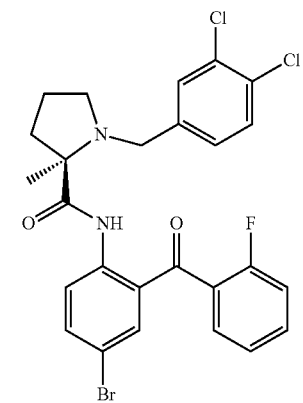
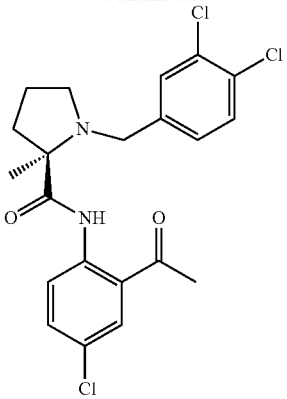 [SMILES: C[C@]1(C(=O)Nc2ccc(Cl)cc2C(=O)c2ccccc2)CCCN1Cc1ccc(Br)c(Br)c1]
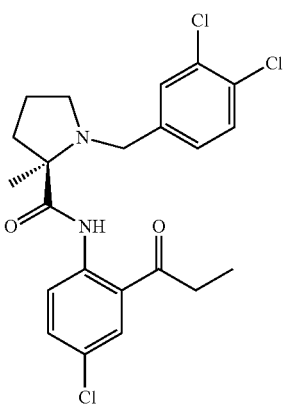
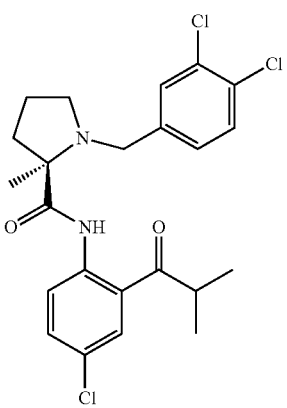
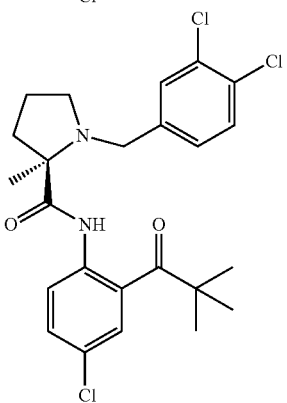

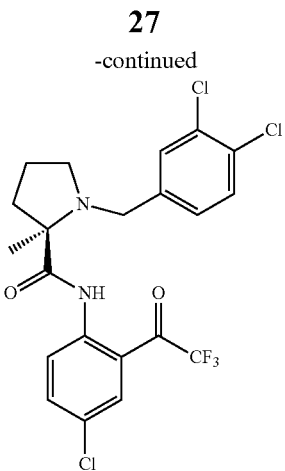
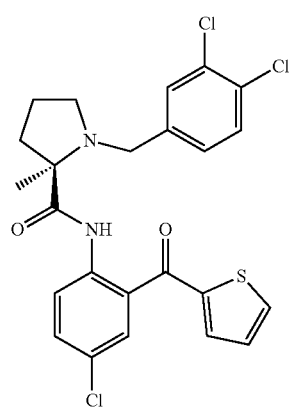
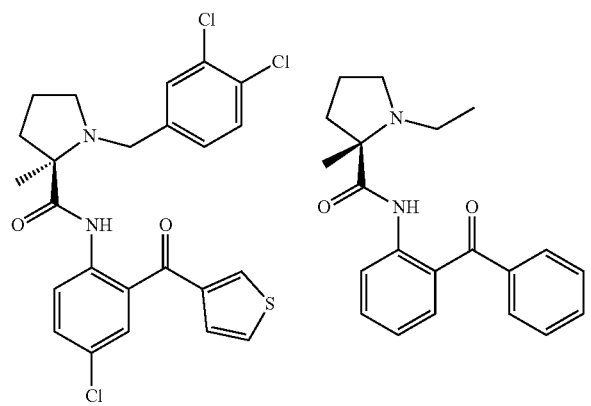
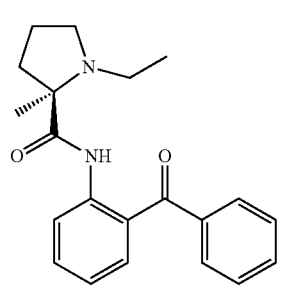
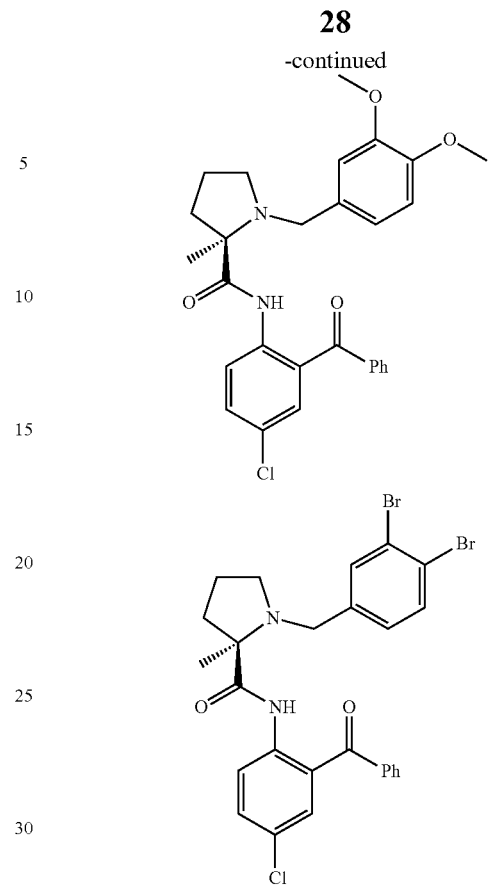
In the present invention, the compound of formula VI is synthesized by the following step:
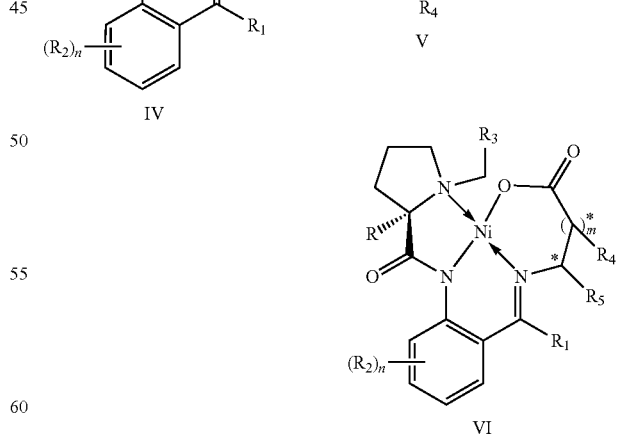
a compound of formula IV is reacted with a non-natural amino acid of formula V under the action of a nickel salt to form the compound of formula VI,
wherein n, m, $R_1$, $R_2$, $R_3$, $R_4$ and $R_5$ are as defined above.

In another preferred embodiment, the compound of formula V is a variety of non-natural alpha amino acids, alpha substituted beta amino acids, and beta substituted beta amino acids, such as alanine, phenylalanine, phenylalanine, 3-methoxyphenylalanine, 3-methylphenylalanine, 4-fluorophenylalanine, 3-methoxyphenylglycine, 3-bromophenylglycine, 2-amino-3-(3,5-diiodo-4-hydroxyphenyl)propionic acid, 2-amino-3-(naphth-1-yl)propionic acid, 2-amino-3-(benzothiophen-3-yl)propionic acid, 2-amino-3-(thiophen-3-yl)propionic acid, 2-amino-2-cyclobutylacetic acid, 2-amino-4,4,4-trifluorobutyric acid, 2-aminovaleric acid, 2-amino-3-methylbutyric acid, 2-amino-4-methylthiobutyric acid, 2-amino-3-(1H-indenyl)propionic acid, 2-amino-5-methyl-4-hexenoic acid, 2-aminoglutaric acid, 2,5-diamino-5-pentanone acid, homocysteine, 3-amino-2-benzylpropionic acid, 3-amino-2-(4-fluorobenzyl)propionic acid, 3-amino-2-(4-methoxybenzyl)propionic acid, 3-amino-2-methylpropionic acid, 2-(aminomethyl)-4-methylpentanoic acid, 3-amino-2-cyclohexylpropionic acid, 3-amino-2-phenylpropionic acid, 3-amino-2-(4-chlorophenyl)propionic acid, 3-amino-2-(4-methoxyphenyl)propionic acid, 3-amino-2-(naphth-1-yl)propionic acid 3-amino-propionic acid, 3-amino-3-phenylpropionic acid, 3-amino-3-(4-methyl)phenylpropionic acid, 3-amino-3-(3-methyl)phenylpropionic acid, 3-amino-3-(2-methyl)phenylpropionic acid, 3-amino-3-(2-fluoro)phenylpropionic acid, 3-amino-3-(4-chloro)phenylpropionic acid, 3-amino-3-(3,4-dimethoxy)phenylpropionic acid, 3-amino-3-(4-methoxy)phenylpropionic acid, 3-amino-3-(3-methoxy)phenylpropionic acid, 3-amino-3-(pyridin-4-yl)propionic acid, 3-amino-3-(thiophen-2-yl)propionic acid, 3-amino-3-cyclohexylpropionic acid, 3-amino-3-(naphth-2-yl)propionic acid or 3-amino-3-(2,4,5-trifluoro)phenylpropionic acid.

In another preferred embodiment, a compound of formula IV is reacted with a compound of formula V in an organic solvent in the presence of a base. In another preferred embodiment, the organic solvent is one or a mixed solvents of two or more selected from the group consisting of dichloromethane, 1,2-dichlorohexane, tetrahydrofuran, methanol, ethanol, 1,4-dioxane, DMSO and DMF. In another preferred embodiment, the base is one or a combination of two or more selected from the group consisting of potassium hydroxide, sodium hydroxide, lithium hydroxide, cesium carbonate, potassium carbonate, potassium hydrogencarbonate, sodium hydrogencarbonate, DBU, DIPEA, triethylamine and tetramethyl hydroxylamine.

The structure of the novel alpha amino acid nickel chelate is as follows:

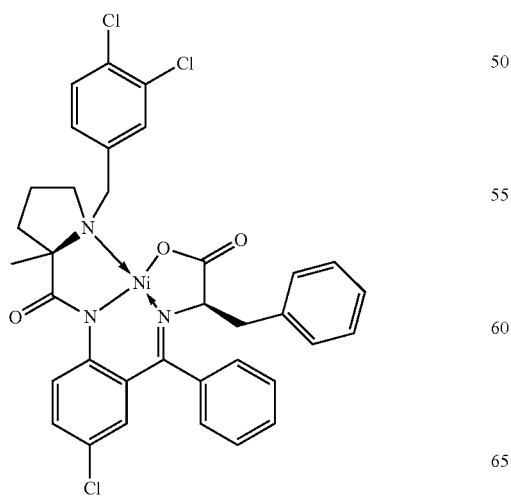

-continued

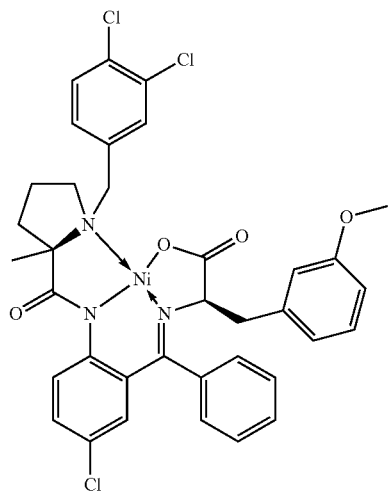

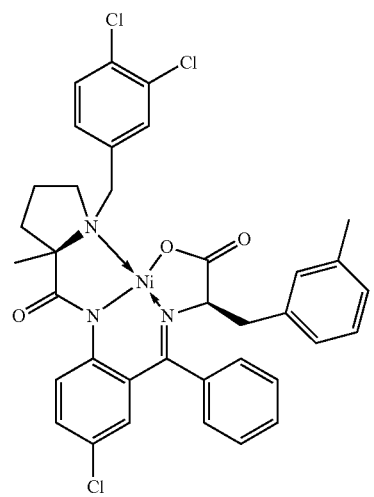

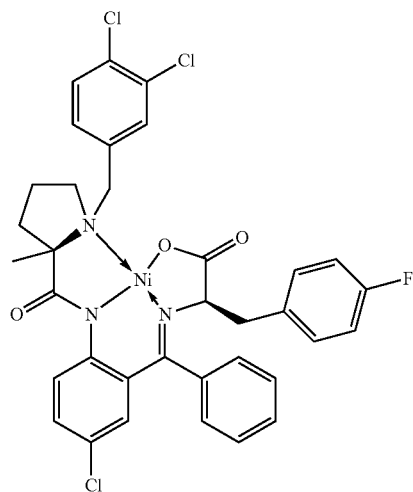

31
-continued
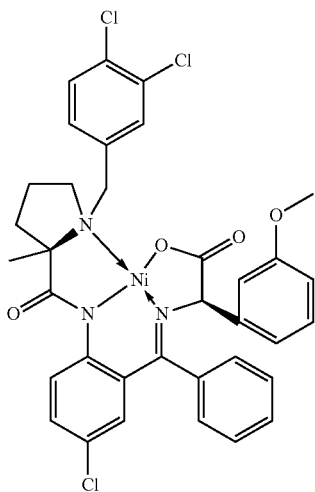
32
-continued
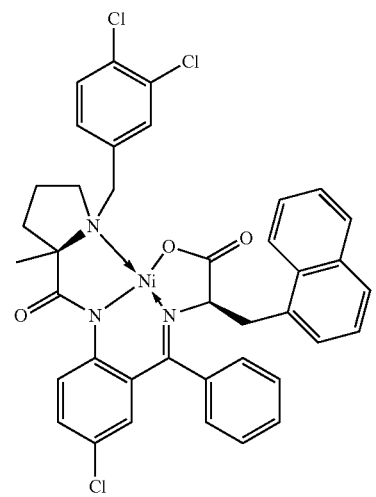
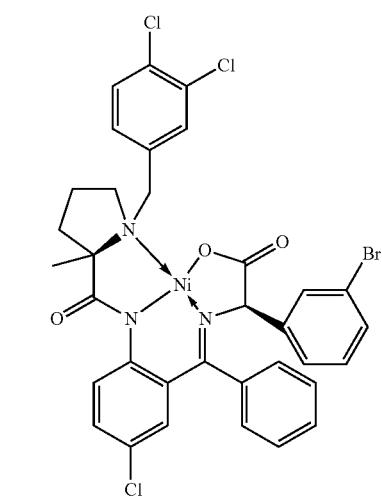
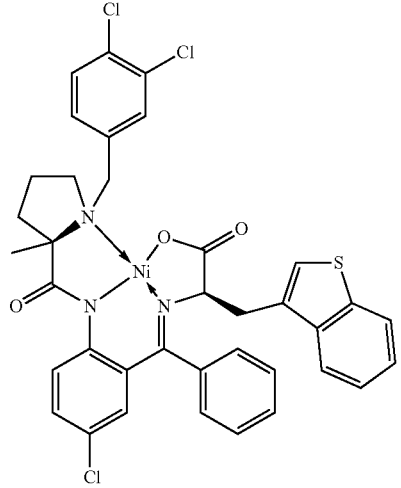
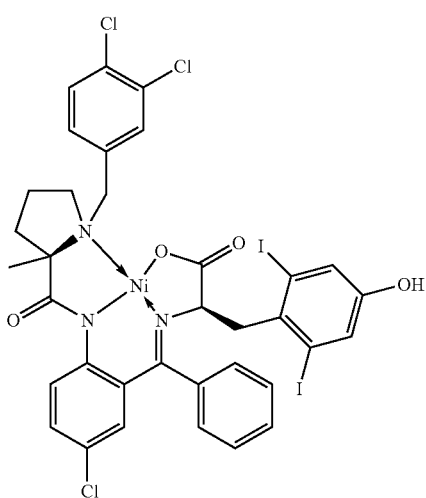
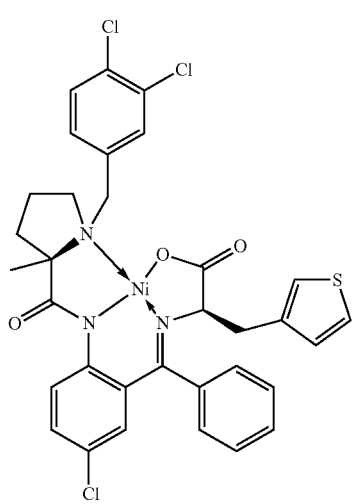

33
-continued
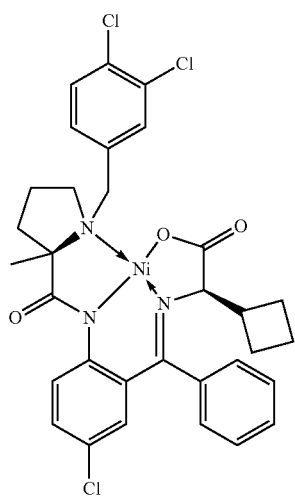
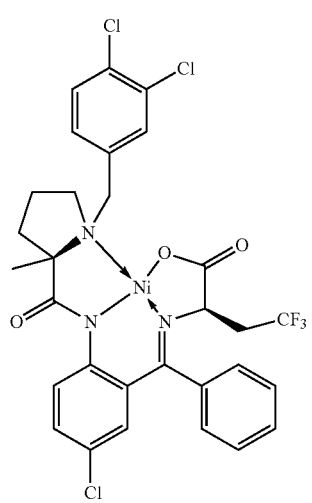
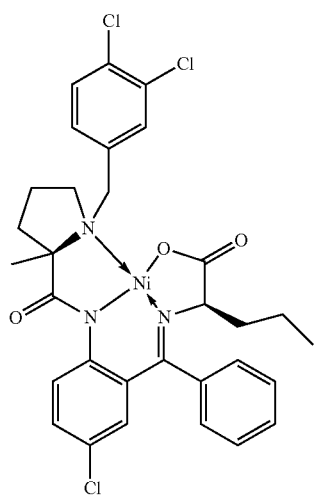
34
-continued
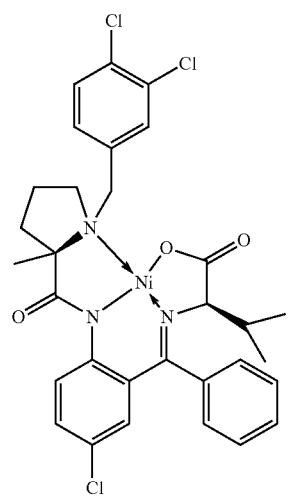
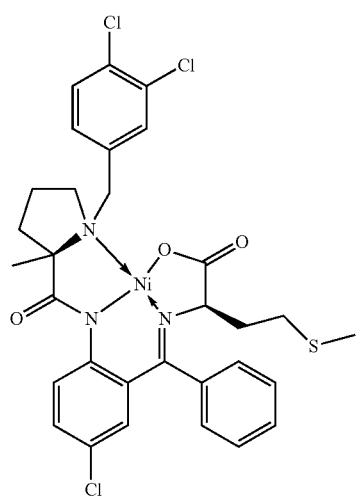
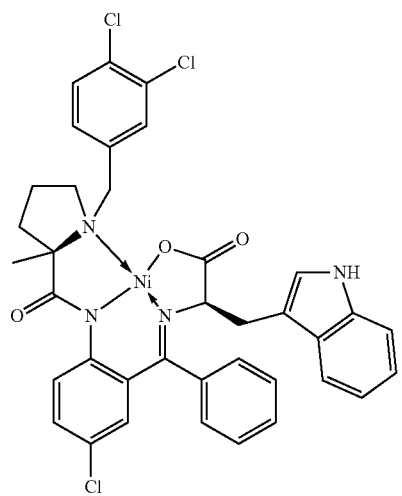

35
-continued
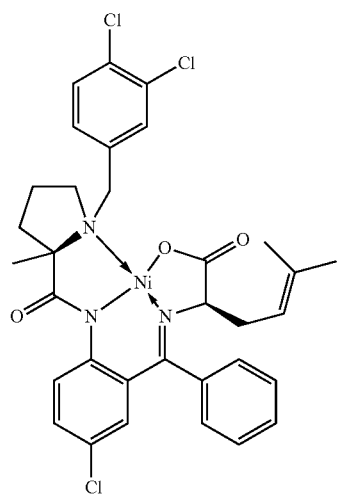
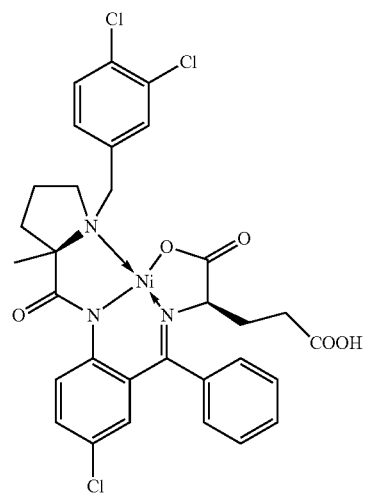
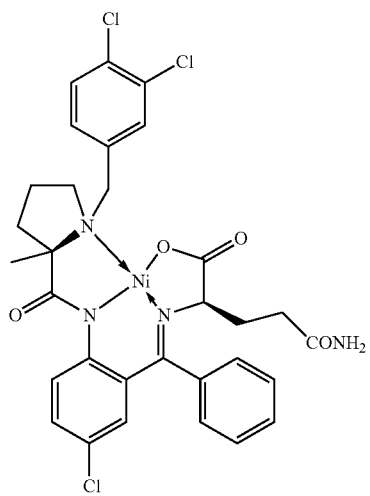
36
-continued
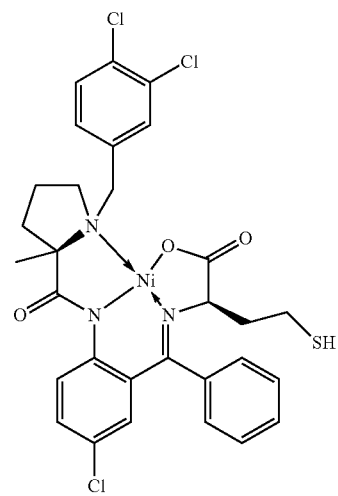
The structure of the novel α-substituted β amino acid nickel chelate is as follows:
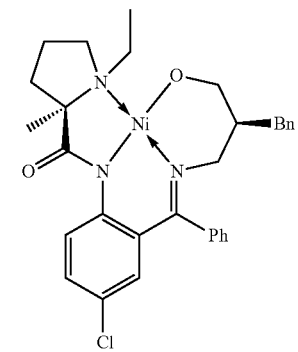
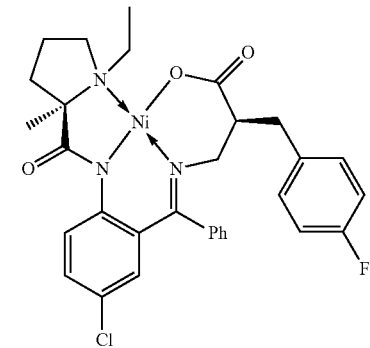
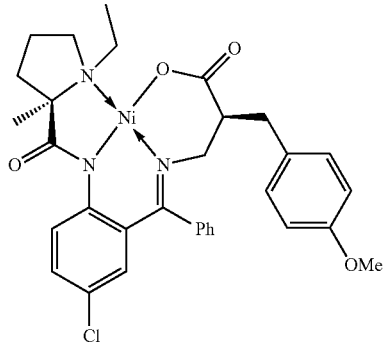

37
-continued
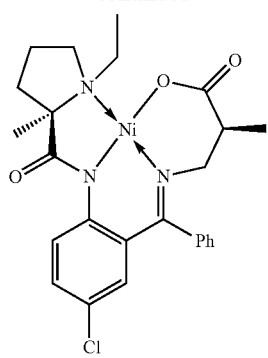
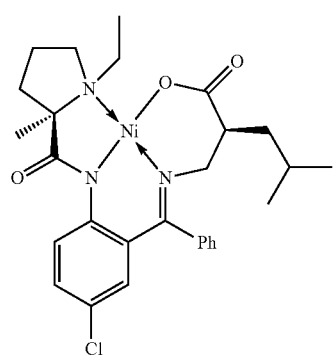
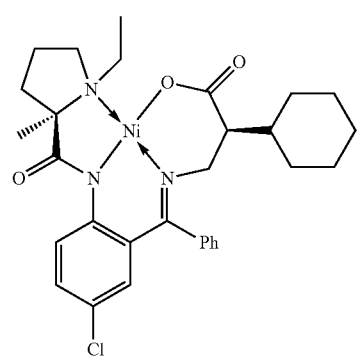
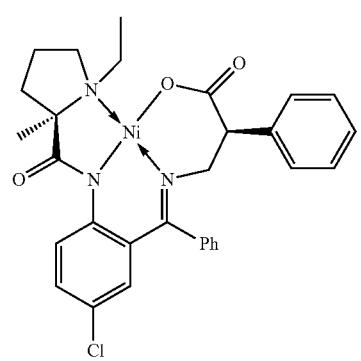
38
-continued
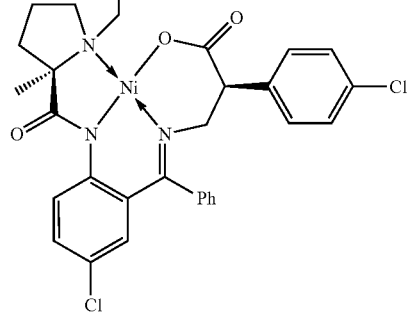
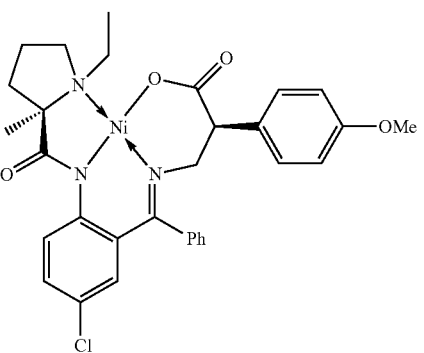
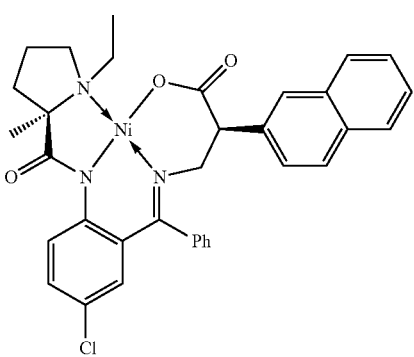
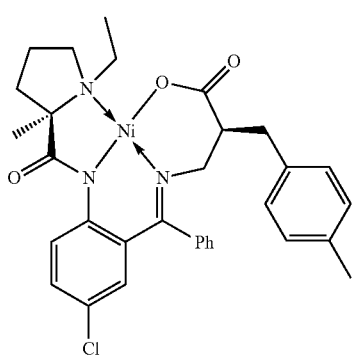

39
-continued
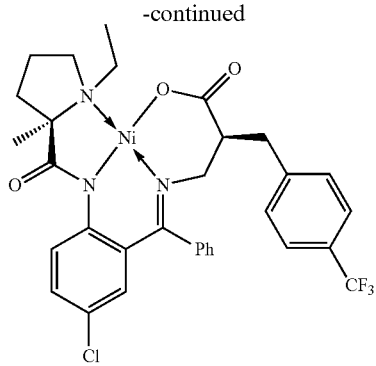
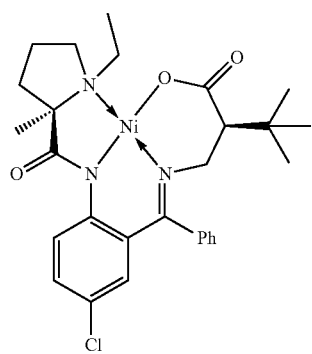
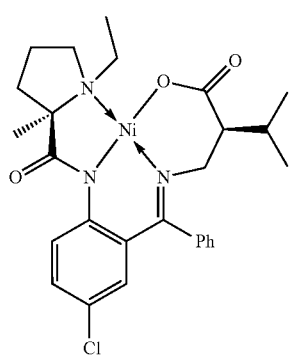
40
-continued
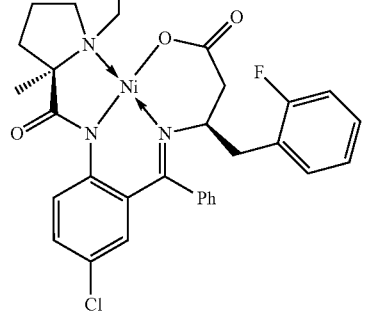
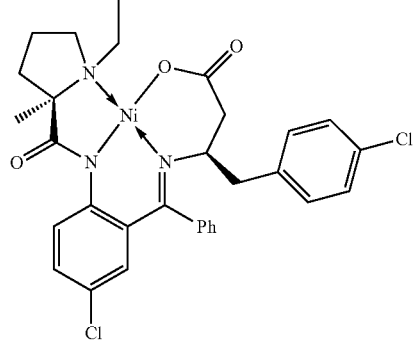
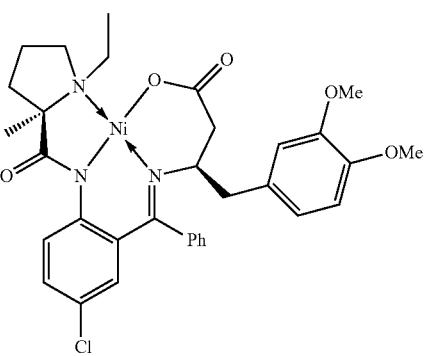
The structure of the novel β-substituted β amino acid nickel chelate is as follows:
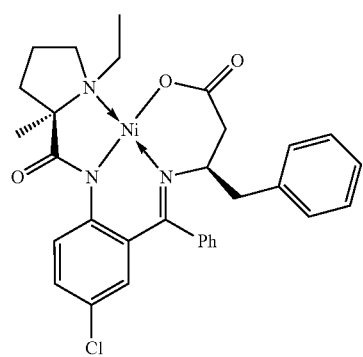
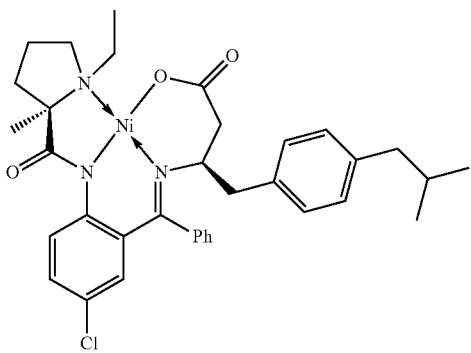

41
-continued
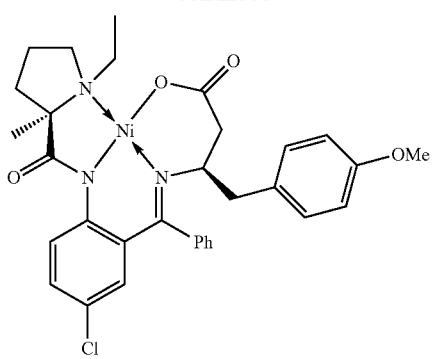
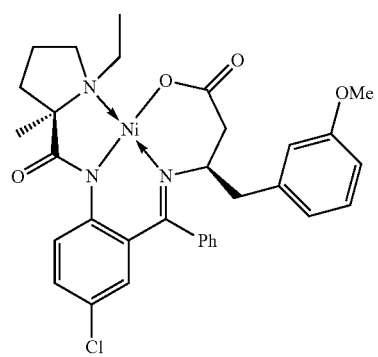
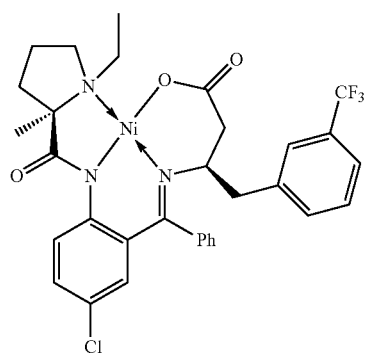
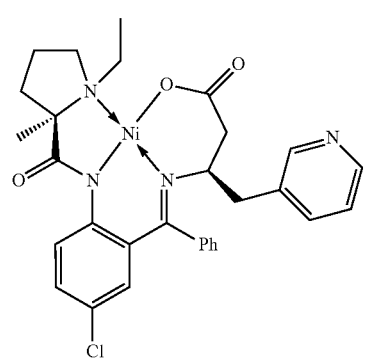
42
-continued
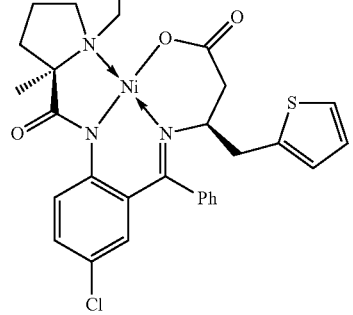
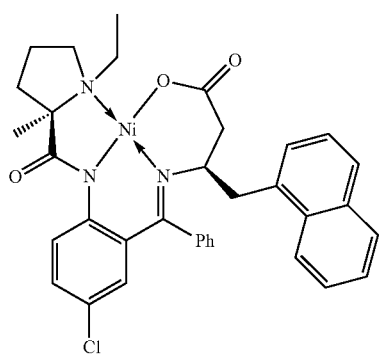
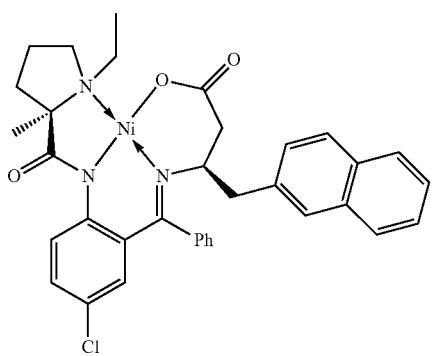
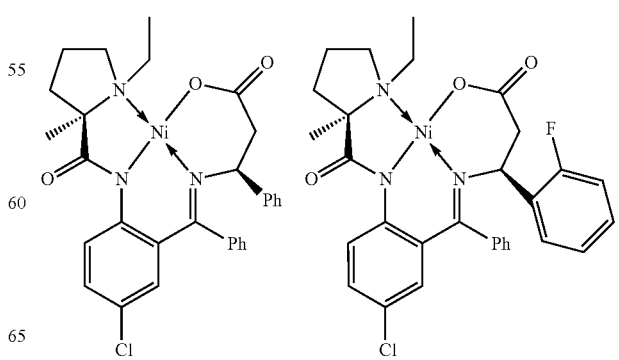

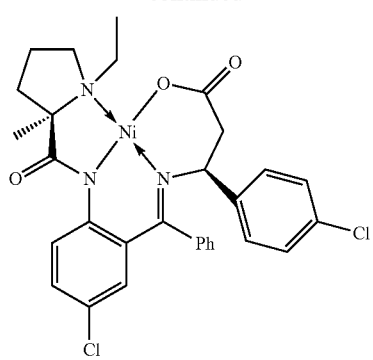
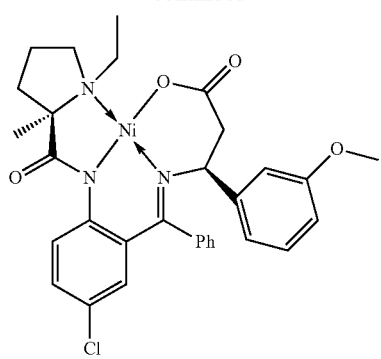
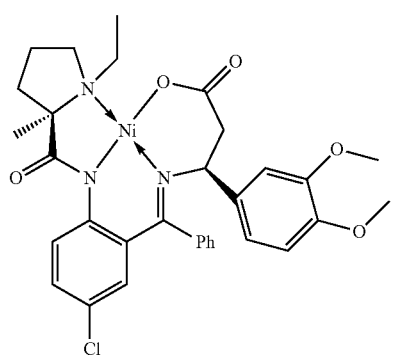
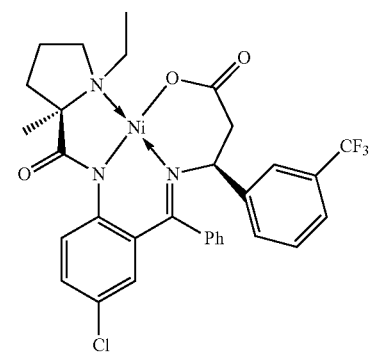
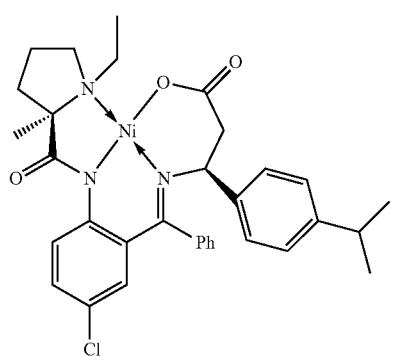
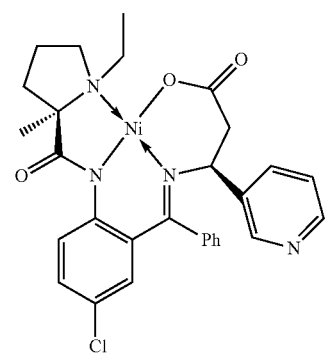
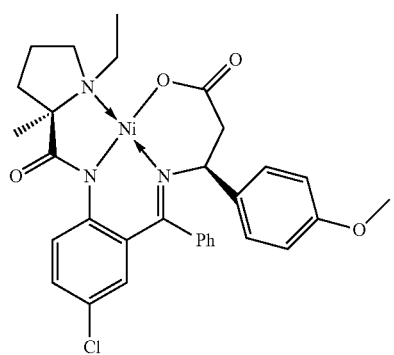
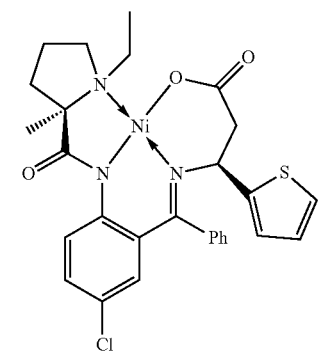

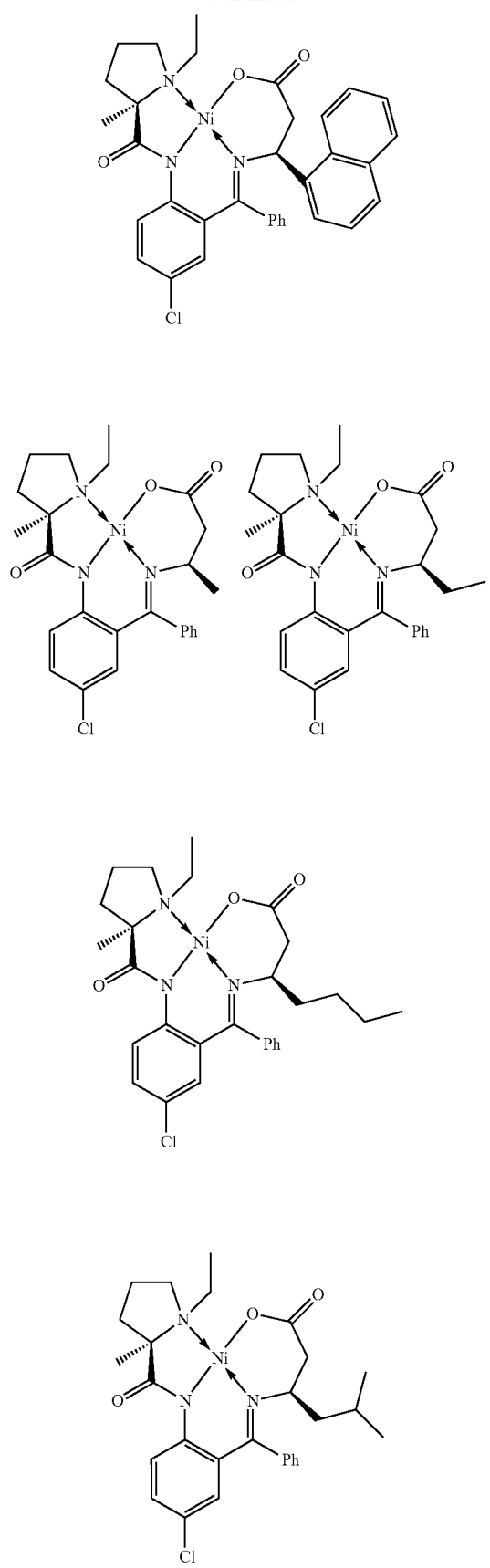

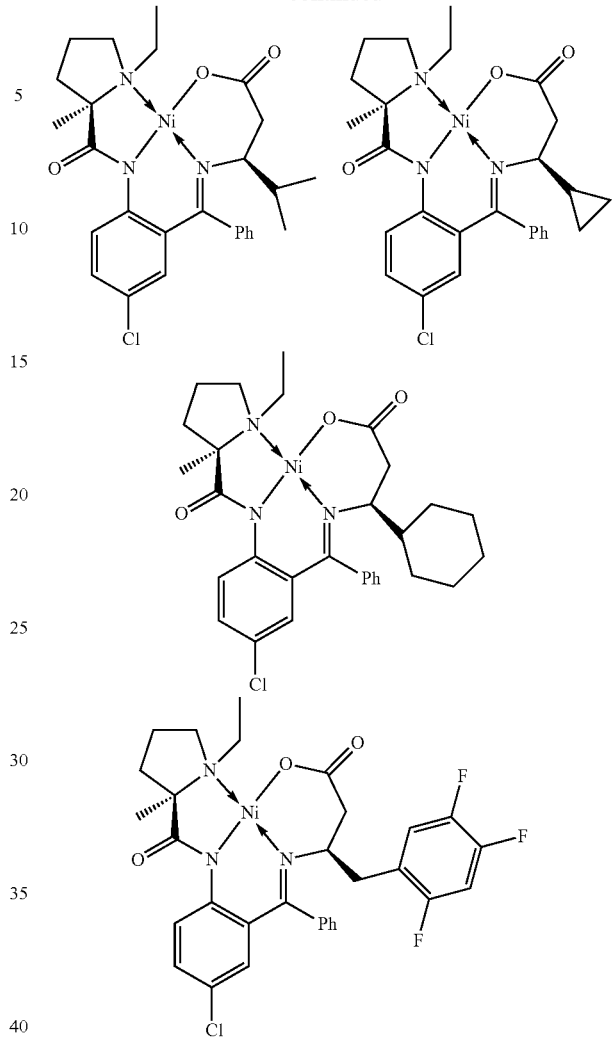

The method for synthesizing the (S)-β³-amino acid of the present invention, comprises the step of hydrolyzing a compound of the formula VI to obtain the (S)-β³-amino acid represented by formula VII,

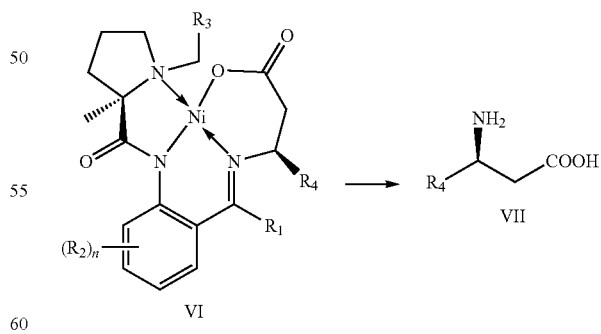

wherein n, m, $R_1$, $R_2$, $R_3$, $R_4$ and $R_5$ are as defined above.

In another preferred embodiment, the hydrolysis is carried out in an organic solvent in the presence of a base, wherein the organic solvent is one or a mixture of two or more selected from the group consisting of methanol, ethanol, isopropanol, acetonitrile, tetrahydrofuran, 1,4-dioxane, DMSO and DMF. In another preferred embodiment, the base is one or a composition of two or more selected from the group consisting of DBU, potassium t-butoxide, sodium t-butoxide, sodium hydrogen, potassium hydroxide, sodium hydroxide, cesium carbonate, potassium carbonate, potassium hydrogencarbonate and lithium hydroxide.

In another preferred embodiment, the method for synthesizing the non-natural amino acid comprises the following steps:

(i) reacting (R)-2-substituted proline with di-tert-butyl dicarbonate to form (R)-1-(tert-butoxycarbonyl)-2-methylproline;

(ii) subjecting (R)-1-(tert-butoxycarbonyl)-2-substituted proline to a condensation reaction with a compound of formula I to obtain a compound of formula II;

(iii) removing tert-butoxycarbonyl from the compound of formula II to obtain a compound of formula III;

(iv) subjecting the compound of formula III to a reductive amination reaction with $R_3CHO$ to obtain a compound of formula IV;

(v) reacting the compound of formula IV with a $\beta^3$ amino acid of formula V under the action of nickel acetate to form a compound of VI;

(vi) hydrolyzing the compound of VI to form a compound of VII,

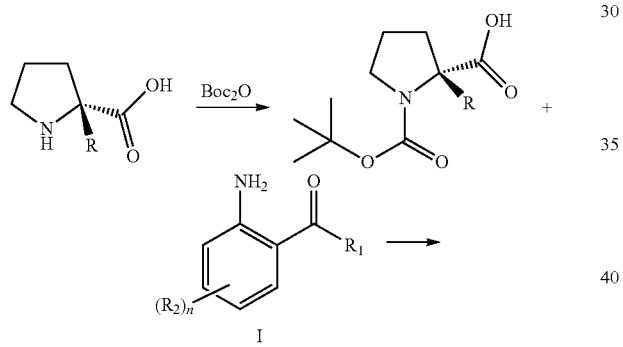

I

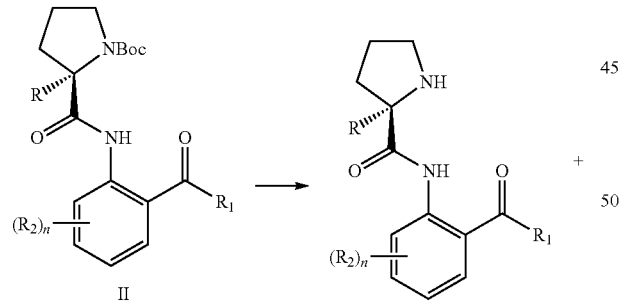

II

III

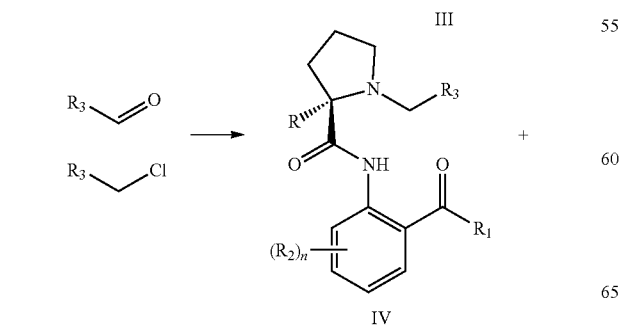

IV

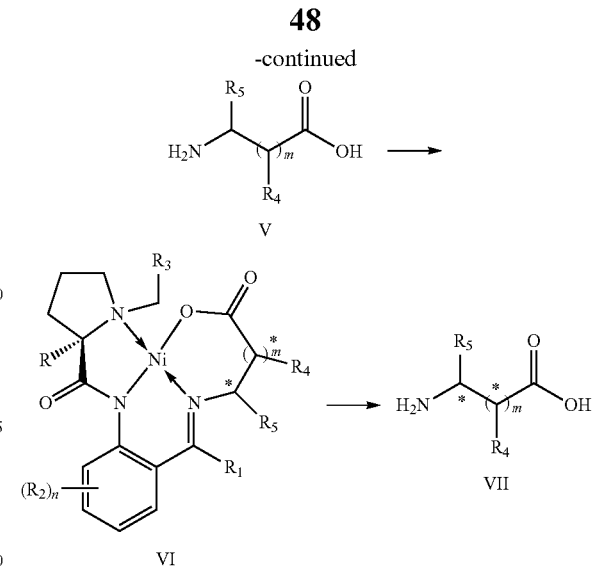

V

VI

VII wherein n, m, $R_1$, $R_2$, $R_3$, $R_4$ and $R_5$ are as defined above. The preferred conditions for each step are as indicated above.

The method for synthesizing Maraviroc in the present invention comprises the step of synthesizing a Maraviroc intermediate, wherein the Maraviroc intermediate is a compound of the formula VI:

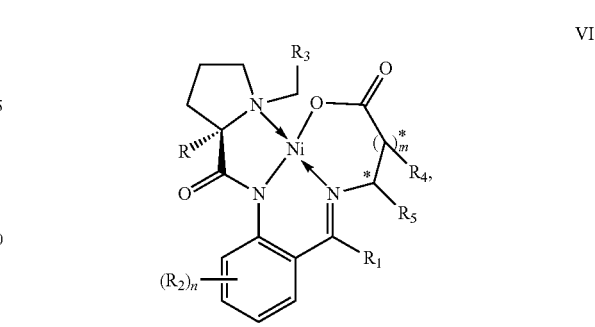

VI wherein n, m, $R_1$, $R_2$, $R_3$, $R_4$ and $R_5$ are as defined above, and $R_4$ is phenyl.

In another preferred embodiment, the synthesis step of the Maraviroc intermediate, the compound of formula VI is as described above.

In another preferred embodiment, the method for synthesizing Maraviroc also includes the following step:

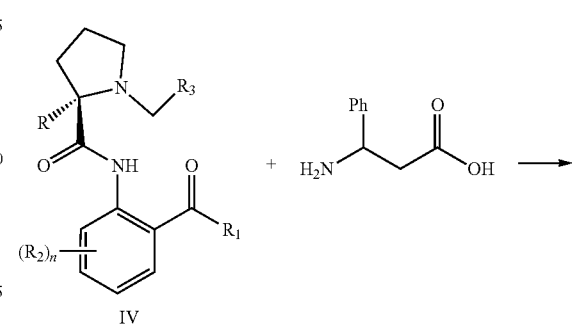

IV

-continued

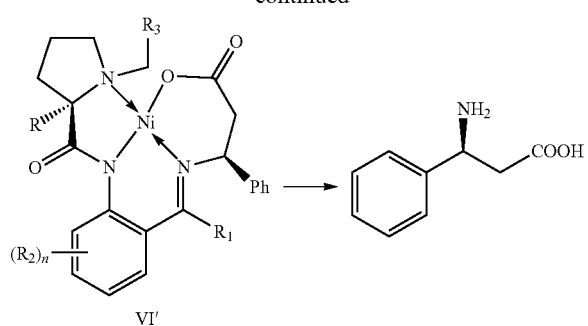

VI'

(i) reacting a compound of formula IV with 3-amino-3-phenylpropionic acid under the action of nickel acetate to form a compound of formula VI';

(ii) hydrolyzing the compound of formula VI' to obtain (S)-$\beta^3$-phenylalanine, wherein n, $R_1$, $R_2$ and $R_3$ are as defined above.

In another preferred embodiment, the method for synthesizing Maraviroc further includes the following step:

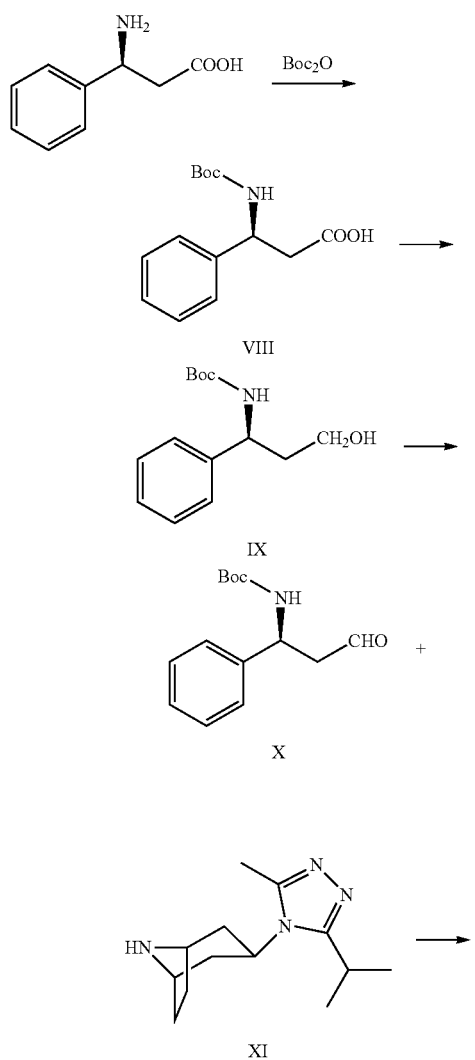

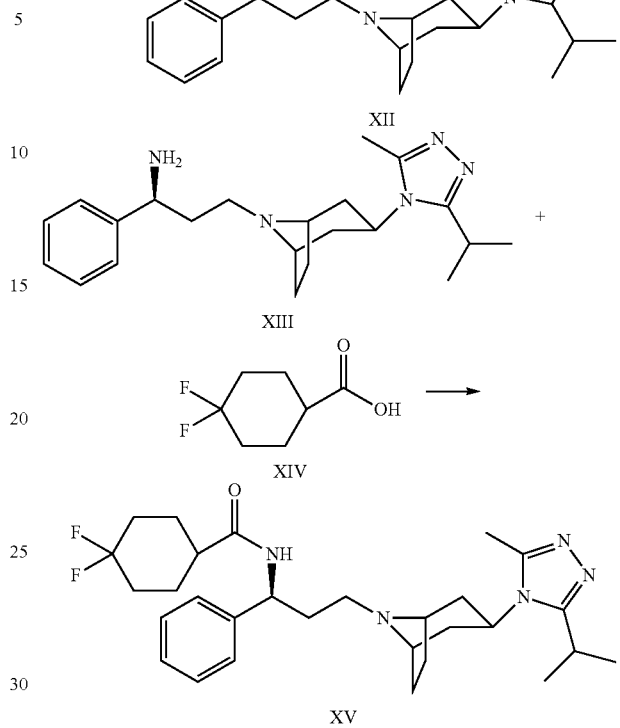

(a) reacting (S)-$\beta^3$-phenylalanine with di-tert-butyl dicarbonate to obtain a compound of formula VIII;

(b) subjecting the compound of formula VIII to a reduction reaction to give a compound of formula IX;

(c) subjecting the compound of formula IX to an oxidation reaction to give a compound of formula X;

(d) subjecting the compound of formula X to a reductive amination reaction with a compound of formula XI to give a compound of formula XII;

(e) removing tert-butoxycarbonyl from the compound of formula XII to give a compound of formula XIII;

(f) subjecting the compound of formula XIII to a condensation reaction with a compound of formula XIV to obtain Maraviroc having formula XV.

In another preferred embodiment, (S)-$\beta^3$-phenylalanine is reacted with di-tert-butyl dicarbonate in an organic solvent in the presence of a base, wherein the organic solvent is one or a mixed solvent of two or more selected from the group consisting of dichloromethane, methanol, ethanol, isopropanol, acetonitrile, tetrahydrofuran, 1,4-dioxane, DMSO and DMF; and the base is one or a combination of two or more selected from the group consisting of potassium hydroxide, sodium hydroxide, lithium hydroxide, cesium carbonate, potassium carbonate, potassium hydrogencarbonate, sodium hydrogencarbonate, DBU, DIPEA and triethylamine.

In another preferred embodiment, the step (b) is carried out in an organic solvent in the presence of a reducing agent, wherein the organic solvent is one or a mixed solvent of two or more selected from the group consisting of dichloromethane, tetrahydrofuran, 1,4-dioxane, DMSO and DMF; and the reducing agent is one or a combination of two or more selected from the group consisting of sodium borohydride, lithium aluminum hydride and borane.

In another preferred embodiment, the step (c) is carried out in an organic solvent in the presence of an oxidizing agent, wherein the organic solvent is one or a mixed solvent of two or more selected from the group consisting of dichloromethane, tetrahydrofuran, 1,4-dioxane, DMSO and DMF; and the oxidizing agent is one or a combination of two or more selected from the group consisting of Collins oxidizing agent, PCC oxidizing agent, PDC oxidizing agent, Swern oxidizing agent, Dess-martin oxidizing agent and IBX oxidizing agent.

In another preferred embodiment, the step (d) is carried out in an organic solvent in the presence of a catalytic amount of an acid and a reducing agent, wherein the organic solvent is one or a mixed solvent of two or more selected from the group consisting of dichloromethane, 1,2-dichlorohexane and tetrahydrofuran; the acid is one or a combination of two or more selected from the group consisting of formic acid, acetic acid, propionic acid, and butyric acid; and the reducing agent is one or a combination of two or more selected from the group consisting of sodium borohydride, sodium triacetoxyborohydride and sodium cyanoborohydride.

In another preferred embodiment, the step (e) is carried out in an organic solvent in the presence of an acid, wherein the organic solvent is one or a mixed solvent of two or more selected from the group consisting of dichloromethane, 1,2-dichlorohexane, tetrahydrofuran, methanol, ethanol, 1,4-dioxane, DMSO and DMF; and the acid is one or a combination of two or more selected from the group consisting of trifluoroacetic acid, hydrochloric acid, sulfuric acid and nitric acid.

In another preferred embodiment, the step (f) is carried out in an organic solvent in the presence of a condensation reagent, wherein the organic solvent is one or a mixed solvent of two or more selected from the group consisting of dichloromethane, 1,2-dichlorohexane, tetrahydrofuran, methanol, ethanol, 1,4-dioxane, DMSO and DMF; and the condensation agent is one or a combination of two or more selected from the group consisting of BOP, PyBOP, EDCI, DCC, HOBT, HATU, and HBTU.

In a preferred embodiment of the invention, the synthesis route for key intermediate of Maraviroc, (S)-3-amino-3-phenylpropionic acid is as follows.

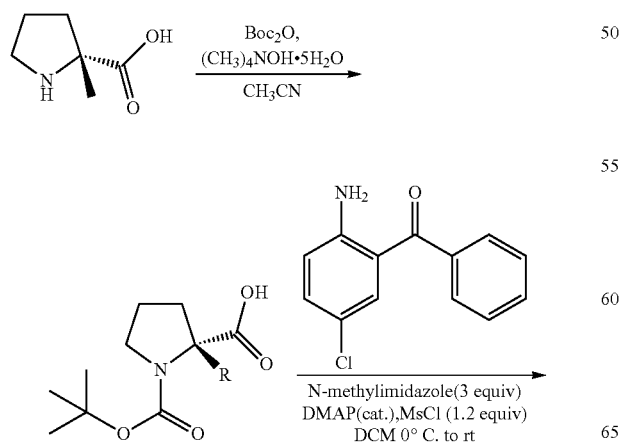

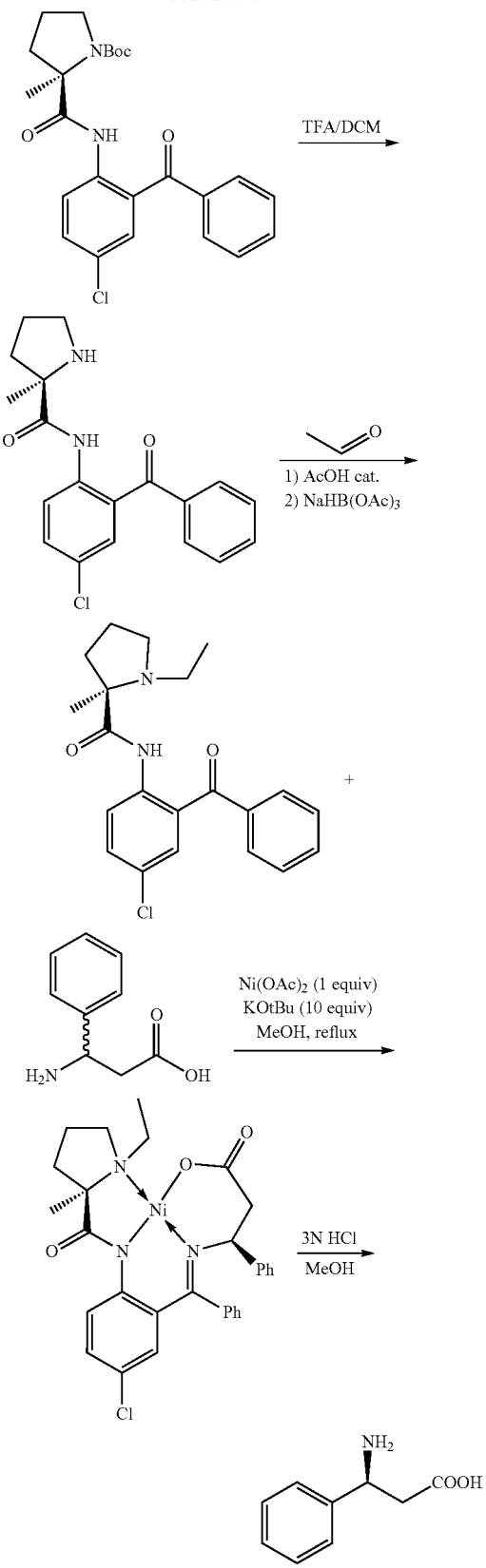

In a preferred embodiment of the invention, the synthesis route for Maraviroc is as follows.

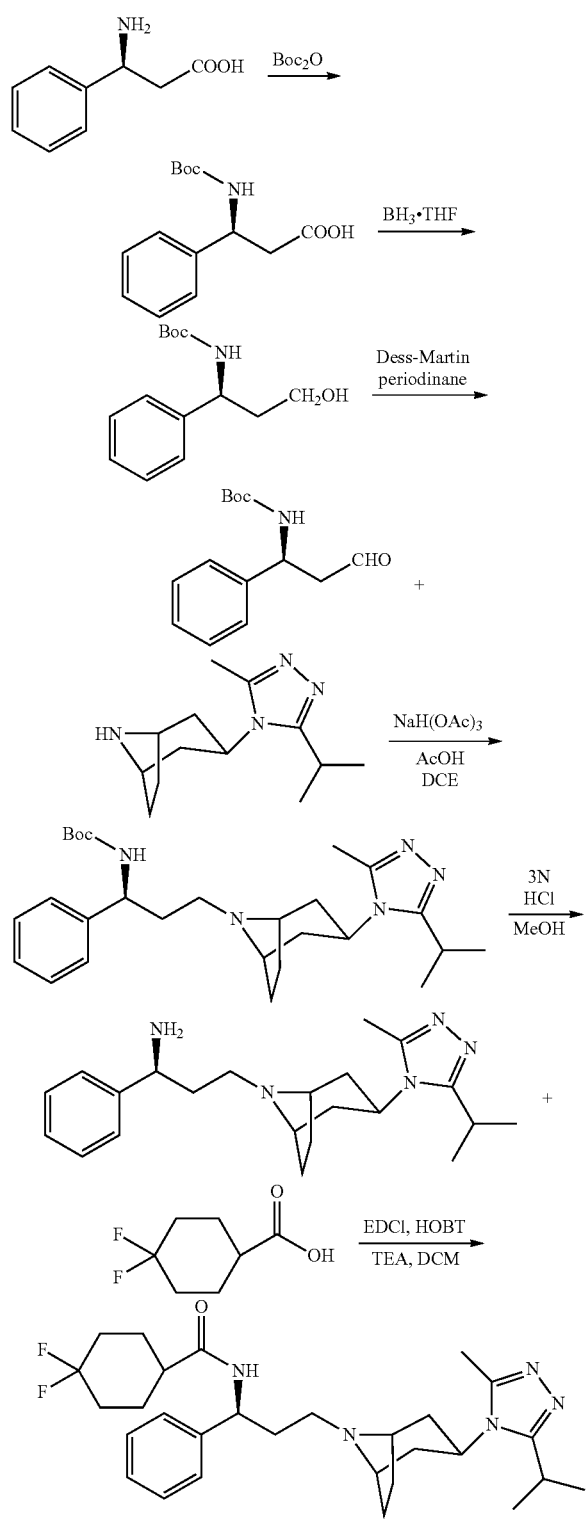

unless otherwise stated, the disclosed features are only general examples of equal or similar features.

The beneficial effects of the invention are as follows.

(1) A cheap 2-methylproline which has a wide range of sources is used as raw material.

(2) The nickel chelate is used to induce the asymmetric resolution of chiral amino acids to construct a chiral center, which improves the optical purity of the product.

(3) The present invention optimizes the synthetic route of Maraviroc, and the synthesis process is mild and easy to be controlled.

(4) The newly designed proline type chiral ligand is resistant to acid and high temperature and has stable structure. A quantitative recover and recycle can be realized while hydrolyzing the chelate, thereby saving synthesis cost.

The invention is further illustrated below in conjunction with specific examples. It is to be understood that the examples are used to illuminate the invention and not intended to limit the scope of the invention. The experimental methods in the following examples which do not contain the specific conditions are usually carried out according to conventional conditions or according to the conditions recommended by the manufacturer.

Unless otherwise defined, all professional and scientific terms used herein have the same meaning known as those skilled in the art. In addition, any methods and materials similar or equivalent to those described may be employed in the methods of the invention. The preferred embodiments and materials described herein are for illustrative purposes only.

Example 1 Preparation of (R)-1-(tert-butoxycarbonyl)-2-methylproline 10 g of (R)-2-methylproline (77.42 mmol) and 14.30 g of TMAH $(CH_3)_4NOH \cdot 5H_2O$ (77.42 mmol) were added into a 250 ml three-necked flask, dissolved in 200 mL of acetonitrile and stirred at 20-40° C. Di-tert-butyl dicarbonate (116.13 mmol) was added and stirred for 3-5 days.

After completion of the reaction, water and ethyl acetate were added, and the aqueous layer was extracted three times with EtOAc. The combined organic lays were washed with saturated sodium bicarbonate solution and then dried over anhydrous magnesium sulfate. 16.5 g of (R)-1-(tert-butoxycarbonyl)-2-methylproline in a yield of 93% was obtained by removing ethyl acetate under normal pressure.

$^1$H NMR (500 MHz, DMSO-$d_6$) δ 12.38 (s, 1H), 3.43-3.34 (m, 2H), 2.14-2.00 (m, 1H), 1.93-1.76 (m, 3H), 1.41 (d, J=2.4 Hz, 3H), 1.37 (d, J=19.8 Hz, 9H).

$^{13}$C NMR (125 MHz, DMSO-$d_6$) δ 176.4, 153.4, 79.2, 64.7, 48.1, 39.1, 28.4, 23.5, 22.7.

Example 2 Preparation of tert-butyl-(R)-2-((2-benzoyl-4-chlorophenyl)carbamoyl)-2-methylprolinamide 10 g of (R)-1-(tert-butoxycarbonyl)-2-methylproline (43.62 mmol), 10.33 mL of 1-methylimidazole (130.85 mmol) and a catalytic amount of DMAP were added into a 250 ml three-necked flask and dissolved in 200 ml of dichloromethane. After 15-45 min, 11.12 g of (2-amino-5-chlorophenyl)benzophenone (47.98 mmol) was added in the reaction mixture system and the reaction temperature was controlled at 0-10° C. The mixture was stirred for 12-36 h and then water and dichloromethane were added. The aqueous phase was extracted three times with dichloromethane. The combined organic lays were washed with saturated The above-mentioned features in the present invention, or the features mentioned in the examples, may be arbitrarily combined. All of the features disclosed in the present specification can be used in combination with any of the compositions, and the various features disclosed in the specification can be substituted with any alternative features that provide the same, equal or similar purpose. Therefore, sodium bicarbonate solution and then dried over anhydrous magnesium sulfate. 12 g of tert-butyl-(R)-2-((2-benzoyl-4-chlorophenyl)carbamoyl)-2-methylprolinamide (yield 62%) was obtained by removing dichloromethane under normal pressure.

$^1$H NMR (500 MHz, DMSO-d$_6$) δ 10.39 (s, 1H), 8.02 (d, J=8.9 Hz, 1H), 7.76-7.71 (m, 1H), 7.70-7.63 (m, 3H), 7.54 (t, J=7.7 Hz, 2H), 7.46 (d, J=2.6 Hz, 1H), 3.64-3.50 (m, 1H), 3.42-3.38 (m, 1H), 1.79-1.62 (m, 4H), 1.39 (s, 3H), 1.26 (d, J=39.3 Hz, 9H).

Example 3 Preparation of (R)-2-((2-benzoyl-4-chlorophenyl)carbamoyl)-2-methylprolinamide 8.5 g of tert-butyl (R)-2-((2-benzoyl-4-chlorophenyl)carbamoyl)-2-methylprolinamide (19.19 mmol) was dissolved in 20 ml of dichloromethane and 20 ml of trifluoroacetic acid was added and stirred for 6-8 h at 20-40° C. The mixture was evaporated to obtain 6.5 g of target product, (R)-2-((2-benzoyl-4-chlorophenyl)carbamoyl)-2-methylprolinamide (yield 98%).

$^1$H NMR (500 MHz, CDCl$_3$) δ 11.95 (s, 1H), 8.63 (d, J=8.9 Hz, 1H), 7.78-7.72 (m, 2H), 7.66-7.56 (m, 1H), 7.54-7.44 (m, 4H), 3.16 (dt, J=10.6, 6.4 Hz, 1H), 3.00-2.91 (m, 1H), 2.35-2.24 (m, 1H), 1.82-1.63 (m, 4H), 1.46 (s, 3H).

$^{13}$C NMR (125 MHz, CDCl$_3$) δ 196.9, 177.4, 137.9, 137.9, 133.2, 132.9, 131.8, 130.1, 128.5, 127.3, 126.7, 122.8, 67.4, 47.2, 38.1, 26.5, 25.8.

Example 4 Preparation of (R)—N-(2-benzoyl-4-chlorophenyl)-1-ethyl-2-methylpyrrolyl-2-carboxamide 5 g of (R)-2-((2-benzoyl-4-chlorophenyl)carbamoyl)-2-methylprolinamide (14.58 mmol) and 16.04 mmol of acetaldehyde were dissolved in dichloromethane. A catalytic amount of acetic acid was added and reacted at 10-30° C. for 15 min-1 h, and then water and dichloromethane were added. The aqueous phase was extracted three times with dichloromethane. Then the combined organic lays were washed with saturated sodium bicarbonate solution, dried over anhydrous magnesium sulfate and evaporated under normal pressure to remove dichloromethane to obtain 10 g of (R)—N-(2-benzoyl-4-chlorophenyl)-1-ethyl-2-methylpyrrolyl-2-carboxamide in a yield of 95%.

mp 87-88° C. [α]$_{20}^D$=+143.5 (c=0.108, CHCl$_3$).

$^1$H NMR (500 MHz, CDCl$_3$) δ 11.62 (s, 1H), 8.60 (d, J=9.0 Hz, 1H), 7.75 (d, J=7.2 Hz, 2H), 7.61 (t, J=7.4 Hz, 1H), 7.49 (t, J=7.6 Hz, 3H), 7.42 (d, J=2.5 Hz, 1H), 3.39-3.32 (m, 1H), 2.57-2.45 (m, 1H), 2.43-2.32 (m, 2H), 2.14-2.03 (m, 1H), 1.78-1.67 (m, 3H), 1.25 (s, 3H), 1.10 (t, J=7.2 Hz, 3H).

$^{13}$C NMR (125 MHz, CDCl$_3$) δ 196.5, 177.5, 137.9, 137.9, 133.1, 133.0, 131.5, 130.1, 128.6, 127.2, 127.1, 122.9, 68.4, 51.0, 43.9, 40.5, 22.8, 16.2, 14.5.

LRMS (ESI+APCI) m/z: 371.1, HRMS (ESI) m/z: found: 371.1527, calcd 371.1521 for C$_{21}$H$_{23}$ClN$_2$O$_2$$^+$ [M+H]$^+$.

Example 5 Preparation of (R)—N-(2-benzoyl-4-chlorophenyl)-1-(3,4-dichlorobenzyl)-2-methylpyrrolyl-2-carboxamide The compound was prepared according to example 4.

$^1$H NMR (400 MHz, DMSO-d$_6$) δ 10.04 (s, 1H), 8.60 (d, J=7.5 Hz, 1H), 7.81 (d, J=2.0 Hz, 1H), 7.66-7.43 (m, 8H), 6.98 (ddt, J=7.5, 2.2, 1.1 Hz, 1H), 3.74 (dt, J=12.5, 1.1 Hz, 1H), 3.58 (dt, J=12.4, 1.1 Hz, 1H), 3.21 (ddd, J=9.6, 8.2, 1.4 Hz, 1H), 2.42-2.28 (m, 2H), 2.04-1.82 (m, 2H), 1.75 (dt, J=13.1, 7.0 Hz, 1H), 1.48 (s, 3H).

LCMS (ESI+APCI) m/z: 501.83

Example 6 Preparation of (R)—N-(2-benzoyl-4-chlorophenyl)-1-benzyl-2-methylpyrrolyl-2-carboxamide The compound was prepared according to example 4.

$^1$H NMR (400 MHz, DMSO-d$_6$) δ 10.04 (s, 1H), 8.62 (d, J=7.5 Hz, 1H), 7.69-7.56 (m, 5H), 7.60-7.46 (m, 2H), 7.31 (s, 3H), 7.37-7.22 (m, 2H), 3.67 (d, J=12.3 Hz, 1H), 3.57 (d, J=12.4 Hz, 1H), 3.10 (ddd, J=9.6, 6.9, 2.8 Hz, 1H), 2.35-2.21 (m, 2H), 1.89-1.75 (m, 2H), 1.78-1.67 (m, 1H), 1.09 (s, 3H).

LCMS (ESI+APCI) m/z: 432.95

Example 7 Preparation of (R)—N-(2-benzoyl-4-chlorophenyl)-1-phenylethyl-2-methylpyrrolyl-2-carboxamide The compound was prepared according to example 4.

$^1$H NMR (400 MHz, DMSO-d$_6$) δ 10.04 (s, 1H), 8.48 (d, J=7.5 Hz, 1H), 7.80 (d, J=2.1 Hz, 1H), 7.66-7.55 (m, 4H), 7.56-7.46 (m, 2H), 7.25 (s, 2H), 7.31-7.14 (m, 3H), 3.09 (ddd, J=10.3, 8.2, 1.6 Hz, 1H), 2.90 (td, J=12.1, 1.5 Hz, 1H), 2.62 (td, J=12.3, 1.6 Hz, 1H), 2.50-2.34 (m, 2H), 2.18-2.05 (m, 2H), 1.96-1.74 (m, 3H), 1.42 (s, 3H).

LCMS (ESI+APCI) m/z: 446.98

Example 8 Preparation of (S)—N-(2-benzoyl-4-chlorophenyl)-1-(3,4-dichlorobenzyl)-2-fluoropyrrolyl-2-carboxamide The compound was prepared according to example 4.

$^1$H NMR (400 MHz, DMSO-d$_6$) δ 10.04 (s, 1H), 8.61 (d, J=7.5 Hz, 1H), 7.81 (d, J=2.1 Hz, 1H), 7.66-7.55 (m, 4H), 7.55-7.46 (m, 3H), 7.34 (q, J=1.2 Hz, 1H), 7.06-6.98 (m, 1H), 3.80 (d, J=12.6 Hz, 1H), 3.66-3.58 (m, 1H), 2.99 (dd, J=9.1, 6.0 Hz, 1H), 2.56-2.38 (m, 1H), 2.24 (ddd, J=11.6, 9.1, 5.1 Hz, 1H), 2.20-2.07 (m, 1H), 2.12-1.95 (m, 1H), 1.89-1.75 (m, 1H).

LCMS (ESI+APCI) m/z: 505.80

Example 9 Preparation of (S)—N-(2-benzoyl-4-chlorophenyl)-1-(3,4-dichlorobenzyl)-2-chloropyrrolyl-2-carboxamide The compound was prepared according to example 4.

$^1$H NMR (400 MHz, DMSO-d$_6$) δ 10.04 (s, 1H), 8.53 (d, J=7.5 Hz, 1H), 7.80 (d, J=2.1 Hz, 1H), 7.60 (dddd, J=8.4, 7.1, 4.9, 1.9 Hz, 5H), 7.55-7.46 (m, 3H), 7.03-6.95 (m, 1H), 3.78 (d, J=12.3 Hz, 1H), 3.69 (d, J=12.5 Hz, 1H), 3.44 (td, J=9.0, 1.3 Hz, 1H), 2.74-2.62 (m, 1H), 2.37 (q, J=8.6 Hz, 1H), 2.21-2.03 (m, 2H), 2.06-1.91 (m, 1H).

LCMS (ESI+APCI) m/z: 522.25

Example 10 Preparation of (S)—N-(2-benzoyl-4-chlorophenyl)-1-(3,4-dichlorobenzyl)-2-bromopyrrolyl-2-carboxamide The compound was prepared according to example 4.

$^1$H NMR (400 MHz, DMSO-d$_6$) δ 10.04 (s, 1H), 8.61 (d, J=7.5 Hz, 1H), 7.82 (d, J=2.0 Hz, 1H), 7.66-7.55 (m, 4H), 7.55-7.46 (m, 3H), 7.40 (q, J=1.2 Hz, 1H), 6.87-6.79 (m, 1H), 4.55 (d, J=12.4 Hz, 1H), 3.65 (d, J=12.3 Hz, 1H), 3.16

(dt, J=13.7, 7.1 Hz, 1H), 3.04-2.95 (m, 1H), 2.28-2.08 (m, 2H), 2.09-1.93 (m, 1H), 1.41-1.27 (m, 1H).
LCMS (ESI+APCI) m/z: 566.70

Example 11 Preparation of (S)—N-(2-benzoyl-4-chlorophenyl)-1-(3,4-dichlorobenzyl)-2-iodopyrrolyl-2-carboxamide The compound was prepared according to example 4.
$^1$H NMR (400 MHz, DMSO-d$_6$) δ 10.04 (s, 1H), 8.62 (d, J=7.4 Hz, 1H), 7.82 (d, J=2.0 Hz, 1H), 7.66-7.55 (m, 4H), 7.55-7.46 (m, 3H), 7.40 (q, J=1.2 Hz, 1H), 6.89-6.81 (m, 1H), 4.55 (d, J=12.4 Hz, 1H), 3.74-3.66 (m, 1H), 3.33 (dt, J=13.7, 7.0 Hz, 1H), 3.04-2.95 (m, 1H), 2.40 (dt, J=13.6, 7.1 Hz, 1H), 2.12 (ddd, J=12.1, 9.3, 4.9 Hz, 1H), 2.07-1.91 (m, 1H), 1.34-1.21 (m, 1H).
LCMS (ESI+APCI) m/z: 613.70

Example 12 Preparation of (S)—N-(2-benzoyl-4-chlorophenyl)-1-(3,4-dichlorobenzyl)-2-cyanopyrrolylpyrrolyl-2-carboxamide The compound was prepared according to example 4.
$^1$H NMR (400 MHz, DMSO-d$_6$) δ 10.04 (s, 1H), 8.56 (d, J=7.5 Hz, 1H), 7.82 (d, J=2.0 Hz, 1H), 7.66-7.55 (m, 4H), 7.60-7.46 (m, 4H), 7.03-6.95 (m, 1H), 3.79 (d, J=12.3 Hz, 1H), 3.69 (d, J=12.5 Hz, 1H), 3.35 (ddd, J=9.5, 8.1, 1.4 Hz, 1H), 2.71 (dt, J=13.0, 7.0 Hz, 1H), 2.61-2.49 (m, 1H), 2.33-2.01 (m, 3H).
LCMS (ESI+APCI) m/z: 512.82

Example 13 Preparation of (R)—N-(2-benzoyl-4-chlorophenyl)-1-(3,4-dichlorobenzyl)-2-ethylpyrrolyl-2-carboxamide The compound was prepared according to example 4.
$^1$H NMR (400 MHz, DMSO-d$_6$) δ 10.04 (s, 1H), 8.59 (d, J=7.5 Hz, 1H), 7.81 (d, J=2.0 Hz, 1H), 7.66-7.55 (m, 4H), 7.55-7.44 (m, 4H), 6.99 (dq, J=7.6, 1.3 Hz, 1H), 3.73 (d, J=12.6 Hz, 1H), 3.60 (d, J=12.7 Hz, 1H), 3.21 (ddd, J=10.0, 8.3, 1.9 Hz, 1H), 2.39-2.24 (m, 3H), 2.10 (dq, J=12.5, 7.9 Hz, 1H), 2.03-1.83 (m, 2H), 1.80 (dt, J=13.2, 6.8 Hz, 1H), 0.65 (t, J=7.9 Hz, 3H).
LCMS (ESI+APCI) m/z: 515.86

Example 14 Preparation of (R)—N-(2-benzoyl-4-chlorophenyl)-1-(3,4-dichlorobenzyl)-2-trifluoromethylpyrrolyl-2-carboxamide The compound was prepared according to example 4.
$^1$H NMR (400 MHz, DMSO-d$_6$) δ 10.04 (s, 1H), 8.59 (d, J=7.5 Hz, 1H), 7.80 (d, J=2.0 Hz, 1H), 7.66-7.55 (m, 4H), 7.55-7.46 (m, 4H), 7.02 (dq, J=7.6, 1.1 Hz, 1H), 3.77 (d, J=12.3 Hz, 1H), 3.66 (d, J=12.1 Hz, 1H), 3.38-3.29 (m, 1H), 2.61-2.42 (m, 2H), 2.19-2.04 (m, 1H), 2.09-1.95 (m, 2H).
LCMS (ESI+APCI) m/z: 555.80

Example 15 Preparation of (S)—N-(2-benzoyl-4-chlorophenyl)-1-(3,4-dichlorobenzyl)-2-isopropylpyrrolyl-2-carboxamide The compound was prepared according to example 4.
$^1$H NMR (400 MHz, DMSO-d$_6$) δ 10.04 (s, 1H), 8.70 (d, J=7.5 Hz, 1H), 7.87 (d, J=2.1 Hz, 1H), 7.66-7.58 (m, 2H), 7.62-7.57 (m, 1H), 7.61-7.46 (m, 3H), 7.43 (dd, J=2.1, 1.1 Hz, 1H), 6.81 (ddd, J=7.5, 2.2, 1.2 Hz, 1H), 3.81 (dd, J=12.3, 1.1 Hz, 1H), 3.11 (dt, J=12.3, 1.1 Hz, 1H), 2.93 (ddd, J=11.8, 9.4, 4.9 Hz, 1H), 2.34 (dd, J=9.5, 6.4 Hz, 1H), 2.18-1.97 (m, 3H), 1.86-1.73 (m, 1H), 1.77-1.59 (m, 1H), 0.96 (d, J=6.8 Hz, 6H).
LCMS (ESI+APCI) m/z: 529.89

Example 16 Preparation of (S)—N-(2-benzoyl-4-chlorophenyl)-1-(3,4-dichlorobenzyl)-2-tert-butylpyrrolyl-2-carboxamide The compound was prepared according to example 4.
$^1$H NMR (400 MHz, DMSO-d$_6$) δ 10.04 (s, 1H), 8.47 (d, J=7.5 Hz, 1H), 7.74 (d, J=2.1 Hz, 1H), 7.66-7.46 (m, 8H), 6.97 (ddt, J=7.6, 2.1, 1.2 Hz, 1H), 3.63 (dt, J=12.5, 1.1 Hz, 1H), 3.35 (dt, J=12.5, 1.1 Hz, 1H), 3.16 (td, J=9.2, 1.8 Hz, 1H), 2.22 (td, J=9.3, 6.9 Hz, 1H), 2.20-2.05 (m, 1H), 1.90 (ddq, J=20.5, 9.4, 6.9 Hz, 2H), 1.63 (ddtd, J=14.1, 8.7, 6.7, 2.9 Hz, 1H), 0.92 (s, 9H).
LCMS (ESI+APCI) m/z: 543.91

Example 17 Preparation of (S)—N-(2-benzoyl-4-chlorophenyl)-1-(3,4-dichlorobenzyl)-2-benzylpyrrolyl-2-carboxamide The compound was prepared according to example 4.
$^1$H NMR (400 MHz, DMSO-d$_6$) δ 10.04 (s, 1H), 8.59 (d, J=7.5 Hz, 1H), 7.85 (d, J=2.0 Hz, 1H), 7.66-7.45 (m, 8H), 7.29-7.14 (m, 3H), 7.07 (ddd, J=7.5, 2.4, 1.2 Hz, 2H), 7.03-6.95 (m, 1H), 3.73 (d, J=12.5 Hz, 1H), 3.61 (d, J=12.3 Hz, 1H), 3.43-3.35 (m, 1H), 3.27 (ddd, J=9.4, 8.0, 2.9 Hz, 1H), 3.13 (d, J=12.2 Hz, 1H), 2.42-2.30 (m, 2H), 2.13-1.95 (m, 2H), 1.87 (dt, J=12.9, 7.0 Hz, 1H).
LCMS (ESI+APCI) m/z: 577.93

Example 18 Preparation of (S)—N-(2-benzoyl-4-chlorophenyl)-1-(3,4-dichlorobenzyl)-2-methylpyrrolyl-2-carboxamide The compound was prepared according to example 4.
$^1$H NMR (400 MHz, DMSO-d$_6$) δ 10.04 (s, 1H), 8.55 (d, J=7.5 Hz, 1H), 7.76 (d, J=2.0 Hz, 1H), 7.66-7.55 (m, 4H), 7.56-7.46 (m, 3H), 7.44 (ddd, J=7.3, 2.1, 1.1 Hz, 1H), 7.34 (dd, J=2.2, 1.3 Hz, 1H), 3.90 (dt, J=12.4, 1.1 Hz, 1H), 3.73 (dt, J=12.4, 1.1 Hz, 1H), 3.10-3.00 (m, 1H), 2.51-2.35 (m, 2H), 1.77-1.63 (m, 3H), 1.19 (s, 3H).
LCMS (ESI+APCI) m/z: 501.83

Example 19 Preparation of (S)—N-(2-benzoyl-4-chlorophenyl)-1-benzyl-2-methylpyrrolyl-2-carboxamide The compound was prepared according to example 4.
$^1$H NMR (400 MHz, DMSO-d$_6$) δ 10.04 (s, 1H), 8.62 (d, J=7.4 Hz, 1H), 7.77 (d, J=1.9 Hz, 1H), 7.66-7.55 (m, 4H), 7.56-7.46 (m, 2H), 7.31 (s, 3H), 7.37-7.22 (m, 2H), 4.02 (d, J=12.3 Hz, 1H), 3.58 (d, J=12.4 Hz, 1H), 2.97-2.86 (m, 1H), 2.47-2.31 (m, 2H), 1.78-1.63 (m, 3H), 1.33 (s, 3H).
LCMS (ESI+APCI) m/z: 432.95

Example 20 Preparation of (S)—N-(2-benzoyl-4-chlorophenyl)-1-phenylethyl-2-methylpyrrolyl-2-carboxamide The compound was prepared according to example 4.
$^1$H NMR (400 MHz, DMSO-d$_6$) δ 10.04 (s, 1H), 8.63 (d, J=7.5 Hz, 1H), 7.82 (d, J=1.9 Hz, 1H), 7.66-7.58 (m, 2H), 7.62-7.46 (m, 3H), 7.25 (s, 2H), 7.31-7.14 (m, 3H), 3.08 (dt, J=9.5, 7.0 Hz, 1H), 2.85-2.76 (m, 2H), 2.69 (td, J=7.3, 1.3

Hz, 2H), 2.48 (dt, J=9.5, 7.1 Hz, 1H), 2.09 (dt, J=13.2, 7.1 Hz, 1H), 1.83 (ddd, J=13.1, 7.5, 6.6 Hz, 1H), 1.69 (p, J=7.0 Hz, 2H), 1.33 (s, 3H).
LCMS (ESI+APCI) m/z: 446.98

Example 21 Preparation of (S)—N-(2-benzoyl-4-chlorophenyl)-1-ethyl-2-methyl pyrrolyl-2-carboxamide The compound was prepared according to example 4.
$^1$H NMR (400 MHz, DMSO-$d_6$) δ 10.04 (s, 1H), 8.64 (d, J=7.5 Hz, 1H), 7.78 (d, J=1.9 Hz, 1H), 7.66-7.55 (m, 4H), 7.56-7.46 (m, 2H), 3.03 (dt, J=9.5, 7.0 Hz, 1H), 2.53-2.34 (m, 2H), 2.22-2.05 (m, 2H), 1.81 (ddd, J=13.0, 7.6, 6.5 Hz, 1H), 1.69 (p, J=7.1 Hz, 2H), 1.30 (s, 3H), 1.04 (t, J=8.0 Hz, 3H).
LCMS (ESI+APCI) m/z: 370.88

Example 22 Preparation of (R)—N-(2-benzoyl-4-chlorophenyl)-1-(4-chlorobenzyl)-2-methylpyrrolyl-2-carboxamide The compound was prepared according to example 4.
$^1$H NMR (400 MHz, DMSO-$d_6$) δ 10.04 (s, 1H), 8.55 (d, J=7.5 Hz, 1H), 7.76 (d, J=1.9 Hz, 1H), 7.66-7.55 (m, 4H), 7.56-7.46 (m, 2H), 7.37 (d, J=1.4 Hz, 4H), 3.86 (d, J=12.3 Hz, 1H), 3.70 (d, J=12.5 Hz, 1H), 3.06 (ddd, J=9.4, 6.2, 3.0 Hz, 1H), 2.50-2.35 (m, 2H), 1.87-1.73 (m, 2H), 1.76-1.64 (m, 1H), 1.20 (s, 3H).
LCMS (ESI+APCI) m/z: 467.39

Example 23 Preparation of (R)—N-(2-benzoyl-4-chlorophenyl)-1-(3-chlorobenzyl)-2-methylpyrrolyl-2-carboxamide The compound was prepared according to example 4.
$^1$H NMR (400 MHz, DMSO-$d_6$) δ 10.04 (s, 1H), 8.67 (d, J=7.5 Hz, 1H), 7.69 (d, J=2.0 Hz, 1H), 7.66-7.55 (m, 4H), 7.60-7.46 (m, 2H), 7.40-7.30 (m, 3H), 7.00 (tdd, J=4.8, 2.2, 1.1 Hz, 1H), 3.67 (dd, J=12.4, 1.1 Hz, 1H), 3.49 (dd, J=12.5, 1.2 Hz, 1H), 3.07 (ddd, J=9.4, 7.5, 1.9 Hz, 1H), 2.39-2.27 (m, 2H), 2.29-2.14 (m, 1H), 1.90-1.71 (m, 3H), 1.13 (s, 3H).
LCMS (ESI+APCI) m/z: 467.39

Example 24 Preparation of (R)—N-(2-benzoyl-4-chlorophenyl)-1-(2-chlorobenzyl)-2-methylpyrrolyl-2-carboxamide The compound was prepared according to example 4.
$^1$H NMR (400 MHz, DMSO-$d_6$) δ 10.04 (s, 1H), 8.62 (d, J=7.5 Hz, 1H), 7.68-7.55 (m, 5H), 7.56-7.46 (m, 2H), 7.26 (dd, J=4.5, 2.2 Hz, 2H), 7.15-7.05 (m, 2H), 3.98 (d, J=12.4 Hz, 1H), 3.49 (d, J=12.4 Hz, 1H), 3.11 (ddd, J=9.5, 6.4, 3.2 Hz, 1H), 2.36-2.22 (m, 2H), 1.90-1.76 (m, 2H), 1.73 (ddd, J=12.6, 7.5, 6.2 Hz, 1H), 1.08 (s, 3H).
LCMS (ESI+APCI) m/z: 467.39

Example 25 Preparation of (R)—N-(2-benzoyl-4-chlorophenyl)-1-(3-fluorobenzyl)-2-methylpyrrolyl-2-carboxamide The compound was prepared according to example 4.
$^1$H NMR (400 MHz, DMSO-$d_6$) δ 10.04 (s, 1H), 8.62 (d, J=7.5 Hz, 1H), 7.79 (d, J=2.0 Hz, 1H), 7.66-7.55 (m, 4H), 7.60-7.46 (m, 2H), 7.18-7.06 (m, 2H), 7.02 (ddt, J=9.2, 7.3, 2.0 Hz, 2H), 3.74 (dt, J=12.3, 1.0 Hz, 1H), 3.64-3.56 (m, 1H), 3.20 (ddd, J=9.6, 7.8, 1.8 Hz, 1H), 2.41-2.28 (m, 2H), 2.00-1.80 (m, 2H), 1.77 (dt, J=12.8, 7.0 Hz, 1H), 1.49 (s, 3H).
LCMS (ESI+APCI) m/z: 450.94

Example 26 Preparation of (R)—N-(2-benzoyl-4-chlorophenyl)-1-(4-fluorobenzyl)-2-methylpyrrolyl-2-carboxamide The compound was prepared according to example 4.
$^1$H NMR (400 MHz, DMSO-$d_6$) δ 10.04 (s, 1H), 8.66 (d, J=7.5 Hz, 1H), 7.70 (d, J=2.1 Hz, 1H), 7.66-7.46 (m, 6H), 7.32 (ddd, J=7.6, 4.2, 1.2 Hz, 2H), 7.17-7.07 (m, 2H), 3.84 (dd, J=12.3, 1.1 Hz, 1H), 3.22 (dt, J=12.4, 1.2 Hz, 1H), 2.94 (td, J=9.5, 1.9 Hz, 1H), 2.29 (ddq, J=12.8, 9.6, 7.2 Hz, 1H), 2.21-2.01 (m, 2H), 1.71 (dtd, J=13.1, 8.8, 6.9, 1.9 Hz, 1H), 1.57 (dt, J=13.1, 7.1 Hz, 1H), 1.01 (s, 3H).
LCMS (ESI+APCI) m/z: 450.94

Example 27 Preparation of (R)—N-(2-benzoyl-4-chlorophenyl)-1-(2-fluorobenzyl)-2-methylpyrrolyl-2-carboxamide The compound was prepared according to example 4.
$^1$H NMR (400 MHz, DMSO-$d_6$) δ 10.04 (s, 1H), 8.66 (d, J=7.5 Hz, 1H), 7.82 (d, J=2.0 Hz, 1H), 7.66-7.46 (m, 7H), 7.36 (tdd, J=7.4, 5.6, 1.9 Hz, 1H), 7.22 (ddd, J=9.3, 7.5, 2.1 Hz, 1H), 7.02 (td, J=7.5, 2.1 Hz, 1H), 4.39 (dd, J=12.5, 1.0 Hz, 1H), 3.72 (dd, J=12.3, 1.0 Hz, 1H), 2.96 (ddd, J=11.7, 9.5, 5.7 Hz, 1H), 2.53 (dt, J=13.1, 7.0 Hz, 1H), 2.24-2.15 (m, 1H), 1.99-1.85 (m, 1H), 1.62 (dt, J=13.3, 7.0 Hz, 1H), 1.37 (s, 3H), 1.34 (ddt, J=13.4, 11.6, 6.8 Hz, 1H).
LCMS (ESI+APCI) m/z: 450.94

Example 28 Preparation of (R)—N-(2-benzoyl-4-chlorophenyl)-1-(3-methylbenzyl)-2-methylpyrrolyl-2-carboxamide The compound was prepared according to example 4.
$^1$H NMR (500 MHz, CDCl$_3$) δ 9.82 (s, 1H), 7.80 (s, 1H), 7.68-7.59 (m, 3H), 7.56 (s, 1H), 7.46 (s, 1H), 7.42-7.35 (m, 2H), 7.21 (d, J=2.9 Hz, 2H), 7.12-7.01 (m, 2H), 4.13 (s, 1H), 3.07 (s, 1H), 2.76 (s, 1H), 2.40 (s, 1H), 2.37-2.30 (m, 3H), 2.17 (s, 1H), 1.83 (s, 1H), 1.76 (s, 1H), 1.67 (s, 1H), 1.66-1.63 (m, 3H).

Example 29 Preparation of (R)—N-(2-benzoyl-4-chlorophenyl)-1-(4-methylbenzyl)-2-methylpyrrolyl-2-carboxamide The compound was prepared according to example 4.
$^1$H NMR (500 MHz, CDCl3) δ 8.91 (s, 1H), 7.87 (s, 1H), 7.76-7.70 (m, 2H), 7.60 (d, J=14.8 Hz, 2H), 7.50 (s, 1H), 7.45-7.37 (m, 2H), 7.15-7.09 (m, 4H), 4.00 (s, 1H), 2.88 (s, 1H), 2.79 (s, 1H), 2.34-2.29 (m, 3H), 2.24 (d, J=5.4 Hz, 2H), 1.83 (s, 1H), 1.76 (s, 1H), 1.67 (s, 1H), 1.63-1.59 (m, 3H).

Example 30 Preparation of (R)—N-(2-benzoyl-4-chlorophenyl)-1-(2-methylbenzyl)-2-methylpyrrolyl-2-carboxamide The compound was prepared according to example 4.
$^1$H NMR (500 MHz, CDCl3) δ 7.74 (d, J=8.8 Hz, 2H), 7.69-7.62 (m, 2H), 7.46 (d, J=6.6 Hz, 2H), 7.43-7.37 (m, 2H), 7.27 (s, 1H), 7.17 (t, J=6.3 Hz, 3H), 3.45 (d, J=5.0 Hz, 2H), 2.89 (s, 1H), 2.70 (s, 1H), 2.32-2.23 (m, 3H), 2.09 (s, 1H), 1.79 (d, J=13.1 Hz, 2H), 1.68 (s, 1H), 1.54-1.46 (m, 3H).

Example 31 Preparation of (R)—N-(2-benzoyl-4-chlorophenyl)-1-(3,4-difluorobenzyl)-2-methylpyrrolyl-2-carboxamide The compound was prepared according to example 4. $^1$H NMR (500 MHz, CDCl3) δ 9.50 (s, 1H), 7.81 (s, 1H), 7.73 (s, 1H), 7.70-7.66 (m, 2H), 7.56 (s, 1H), 7.46 (s, 1H), 7.42-7.37 (m, 2H), 7.02 (d, J=7.0 Hz, 2H), 6.88 (s, 1H), 3.59 (s, 1H), 3.41 (s, 1H), 2.94 (s, 1H), 2.79 (s, 1H), 2.09 (s, 1H), 1.82 (s, 1H), 1.76 (s, 1H), 1.67 (s, 1H), 1.58-1.43 (m, 3H).

Example 32 Preparation of (R)—N-(2-benzoyl-4-chlorophenyl)-1-(3,4-dimethyl benzyl)-2-methylpyrrolyl-2-carboxamide The compound was prepared according to example 4. $^1$H NMR (500 MHz, CDCl3) δ 9.85 (s, 1H), 7.80 (s, 1H), 7.67-7.61 (m, 3H), 7.56 (s, 1H), 7.46 (s, 1H), 7.42-7.36 (m, 2H), 7.16 (s, 1H), 7.09 (s, 1H), 7.03 (s, 1H), 4.12 (s, 1H), 3.05 (s, 1H), 2.75 (s, 1H), 2.39 (s, 1H), 2.36-2.34 (m, 3H), 2.33-2.31 (m, 3H), 2.18 (s, 1H), 1.83 (s, 1H), 1.76 (s, 1H), 1.67 (s, 1H), 1.65-1.64 (m, 3H).

Example 33 Preparation of (R)—N-(2-benzoyl-4-chlorophenyl)-1-(2,4-dichlorobenzyl)-2-methylpyrrolyl-2-carboxamide The compound was prepared according to example 4. $^1$H NMR (500 MHz, CDCl3) δ 7.88 (s, 1H), 7.74-7.67 (m, 2H), 7.56 (s, 1H), 7.47 (s, 1H), 7.44-7.38 (m, 3H), 7.36 (s, 1H), 7.21 (d, J=10.7 Hz, 2H), 6.09 (s, 1H), 3.40 (s, 1H), 3.25 (s, 1H), 2.81 (s, 1H), 2.23 (d, J=8.9 Hz, 2H), 1.78 (d, J=16.1 Hz, 2H), 1.67 (s, 1H), 1.42-1.36 (m, 3H).

Example 34 Preparation of (R)—N-(2-benzoyl-4-chlorophenyl)-1-(3,5-difluorobenzyl)-2-methylpyrrolyl-2-carboxamide The compound was prepared according to example 4. $^1$H NMR (500 MHz, CDCl3) δ 9.57 (s, 1H), 7.81 (s, 1H), 7.73 (s, 1H), 7.71-7.65 (m, 2H), 7.56 (s, 1H), 7.46 (s, 1H), 7.43-7.37 (m, 2H), 6.79-6.71 (m, 3H), 3.63 (s, 1H), 3.39 (s, 1H), 2.93 (s, 1H), 2.86 (s, 1H), 2.09 (s, 1H), 1.83 (s, 1H), 1.76 (s, 1H), 1.67 (s, 1H), 1.53-1.44 (m, 3H).

Example 35 Preparation of (R)—N-(2-benzoyl-4-chlorophenyl)-1-(2,3-difluorobenzyl)-2-methylpyrrolyl-2-carboxamide The compound was prepared according to example 4. $^1$H NMR (500 MHz, CDCl$_3$) δ 9.99 (s, 1H), 7.79 (s, 1H), 7.71-7.61 (m, 3H), 7.56 (s, 1H), 7.46 (s, 1H), 7.43-7.36 (m, 2H), 7.09-7.00 (m, 2H), 6.93 (s, 1H), 3.89 (s, 1H), 3.26 (s, 1H), 2.80 (s, 1H), 2.69 (s, 1H), 2.09 (s, 1H), 1.81 (s, 1H), 1.77 (s, 1H), 1.68-1.65 (m, 3H).

Example 36 Preparation of (R)—N-(2-benzoyl-4-chlorophenyl)-1-(2,5-difluorobenzyl)-2-methylpyrrolyl-2-carboxamide The compound was prepared according to example 4. $^1$H NMR (500 MHz, CDCl3) δ 9.94 (s, 1H), 7.79 (s, 1H), 7.72-7.61 (m, 3H), 7.56 (s, 1H), 7.46 (s, 1H), 7.43-7.35 (m, 2H), 7.07 (s, 1H), 7.00 (s, 1H), 6.94 (s, 1H), 3.89 (s, 1H), 3.26 (s, 1H), 2.82 (s, 1H), 2.69 (s, 1H), 2.08 (s, 1H), 1.81 (s, 1H), 1.77 (s, 1H), 1.68-1.66 (m, 3H).

Example 37 Preparation of (R)—N-(2-benzoyl-4-chlorophenyl)-1-(2,6-difluorobenzyl)-2-methylpyrrolyl-2-carboxamide The compound was prepared according to example 4. $^1$H NMR (500 MHz, CDCl$_3$) δ 9.71 (s, 1H), 7.79 (s, 1H), 7.70-7.60 (m, 3H), 7.56 (s, 1H), 7.45 (s, 1H), 7.42-7.34 (m, 2H), 7.18 (s, 1H), 6.82-6.72 (m, 2H), 4.13 (s, 1H), 3.14 (s, 1H), 2.72 (s, 1H), 2.46 (s, 1H), 2.18 (s, 1H), 1.84 (s, 1H), 1.76 (s, 1H), 1.67 (s, 1H), 1.66-1.64 (m, 3H).

Example 38 Preparation of (R)—N-(2-benzoyl-4-chlorophenyl)-1-(2,6-difluoro-4-chlorobenzyl)-2-methylpyrrolyl-2-carboxamide The compound was prepared according to example 4. $^1$H NMR (500 MHz, CDCl$_3$) δ 9.67 (s, 1H), 7.79 (s, 1H), 7.66-7.61 (m, 3H), 7.56 (s, 1H), 7.45 (s, 1H), 7.42-7.35 (m, 2H), 6.96-6.70 (m, 2H), 4.12 (s, 1H), 3.13 (s, 1H), 2.70 (s, 1H), 2.46 (s, 1H), 2.18 (s, 1H), 1.83 (s, 1H), 1.76 (s, 1H), 1.67 (s, 1H), 1.66-1.64 (m, 3H).

Example 39 Preparation of (R)—N-(2-benzoyl-4-chlorophenyl)-1-(2,6-difluorobenzyl)-2-methylpyrrolyl-2-carboxamide The compound was prepared according to example 4. $^1$H NMR (500 MHz, CDCl$_3$) δ 9.71 (s, 1H), 7.79 (s, 1H), 7.70-7.60 (m, 3H), 7.56 (s, 1H), 7.45 (s, 1H), 7.42-7.34 (m, 2H), 7.18 (s, 1H), 6.82-6.72 (m, 2H), 4.13 (s, 1H), 3.14 (s, 1H), 2.72 (s, 1H), 2.46 (s, 1H), 2.18 (s, 1H), 1.84 (s, 1H), 1.76 (s, 1H), 1.67 (s, 1H), 1.66-1.64 (m, 3H).

Example 40 Preparation of (R)—N-(2-benzoyl-4-chlorophenyl)-1-(2,4,6-trimethyl benzyl)-2-methylpyrrolyl-2-carboxamide The compound was prepared according to example 4. $^1$H NMR (500 MHz, CDCl3) δ 7.88 (s, 1H), 7.76-7.65 (m, 2H), 7.56 (s, 1H), 7.47 (s, 1H), 7.43-7.36 (m, 2H), 7.33 (s, 1H), 7.03-6.98 (m, 2H), 5.47 (s, 1H), 3.43 (s, 1H), 3.20 (s, 1H), 2.82 (s, 1H), 2.45-2.30 (m, 9H), 2.20 (d, J=22.6 Hz, 2H), 1.78 (d, J=19.9 Hz, 2H), 1.67 (s, 1H), 1.47-1.26 (m, 3H).

Example 41 Preparation of (R)—N-(2-benzoyl-4-chlorophenyl)-1-(2-fluoro-6-chloro-benzyl)-2-methylpyrrolyl-2-carboxamide The compound was prepared according to example 4. $^1$H NMR (500 MHz, CDCl$_3$) δ 9.81 (s, 1H), 7.80 (s, 1H), 7.69-7.62 (m, 3H), 7.56 (s, 1H), 7.46 (s, 1H), 7.43-7.34 (m, 2H), 7.14 (s, 1H), 7.07 (s, 1H), 6.90 (s, 1H), 4.29 (s, 1H), 3.17 (s, 1H), 2.72 (s, 1H), 2.46 (s, 1H), 2.19 (s, 1H), 1.84 (s, 1H), 1.77 (s, 1H), 1.68 (s, 1H), 1.67-1.65 (m, 3H).

Example 42 Preparation of (R)—N-(2-benzoyl-4-chlorophenyl)-1-(3-cyanobenzyl)-2-methylpyrrolyl-2-carboxamide The compound was prepared according to example 4. $^1$H NMR (500 MHz, CDCl$_3$) δ 7.81 (s, 1H), 7.74-7.66 (m, 3H), 7.60-7.54 (m, 4H), 7.47 (d, J=15.1 Hz, 2H), 7.42-7.37

(m, 2H), 3.70 (s, 1H), 3.19 (s, 1H), 2.90 (s, 1H), 2.70 (s, 1H), 2.09 (s, 1H), 1.78 (d, J=7.3 Hz, 2H), 1.68 (s, 1H), 1.47-1.38 (m, 3H).

Example 43 Preparation of (R)—N-(2-benzoyl-4-chlorophenyl)-1-(4-trifluoromethyl benzyl)-2-methylpyrrolyl-2-carboxamide The compound was prepared according to example 4.
$^1$H NMR (500 MHz, CDCl$_3$) δ 9.74 (s, 1H), 7.80 (s, 1H), 7.66-7.60 (m, 3H), 7.58-7.51 (m, 3H), 7.46 (s, 1H), 7.42-7.36 (m, 2H), 7.25-7.20 (m, 2H), 4.14 (s, 1H), 3.08 (s, 1H), 2.74 (s, 1H), 2.41 (s, 1H), 2.17 (s, 1H), 1.83 (s, 1H), 1.77 (s, 1H), 1.68 (s, 1H), 1.66-1.64 (m, 3H).

Example 44 Preparation of (R)—N-(2-benzoyl-4-chlorophenyl)-1-(3,4-dioxolobenzyl)-2-methylpyrrolyl-2-carboxamide The compound was prepared according to example 4.
$^1$H NMR (500 MHz, CDCl$_3$) δ 7.75 (d, J=9.3 Hz, 2H), 7.71-7.65 (m, 2H), 7.46 (d, J=5.0 Hz, 2H), 7.44-7.36 (m, 2H), 6.89 (s, 1H), 6.77 (s, 1H), 6.73 (s, 1H), 5.93-5.86 (m, 2H), 3.61 (s, 1H), 3.12 (s, 1H), 2.97 (s, 1H), 2.84 (s, 1H), 2.12 (s, 1H), 1.81 (s, 1H), 1.76 (s, 1H), 1.67 (s, 1H), 1.52-1.43 (m, 3H).

Example 45

Preparation of (R)—N-(2-benzoylphenyl)-1-benzyl-2-methylpyrrolyl-2-carboxamide

The compound was prepared according to example 4.
$^1$H NMR (500 MHz, CDCl$_3$) δ 9.92 (s, 1H), 7.73 (d, J=4.4 Hz, 2H), 7.70-7.64 (m, 2H), 7.54 (s, 1H), 7.46 (s, 1H), 7.43-7.37 (m, 2H), 7.31-7.25 (m, 2H), 7.21 (dd, J=5.5, 2.1 Hz, 4H), 3.57 (s, 1H), 3.18 (s, 1H), 2.97 (s, 1H), 2.84 (s, 1H), 2.10 (s, 1H), 1.82 (s, 1H), 1.76 (s, 1H), 1.67 (s, 1H), 1.51-1.42 (m, 3H).

Example 46 Preparation of (R)—N-(2-benzoyl-3-tolyl)-1-(3,4-dichlorobenzyl)-2-methylpyrrolyl-2-carboxamide The compound was prepared according to example 4.
$^1$H NMR (500 MHz, CDCl$_3$) δ 9.44 (s, 3H), 7.73-7.70 (m, 6H), 7.68 (s, 3H), 7.66 (s, 3H), 7.46 (s, 3H), 7.43-7.37 (m, 6H), 7.33 (s, 3H), 7.17 (s, 3H), 7.07 (d, J=8.1 Hz, 6H), 3.75 (s, 3H), 3.40 (s, 3H), 3.15 (s, 3H), 2.65 (s, 3H), 2.40-2.35 (m, 9H), 2.30 (s, 3H), 1.80 (s, 4H), 1.71 (d, J=45.0 Hz, 5H), 1.60-1.55 (m, 9H).

Example 47 Preparation of (R)—N-(2-benzoylphenyl)-1-(3,4-dichlorobenzyl)-2-methylpyrrolyl-2-carboxamide The compound was prepared according to example 4.
$^1$H NMR (500 MHz, CDCl$_3$) δ 9.37 (s, 3H), 7.77-7.68 (m, 12H), 7.52 (s, 3H), 7.46 (s, 3H), 7.43-7.37 (m, 6H), 7.33 (s, 3H), 7.21 (s, 3H), 7.17 (s, 3H), 7.06 (s, 3H), 3.75 (s, 3H), 3.40 (s, 3H), 3.15 (s, 3H), 2.65 (s, 3H), 2.30 (s, 3H), 1.80 (s, 4H), 1.75 (s, 2H), 1.66 (s, 3H), 1.59-1.54 (m, 9H).

Example 48 Preparation of (R)—N-(2-(4-chlorobenzoyl)phenyl)-1-(3,4-dichloro benzyl)-2-methylpyrrolyl-2-carboxamide The compound was prepared according to example 4.
$^1$H NMR (500 MHz, CDCl$_3$) δ 7.80 (s, 1H), 7.74 (s, 1H), 7.70-7.65 (m, 2H), 7.54 (s, 1H), 7.48-7.41 (m, 2H), 7.23 (d, J=14.6 Hz, 2H), 7.08 (s, 1H), 6.93 (s, 1H), 3.52 (s, 1H), 3.47 (s, 1H), 3.13 (s, 1H), 2.62 (s, 1H), 2.08 (s, 1H), 1.88 (s, 1H), 1.77 (s, 1H), 1.68 (s, 1H), 1.54-1.48 (m, 3H).

Example 49 Preparation of (R)—N-(2-(2-chlorobenzoyl)-4-chlorophenyl)-1-(3,4-dichlorobenzyl)-2-methylpyrrolyl-2-carboxamide The compound was prepared according to example 4.
$^1$H NMR (500 MHz, CDCl$_3$) δ 8.28 (s, 1H), 7.82 (s, 1H), 7.70 (s, 1H), 7.54 (s, 1H), 7.49 (s, 1H), 7.43 (d, J=15.8 Hz, 2H), 7.30 (s, 1H), 7.24 (s, 1H), 7.11 (d, J=3.3 Hz, 2H), 3.59 (s, 1H), 3.52 (s, 1H), 2.96 (s, 1H), 2.54 (s, 1H), 2.12 (s, 1H), 1.82 (s, 1H), 1.76 (s, 1H), 1.67 (s, 1H), 1.64-1.60 (m, 3H).

Example 50 Preparation of (R)—N-(2-(2-chlorobenzoyl)-4-bromophenyl)-1-(3,4-dichlorobenzyl)-2-methylpyrrolyl-2-carboxamide The compound was prepared according to example 4.
$^1$H NMR (500 MHz, CDCl$_3$) δ 8.50 (s, 3H), 8.04 (s, 3H), 7.73 (s, 3H), 7.62 (s, 3H), 7.55 (s, 3H), 7.45 (s, 3H), 7.31 (s, 3H), 7.23 (d, J=7.9 Hz, 6H), 7.14 (d, J=24.6 Hz, 6H), 3.55 (s, 3H), 3.51 (s, 3H), 3.01 (s, 3H), 2.55 (s, 3H), 2.11 (s, 3H), 1.80 (s, 4H), 1.76 (s, 2H), 1.67 (s, 3H), 1.50-1.41 (m, 9H).

Example 51 Preparation of (R)—N-(2-acetyl-4-chlorophenyl)-1-(3,4-dichlorobenzyl)-2-methylpyrrolyl-2-carboxamide The compound was prepared according to example 4.
$^1$H NMR (500 MHz, CDCl$_3$) δ 7.92 (s, 1H), 7.53 (s, 1H), 7.37-7.21 (m, 3H), 7.10 (s, 1H), 6.44 (s, 1H), 3.62 (s, 1H), 3.60 (s, 1H), 2.90 (s, 1H), 2.58 (s, 1H), 2.54-2.49 (m, 3H), 2.08 (s, 1H), 1.84 (s, 1H), 1.75 (s, 1H), 1.66 (s, 1H), 1.54-1.47 (m, 3H).

Example 52 Preparation of (R)—N-(2-propionyl-4-chlorophenyl)-1-(3,4-dichloro benzyl)-2-methylpyrrolyl-2-carboxamide The compound was prepared according to example 4.
$^1$H NMR (500 MHz, CDCl$_3$) δ 7.98 (s, 1H), 7.63 (s, 1H), 7.54 (s, 1H), 7.31-7.25 (m, 3H), 3.55 (s, 1H), 3.47 (s, 1H), 3.13-3.05 (m, 2H), 2.90 (s, 1H), 2.55 (s, 1H), 2.11 (s, 1H), 1.88 (s, 1H), 1.76 (s, 1H), 1.67 (s, 1H), 1.55-1.47 (m, 3H), 1.36-1.20 (m, 3H).

Example 53 Preparation of (R)—N-(2-(2-methylpropionyl)-4-chlorophenyl)-1-(3,4-dichlorobenzyl)-2-methylpyrrolyl-2-carboxamide The compound was prepared according to example 4.
$^1$H NMR (500 MHz, CDCl$_3$) δ 7.93 (s, 1H), 7.64 (s, 1H), 7.55 (s, 1H), 7.27 (d, J=0.8 Hz, 2H), 7.11 (s, 1H), 7.03 (s, 1H), 3.87 (s, 1H), 3.69 (s, 1H), 3.20 (s, 1H), 3.01 (s, 1H), 2.54 (s, 1H), 2.07 (s, 1H), 1.78 (d, J=26.3 Hz, 2H), 1.66 (s, 1H), 1.47-1.39 (m, 3H), 1.37-1.35 (m, 3H), 1.35 (s, 3H).

Example 54 Preparation of (R)—N-(2-(2,2-dimethylpropionyl)-4-chlorophenyl)-1-(3,4-dichlorobenzyl)-2-methylpyrrolyl-2-carboxamide The compound was prepared according to example 4.
$^1$H NMR (500 MHz, CDCl$_3$) δ 7.81 (s, 1H), 7.52 (s, 1H), 7.46 (d, J=10.3 Hz, 2H), 7.28 (s, 1H), 7.23 (s, 1H), 7.00 (s, 1H), 3.51 (d, J=11.3 Hz, 2H), 2.81 (s, 1H), 2.54 (s, 1H), 2.31 (s, 1H), 1.83 (s, 1H), 1.75 (s, 1H), 1.66 (s, 1H), 1.62-1.60 (m, 3H), 1.38-1.26 (m, 9H).

Example 55 Preparation of (R)—N-(2-trifluoromethylformyl-4-chlorophenyl)-1-(3,4-dichlorobenzyl)-2-methylpyrrolyl-2-carboxamide The compound was prepared according to example 4.
$^1$H NMR (500 MHz, CDCl$_3$) δ 8.05 (s, 1H), 7.79 (s, 1H), 7.58 (s, 1H), 7.24 (s, 1H), 7.21 (s, 1H), 7.12 (s, 1H), 3.62 (s, 1H), 3.41 (s, 1H), 3.15 (s, 1H), 2.64 (s, 1H), 2.27 (s, 1H), 1.83 (s, 1H), 1.75 (s, 1H), 1.66 (s, 1H), 1.56-1.43 (m, 3H).

Example 56 Preparation of (R)—N-(2-(2-thienylformyl)-4-chlorophenyl)-1-(3,4-dichlorobenzyl)-2-methylpyrrolyl-2-carboxamide The compound was prepared according to example 4.
$^1$H NMR (500 MHz, CDCl$_3$) δ 9.32 (s, 1H), 8.00 (s, 1H), 7.82 (s, 1H), 7.76 (s, 1H), 7.67 (s, 1H), 7.61 (s, 1H), 7.27 (dd, J=25.9, 14.1 Hz, 4H), 3.53 (s, 1H), 3.44 (s, 1H), 2.92 (s, 1H), 2.54 (s, 1H), 2.12 (s, 1H), 1.88 (s, 1H), 1.76 (s, 1H), 1.67 (s, 1H), 1.55-1.46 (m, 3H).

Example 57 Preparation of (R)—N-(2-(3-thienylformyl)-4-chlorophenyl)-1-(3,4-dichlorobenzyl)-2-methylpyrrolyl-2-carboxamide The compound was prepared according to example 4.
$^1$H NMR (500 MHz, CDCl$_3$) δ 8.74 (s, 1H), 7.95 (s, 1H), 7.67 (d, J=9.2 Hz, 2H), 7.60 (s, 1H), 7.40 (s, 1H), 7.28 (d, J=9.1 Hz, 2H), 7.19 (d, J=5.0 Hz, 2H), 3.54 (s, 1H), 3.44 (s, 1H), 3.00 (s, 1H), 2.56 (s, 1H), 2.09 (s, 1H), 1.84 (s, 1H), 1.76 (s, 1H), 1.67 (s, 1H), 1.52-1.45 (m, 3H).

Example 58

Preparation of (S)—N-(2-benzoylphenyl)-1-ethyl-2-methylpyrrolyl-2-carboxamide

The compound was prepared according to example 4.
$^1$H NMR (500 MHz, CDCl$_3$) δ 8.66 (s, 1H), 7.76 (s, 1H), 7.73-7.69 (m, 2H), 7.66 (s, 1H), 7.54 (s, 1H), 7.47 (s, 1H), 7.44-7.34 (m, 2H), 7.23 (s, 1H), 2.95 (d, J=2.0 Hz, 2H), 2.21 (d, J=5.3 Hz, 2H), 1.88 (s, 1H), 1.79 (s, 1H), 1.73 (d, J=24.0 Hz, 2H), 1.53-1.43 (m, 3H), 1.11-1.00 (m, 3H).

Example 59

Preparation of (R)—N-(2-benzoylphenyl)-1-ethyl-2-methylpyrrolyl-2-carboxamide

The compound was prepared according to example 4.
$^1$H NMR (500 MHz, CDCl$_3$) δ 9.05 (s, 7H), 7.76 (s, 7H), 7.73-7.64 (m, 21H), 7.54 (s, 7H), 7.47 (s, 7H), 7.43-7.36 (m, 14H), 7.23 (s, 7H), 2.96 (s, 7H), 2.51 (s, 8H), 2.45 (d, J=9.2 Hz, 13H), 2.14 (s, 7H), 1.77 (d, J=18.6 Hz, 11H), 1.66 (s, 9H), 1.63-1.60 (m, 21H), 1.13-1.01 (m, 21H).

Example 60 Preparation of (S)—N-(2-benzoyl-4-chlorophenyl)-1-(3,4-dichlorobenzyl)-2-methylpyrrolyl-2-carboxamide 5 g (14.58 mmol) of (S)-2-((2-benzoyl-4-chlorophenyl)carbamoyl)-2-methylprolinamide and 2.81 g (16.04 mmol) of 3,4-dichlorobenzyl chloride were dissolved in dichloromethane and a catalytic amount of potassium hydroxide was added and reacted at 10-30° C. for 15 min-1 h. Then water and dichloromethane were added and the aqueous phase was extracted three times with dichloromethane. The combined organic lays were washed with saturated sodium bicarbonate solution, dried over anhydrous magnesium sulfate and evaporated under normal pressure to remove dichloromethane to afford 7 g of (S)—N-(2-benzoyl-4-chlorophenyl)-1-(3,4-dichlorobenzyl)-2-methylpyrrolyl-2-carboxamide in a yield of 95%.

$^1$H NMR (400 MHz, CDCl$_3$) δ 11.76 (s, 1H), 8.65 (d, J=8.7 Hz, 1H), 7.86-7.40 (m, 8H), 7.22-7.13 (m, 2H), 3.79 (d, J=13.5 Hz, 1H), 3.39 (d, J=13.6 Hz, 1H), 3.15 (t, J=7.4 Hz, 1H), 2.39 (dd, J=15.9, 7.9 Hz, 1H), 2.23-2.14 (m, 1H), 1.95-1.75 (m, 3H), 1.39 (s, 3H).

$^{13}$C NMR (125 MHz, CDCl$_3$) δ 197.1, 176.5, 139.2, 138.4, 137.9, 133.4, 132.9, 132.3, 132.2, 130.8, 130.6, 130.1, 130.1, 128.5, 127.9, 127.2, 125.9, 122.8, 68.8, 53.5, 51.3, 40.1, 22.7, 16.4.

Example 61 Preparation of (S)—N-(2-benzoyl-4-chlorophenyl)-1-benzyl-2-methylpyrrolyl-2-carboxamide 3 g of (S)—N-(2-benzoyl-4-chlorophenyl)-1-benzyl-2-methylpyrrolyl-2-carboxamide (yield: 96%) was obtained by the substantially same preparation method as example 60.

$^1$H NMR (500 MHz, CDCl$_3$) δ 11.52 (s, 1H), 8.58 (d, J=8.9 Hz, 1H), 7.78-7.73 (m, 2H), 7.66-7.60 (m, 1H), 7.53-7.43 (m, 4H), 7.35-7.28 (m, 2H), 7.15-7.03 (m, 3H), 3.79 (d, J=13.0 Hz, 1H), 3.40 (d, J=13.1 Hz, 1H), 3.18-3.04 (m, 1H), 2.45-2.35 (m, 1H), 2.20-2.10 (m, 1H), 1.86-1.70 (m, 3H), 1.39 (s, 3H).

$^{13}$C NMR (125 MHz, CDCl$_3$) δ 196.7, 176.9, 138.9, 138.0, 137.9, 133.1, 133.1, 131.6, 130.2, 128.7, 128.3, 127.4, 127.0, 127.0, 123.0, 68.7, 54.4, 51.3, 40.4, 22.9, 16.5.

Example 62 Preparation of (S)—N-(2-benzoyl-4-chlorophenyl)-1-phenylethyl-2-methylpyrrolyl-2-carboxamide 4 g of (S)—N-(2-benzoyl-4-chlorophenyl)-1-benzyl-2-methylpyrrolyl-2-carboxamide in a yield of 92% was obtained by the substantially same preparation method as example 60.

$^1$H NMR (500 MHz, CDCl$_3$) δ 11.60 (s, 1H), 8.57 (d, J=9.0 Hz, 1H), 7.73 (d, J=7.6 Hz, 2H), 7.60 (t, J=7.4 Hz, 1H), 7.52-7.40 (m, 4H), 7.17-7.05 (m, 3H), 6.96 (d, J=6.7 Hz, 2H), 3.41-3.31 (m, 1H), 2.55-2.33 (m, 5H), 2.14-2.06 (m, 1H), 1.93 (s, 1H), 1.86-1.69 (m, 4H), 1.24 (s, 3H).

$^{13}$C NMR (125 MHz, CDCl$_3$) δ 196.6, 177.4, 142.1, 138.0, 137.9, 133.1, 131.6, 130.2, 128.6, 128.3, 128.3, 127.3, 127.0, 125.7, 123.1, 68.6, 51.5, 49.9, 40.4, 33.9, 30.9, 22.9, 16.3.

Example 63 Preparation of (R)—N-(2-benzoyl-4-chlorophenyl)-1-(3,4-dimethoxy benzyl)-2-methylpyrrolyl-2-carboxamide The compound was prepared according to example 4.
$^1$H NMR (500 MHz, CDCl$_3$) δ 11.64 (s, 1H), 8.56 (d, J=9.0 Hz, 1H), 7.73-7.69 (m, 2H), 7.64-7.59 (m, 1H), 7.52-7.48 (m, 3H), 7.45 (d, J=2.5 Hz, 1H), 7.08 (d, J=2.0 Hz, 1H), 6.83 (dd, J=8.2, 1.9 Hz, 1H), 6.58 (d, J=8.2 Hz, 1H), 3.79 (s, 3H), 3.77 (s, 3H), 3.37 (d, J=13.0 Hz, 1H), 3.14 (td, J=8.1, 7.6, 4.1 Hz, 1H), 2.43-2.36 (m, 1H), 2.18-2.08 (m, 1H), 1.85-1.69 (m, 4H), 1.39 (s, 3H).
$^{13}$C NMR (126 MHz, CDCl$_3$) δ 196.8, 176.9, 148.9, 147.9, 138.2, 137.9, 133.2, 132.9, 131.8, 131.5, 130.0, 128.5, 127.3, 126.6, 123.2, 120.6, 111.8, 110.7, 68.5, 55.8, 54.0, 51.1, 40.2, 22.6, 16.2.

Example 64 Preparation of (R)—N-(2-benzoyl-4-chlorophenyl)-1-(3,4-dibromo benzyl)-2-methylpyrrolyl-2-carboxamide The compound was prepared according to example 4.
$^1$H NMR (500 MHz, CDCl$_3$) δ 11.72 (s, 1H), 8.63 (d, J=8.7 Hz, 1H), 7.83 (d, J=1.9 Hz, 1H), 7.76 (dd, J=8.2, 1.4 Hz, 2H), 7.65-7.62 (m, 1H), 7.55-7.47 (m, 4H), 7.31 (d, J=8.2 Hz, 1H), 7.18 (d, J=8.2 Hz, 1H), 3.77 (d, J=13.5 Hz, 1H), 3.38 (d, J=13.5 Hz, 1H), 3.16 (t, J=8.1 Hz, 1H), 2.40 (q, J=8.1 Hz, 1H), 2.23-2.13 (m, 1H), 1.91-1.75 (m, 3H), 1.39 (s, 3H).
$^{13}$C NMR (126 MHz, CDCl$_3$) δ 197.0, 176.5, 140.0, 138.4, 137.9, 133.8, 133.4, 133.3, 133.0, 132.2, 130.1, 128.8, 128.5, 127.2, 125.9, 124.7, 122.9, 122.8, 68.8, 53.4, 51.3, 40.1, 22.6, 16.4.

Example 65

Preparation of Nickel Chelate 5 g of (R)—N-(2-benzoyl-4-chlorophenyl)-1-ethyl-2-methylpyrrolyl-2-carboxamide (13.48 mmol), 6.68 g of 3-amino 3-phenylpropionic acid (40.44 mmol) and 4.77 g of nickel acetate (26.96 mmol) were dissolved in 200 ml methanol and 15.13 g of potassium t-butoxide (134.82 mmol) was added. The reaction system was heated to 60-90° C. for 6-12 h, and then water and dichloromethane were added. The aqueous phase was extracted three times with dichloromethane. The combined organic lays were washed with saturated sodium bicarbonate solution, dried over anhydrous magnesium sulfate and evaporated under normal pressure to remove dichloromethane to obtain 6.8 g of nickel chelate in a yield of 87%.
mp 174-176° C. $[α]_{20}^D$=−2531.8 (c=0.044, CHCl$_3$).
$^1$H NMR (400 MHz, Methanol-d$_4$) δ 8.18 (d, J=9.1 Hz, 1H), 7.71-7.46 (m, 9H), 7.31 (dd, J=9.1, 2.6 Hz, 1H), 7.20 (d, J=7.6 Hz, 1H), 6.72 (d, J=2.6 Hz, 1H), 4.60 (d, J=3.7 Hz, 1H), 3.23 (td, J=12.3, 11.3, 7.1 Hz, 1H), 2.93 (dd, J=17.8, 2.8 Hz, 1H), 2.80 (t, J=9.2 Hz, 1H), 2.69 (dd, J=17.8, 4.1 Hz, 1H), 2.40 (dq, J=14.5, 7.3 Hz, 1H), 2.23 (dq, J=13.8, 6.9 Hz, 1H), 2.02-1.91 (m, 1H), 1.87 (t, J=7.3 Hz, 3H), 1.80-1.45 (m, 3H), 1.10 (s, 3H).
$^{13}$C NMR (150 MHz, CDCl$_3$) δ 182.1, 172.8, 171.3, 142.0, 139.8, 134.9, 133.0, 132.9, 130.5, 130.0, 129.9, 129.5, 129.4, 128.5, 127.3, 126.9, 126.6, 125.6, 125.3, 73.3, 63.1, 53.5, 49.1, 40.5, 38.2, 20.3, 17.3, 15.3.
LRMS (ESI+APCI) m/z: 574.1, HRMS (ESI) m/z: found: 574.1405, calcd 574.1402 for C$_{30}$H$_{30}$ClN$_3$NiO$_3^+$ [M+H]$^+$.

Example 66

Preparation of (S)-3-amino-3-phenylpropionic Acid

Nickel chelate was dissolved in methanol and concentrated hydrochloric acid was added. The reaction system was heated to 60-100° C. for 15 minutes-2 hours, then water and dichloromethane were added to the reaction system. The aqueous phase was extracted three times with dichloromethane. The combined organic layers were washed with saturated sodium chloride solution, dried over anhydrous magnesium sulfate and evaporated under normal pressure to remove dichloromethane to obtain 800 mg of (S)-3-amino-3-phenylpropionic acid in a yield of 92%.
mp=223-224° C. $[α]_{20}^D$=−12 (c=0.1, H$_2$O).
$^1$H NMR (500 MHz, D$_2$O) δ 7.58-7.41 (m, 5H), 4.70 (t, J=7.3 Hz, 1H), 3.11-2.86 (m, 2H).
$^{13}$C NMR (125 MHz, D$_2$O) δ 175.93, 135.66, 129.38, 129.27, 126.91, 52.29, 39.48.
LRMS (ESI+APCI) m/z: 166.1, HRMS (ESI) m/z: found: 166.0858, calcd 166.0863 for C$_9$H$_{11}$NO$^{2+}$ [M+H]$^+$.

Example 67

Preparation of (S)-3-tert-butoxycarbonylamino3-phenylpropionic Acid (S)-3-amino3-phenylpropionic acid (0.33 g, 2 mmol) was dissolved in 3 mL saturated NaHCO$_3$ and di-t-butyl carbonate (0.52 g, 2.2 mmol) was slowly added and reacted at room temperature for 24 h. Then the mixture was adjusted to pH 2-3 with 1 N aqueous solution of hydrochloric acid. The aqueous phase was extracted three times with ethyl acetate. Then the combined organic layers were washed with saturated sodium chloride solution, dried over anhydrous magnesium sulfate and evaporated to obtain 0.52 g of (S)-3-tert-butoxycarbonylamino3-phenylpropionic acid (98%).
$^1$H NMR (400 MHz, CDCl$_3$) δ 7.34-7.24 (m, 5H), 5.48 (s, br, 1H), 5.11-4.93 (m, 1H), 2.84 (s, 2H), 1.41 (s, br, 9H).

Example 68

Preparation of tert-butyl (S)—N-(3-hydroxy-1-phenylpropyl)carbamate (S)-3-tert-butoxycarbonylamino3-phenylpropanamine (0.40 g, 1.5 mmol) was dissolved in 5 mL THF under N$_2$ and BH$_3$.THF (3 mL, 1 M/mL) was slowly added dropwise and then reacted for 2 h. An appropriate amount of acetone was added to consume excessive BH$_3$. Then saturated sodium bicarbonate solution was added and the aqueous phase was extracted three times with ethyl acetate. The combined organic layers were washed with saturated sodium chloride solution, dried over anhydrous magnesium sulfate and evaporated to obtain 0.39 g of tert-butyl (S)—N-(3-hydroxy-1-phenylpropyl)carbamate (104%).

Example 69

Preparation of tert-butyl (S)—N-(3-O-1-phenylpropyl)carbamate

At 0° C., tert-butyl (S)—N-(3-hydroxy-1-phenylpropyl) carbamate (0.39 g, 1.5 mmol) was dissolved in 10 mL dichloromethane and Dess Martin oxidant (0.76 g, 1.8 mmol) was slowly added and reacted at room temperature for 2 h. Then saturated sodium bicarbonate solution was added and the aqueous phase was extracted three times with dichloromethane. The combined organic layers were washed with saturated sodium chloride solution, dried over anhydrous magnesium sulfate, and evaporated. The crude product was purified by column chromatography (petroleum ether:ethyl acetate=3:1) to obtain 0.34 g of tert-butyl (S)—N-(3-O-1-phenylpropyl)carbamate (92%).

Example 70 Preparation of tert-butyl (S)-3-{[(1R, 3R,5S)-3-(3-isopropyl-5-methyl-4H-1,2,4-triazol-4-yl)-8-azabicyclo[3.2.1]octan-8-yl]-1phenylpropyl}carbamate (1R,3R,5S)-3-(3-isopropyl-5-methyl-4H-1,2,4-triazol-4-yl)-8-azabicyclo[3.2.1]octane (0.28 g, 1.2 mmol) was dissolved in 10 mL 1,2-dichloroethane at room temperature and tert-butyl (S)—N-(3-O-1-phenylpropyl)carbamate (0.25 g, 1 mmol), glacial acetic acid (12 µL, 0.2 mmol), and then sodium triacetoxyborohydride (0.32 g, 1.5 mmol) were added and reacted at room temperature for 12 h. The mixture was adjusted to pH 11-12 with 2 M sodium hydroxide solution and the aqueous phase was extracted three times with dichloromethane. The combined organic layers were washed with saturated sodium chloride solution, dried over anhydrous magnesium sulfate and evaporated. The crude product was purified by column chromatography (dichloromethane:methanol=15:1) to obtain 0.33 g of tert-butyl (S)-3-{[(R,3R,5S)-3-(3-isopropyl-5-methyl-4H-1,2,4-triazol-4-yl)-8-azabicyclo[3.2.1]octan-8-yl]-1phenylpropyl}carbamate (71%). LRMS (ESI+APCI) m/z: 468.3.

Example 71 Preparation of 4,4-difluoro-N-[(1S)-3-[exo-3-(3-isopropyl-5-methyl-4H-1,2,4-triazol-4-yl)-8-azabicyclo[3.2.1]octan-8-yl]-1-phenylpropyl]cyclohexane-1-carboxamide Tert-butyl (S)-3-{[(1R,3R,5S)-3-(3-isopropyl-5-methyl-4H-1,2,4-triazol-4-yl)-8-azabicyclo[3.2.1]octan-8-yl]-phenylpropyl}carbamate (93.4 mg, 0.2 mmol) was dissolved in 5 mL methanol at 0° C. and 4 N dioxane hydrochloride solution (5 ml) was added slowly at room temperature for 3 h. The mixture was evaporated to obtain a corresponding amine intermediate which was then dissolved in 5 mL dichloromethane. Triethylamine (138.7 µL, 1 mmol) was added, followed by adding 4,4-difluorocyclohexanecarboxylic acid (39.4 mg, 0.24 mmol), EDCI (46.0 mg, 0.24 mmol) and HOBT (32.4 mg, 0.24 mmol). The mixture was reacted at room temperature for 12 h and then adjusted to pH 11-12 with 2M sodium hydroxide solution. The aqueous phase was extracted three times with dichloromethane. The combined organic layers were washed with saturated sodium chloride solution, dried over anhydrous magnesium sulfate, and evaporated. The crude product was purified by column chromatography (dichloromethane:methanol=10:1) to obtain 76.9 mg of 4,4-difluoro-N-[(1S)-3-[exo-3-(3-isopropyl-5-methyl-4H-1,2,4-triazol-4-yl)-8-azabicyclo[3.2.1]octan-8-yl]-1-phenylpropyl]cyclohexane-1-carboxamide (75%, ee>98.2%).

$[\alpha]^{25}_D$=-28.4° (c=0.5, CHCl$_3$).
$^1$H NMR (400 MHz, CDCl$_3$) δ [ppm] 7.35-7.31 (m, 2H), 7.28-7.26 (m, 3H), 6.82-6.66 (m, br, 1H), 5.12-5.07 (m, 1H), 4.32-4.26 (m, 1H), 3.40 (d, br, 2H), 3.01-2.94 (m, 1H), 2.48 (s, 3H), 2.44 (t, J=8 Hz, 2H), 2.28-1.64 (m, 19H), 1.37 (d, J=4 Hz, 6H).

$^{13}$C NMR (151 MHz, CDCl$_3$) δ 173.71, 159.23, 150.70, 141.97, 128.77, 127.49, 126.49, 58.99, 58.37, 51.94, 47.99, 47.30, 42.74, 35.40, 35.28, 34.66, 32.95 (J $^{13}$C-$^{19}$F 6 Hz), 32.82, 32.79, 32.63 (J $^{13}$C-$^{19}$F 4.5 Hz), 26.66, 26.62, 25.98 (J $^{13}$C-$^{19}$F 9 Hz), 25.89 (J $^{13}$C-$^{19}$F 9 Hz), 25.80, 21.63, 13.07.
LRMS (ESI+APCI) m/z [M+H]$^+$: 514.3, HRMS (ESI) m/z: calcd for C$_{29}$H$_{42}$F$_2$N$_5$O+[M+H]$^+$: 514.3552, found: 514.3551.

Example 72

Preparation of Nickel Chelate of 3-amino-3-(2-fluoro)phenylpropionic Acid

The preparation process was substantially the same as those in example 65. 3-amino-3-phenylpropionic acid was replaced by 3-amino-3-(2-fluoro)phenylpropionic acid to obtain nickel chelate of 3-amino-3-(2-fluoro)phenylpropionic acid in a yield of 92%.

mp=180-181° C. $[\alpha]^{20}_D$=-3281.3 (c=0.048, CHCl$_3$).
$^1$H NMR (400 MHz, Methanol-d$_4$) δ 8.21 (d, J=9.1 Hz, 1H), 7.69-7.50 (m, 5H), 7.45-7.35 (m, 3H), 7.30 (dd, J=9.1, 2.6 Hz, 1H), 7.12-7.05 (m, 1H), 6.65 (d, J=2.6 Hz, 1H), 4.71 (t, J=3.3 Hz, 1H), 3.26-3.14 (m, 1H), 2.93-2.82 (m, 2H), 2.73 (dd, J=18.0, 4.4 Hz, 1H), 2.44-2.33 (m, 1H), 2.30-2.18 (m, 1H), 2.04-1.92 (m, 1H), 1.90-1.78 (m, 4H), 1.75-1.55 (m, 2H), 1.09 (s, 3H).
$^{13}$C NMR (150 MHz, CDCl$_3$) δ 181.5, 171.7, 162.0, 142.1, 135.1, 133.1, 132.9, 131.0, 130.5, 130.2, 129.6, 128.8, 128.7, 128.6, 127.3, 127.3, 126.5, 125.4, 125.1, 124.8, 116.7, 116.5, 73.7, 60.0, 53.2, 49.2, 40.6, 38.9, 20.7, 16.7, 15.2.
LRMS (ESI+APCI) m/z: 592.2, HRMS (ESI) m/z: found: 592.1311, calcd 592.1308 for C$_{30}$H$_{29}$ClFN$_3$NiO$_3$$^+$ [M+H]$^+$.

Example 73

Preparation of Nickel Chelate of 3-amino-3-(4-chloro)phenylpropionic Acid

The preparation process was substantially the same as those in example 65. 3-amino-3-phenylpropionic acid was replaced by 3-amino-3-(4-chloro)phenylpropionic acid to obtain nickel chelate of 3-amino-3-(4-chloro)phenylpropionic acid in a yield of 93%.

mp=180-182° C. $[\alpha]^{20}_D$=-3512.5 (c=0.04, CHCl$_3$).
$^1$H NMR (500 MHz, Methanol-d$_4$) δ 8.19 (d, J=9.1 Hz, 1H), 7.68-7.47 (m, 8H), 7.31 (dd, J=9.1, 2.6 Hz, 1H), 7.21 (dt, J=7.6, 1.5 Hz, 1H), 6.71 (d, J=2.6 Hz, 1H), 4.57 (t, J=3.3 Hz, 1H), 3.30-3.21 (m, 1H), 2.90 (dd, J=17.9, 2.8 Hz, 1H), 2.86-2.79 (m, 1H), 2.70 (dd, J=17.9, 4.1 Hz, 1H), 2.46-2.37 (m, 1H), 2.28-2.19 (m, 1H), 2.07-1.99 (m, 1H), 1.88 (t, J=7.3 Hz, 3H), 1.85-1.77 (m, 1H), 1.75-1.63 (m, 1H), 1.61-1.52 (m, 1H), 1.12 (s, 3H).
$^{13}$C NMR (125 MHz, Methanol-d$_4$) δ 183.6, 176.7, 173.8, 142.6, 139.8, 136.1, 135.6, 134.1, 133.5, 131.6, 131.2, 130.8, 130.6, 130.4, 129.6, 128.4, 128.3, 126.9, 126.6, 75.0, 63.5, 53.7, 50.2, 41.3, 38.3, 21.4, 17.7, 15.5. LRMS (ESI+APCI) m/z: 608.1, HRMS (ESI) n/z: found: 608.1027, calcd 608.1012 for C$_{30}$H$_{29}$Cl$_2$N$_3$NiO$_3$$^+$ [M+H]$^+$.

Example 74

Preparation of Nickel Chelate of 3-amino-3-(3,4-dimethoxy)phenylpropionic Acid

The preparation process was substantially the same as those in example 65. 3-amino-3 phenylpropionic acid was replaced by 3-amino-3-(3,4-dimethoxy)phenylpropionic acid to obtain nickel chelate of 3-amino-3-(3,4dimethoxy)phenylpropionic acid in a yield of 93%. mp=160-162° C. $[\alpha]^{20}_D$=−2768.3 (c=0.06, CHCl$_3$).

$^1$H NMR (400 MHz, Methanol-d$_4$) δ 8.16 (d, J=9.1 Hz, 1H), 7.67-7.50 (m, 4H), 7.32 (dd, J=9.1, 2.6 Hz, 1H), 7.24 (d, J=8.4 Hz, 1H), 7.20-7.13 (m, 1H), 7.09-7.03 (m, 1H), 6.89 (d, J=2.2 Hz, 1H), 6.71 (d, J=2.6 Hz, 1H), 4.56 (t, J=3.4 Hz, 1H), 3.93 (s, 3H), 3.82 (s, 3H), 3.27-3.16 (m, 1H), 2.94-2.79 (m, 2H), 2.67 (dd, J=17.8, 4.1 Hz, 1H), 2.46-2.35 (m, 1H), 2.31-2.21 (m, 1H), 2.04-1.81 (m, 5H), 1.72-1.50 (m, 2H), 1.12 (s, 3H).

$^{13}$C NMR (125 MHz, CDCl$_3$) δ 182.0, 172.9, 171.0, 149.7, 149.4, 142.0, 135.0, 133.0, 132.9, 132.5, 130.5, 130.0, 129.9, 129.4, 127.2, 126.7, 125.7, 125.3, 119.6, 112.0, 110.0, 73.4, 62.9, 56.4, 56.3, 53.4, 49.1, 40.4, 38.4, 20.5, 17.3, 15.3.

LRMS (ESI+APCI) m/z: 634.2, HRMS (ESI) m/z: found: 634.1627, calcd 634.1613 for C$_{32}$H$_{34}$ClN$_3$NiO$_5^+$ [M+H]$^+$.

Example 75

Preparation of Nickel Chelate of 3-amino-3-(4-isopropyl)phenylpropionic Acid

The preparation process was substantially the same as those in example 65. 3-amino-3-phenylpropionic acid was replaced by 3-amino-3-(4-isopropyl)phenylpropionic acid to obtain nickel chelate of 3-amino-3-(4-isopropyl)phenylpropionic acid in a yield of 92%. mp=120-122° C. $[\alpha]^{20}_D$=−2287.5 (c=0.048, CHCl$_3$).

$^1$H NMR (400 MHz, Methanol-d$_4$) δ 8.17 (d, J=9.2 Hz, 1H), 7.66-7.47 (m, 6H), 7.39 (d, J=8.0 Hz, 2H), 7.31 (dd, J=9.1, 2.6 Hz, 1H), 7.22-7.16 (m, 1H), 6.72 (d, J=2.6 Hz, 1H), 4.56 (d, J=3.5 Hz, 1H), 3.27-3.17 (m, 1H), 3.10-2.98 (m, 1H), 2.90 (dd, J=17.8, 2.8 Hz, 1H), 2.79 (t, J=9.1 Hz, 1H), 2.67 (dd, J=17.8, 4.2 Hz, 1H), 2.45-2.34 (m, 1H), 2.28-2.17 (m, 1H), 1.97-1.82 (m, 4H), 1.77-1.45 (m, 3H), 1.34 (d, J=6.9 Hz, 6H), 1.10 (s, 3H).

$^{13}$C NMR (125 MHz, CDCl$_3$) δ 182.0, 172.9, 171.1, 149.6, 142.0, 137.3, 135.0, 133.0, 132.9, 130.5, 130.0, 130.0, 129.4, 127.6, 127.4, 127.0, 126.7, 125.6, 125.3, 73.4, 62.9, 53.3, 49.1, 40.3, 38.1, 34.1, 24.3, 24.2, 20.4, 17.2, 15.3.

LRMS (ESI+APCI) m/z: 616.2, HRMS (ESI) m/z: found: 616.1886, calcd 616.1871 for C$_{33}$H$_{36}$ClN$_3$NiO$_3^+$ [M+H]$^+$.

Example 76

Preparation of Nickel Chelate of 3-amino-3-(4-methoxy)phenylpropionic Acid

The preparation process was substantially the same as those in example 65. 3-amino-3-phenylpropionic acid was replaced by 3-amino-3-(4-methoxy)phenylpropionic acid to obtain nickel chelate of 3-amino-3-(4-methoxy)phenylpropionic acid in a yield of 93%.

mp=172-173° C. $[\alpha]^{20}_D$=−3139.6 (c=0.048, CHCl$_3$).

$^1$H NMR (500 MHz, Methanol-d$_4$) δ 8.18 (d, J=9.1 Hz, 1H), 7.65-7.49 (m, 4H), 7.40-7.36 (m, 2H), 7.30 (dd, J=9.1, 2.6 Hz, 1H), 7.23-7.16 (m, 3H), 6.70 (d, J=2.6 Hz, 1H), 4.53 (t, J=3.5 Hz, 2H), 3.89 (s, 3H), 3.30-3.19 (m, 1H), 2.90-2.79 (m, 2H), 2.65 (dd, J=17.8, 4.2 Hz, 1H), 2.47-2.35 (m, 1H), 2.27-2.16 (m, 1H), 2.01-1.82 (m, 5H), 1.69-1.50 (m, 2H), 1.11 (s, 3H).

$^{13}$C NMR (125 MHz, Methanol-d$_4$) δ 183.6, 177.0, 173.0, 161.6, 142.6, 136.2, 134.0, 133.4, 132.9, 131.6, 131.5, 130.8, 130.3, 129.1, 128.5, 128.4, 126.9, 126.5, 115.9, 75.0, 63.6, 56.1, 53.8, 50.1, 41.3, 38.4, 21.3, 17.6, 15.5.

LRMS (ESI+APCI) m/z: 604.1, HRMS (ESI) m/z: found: 604.1518, calcd 604.1508 for C$_{31}$H$_{32}$ClN$_3$NiO$_4^+$ [M+H]$^+$.

Example 77

Preparation of Nickel Chelate of 3-amino-3-(3-methoxy)phenylpropionic Acid

The preparation process was substantially the same as those in example 65. 3-amino-3-phenylpropionic acid was replaced by 3-amino-3-(3-methoxy)phenylpropionic acid to obtain nickel chelate of 3-amino-3-(3-methoxy)phenylpropionic acid in a yield of 90%.

mp=165-167° C. $[\alpha]^{20}_D$=−2850.0 (c=0.048, CHCl$_3$).

$^1$H NMR (500 MHz, Methanol-d$_4$) δ 8.17 (d, J=9.1 Hz, 1H), 7.70-7.47 (m, 5H), 7.31 (dd, J=9.1, 2.6 Hz, 1H), 7.20-6.95 (m, 4H), 6.71 (d, J=2.6 Hz, 1H), 4.56 (t, J=3.4 Hz, 1H), 3.85 (s, 3H), 3.31-3.25 (m, 1H), 2.97-2.77 (m, 2H), 2.67 (dd, J=17.8, 4.1 Hz, 1H), 2.47-2.34 (m, 1H), 2.30-2.21 (m, 1H), 2.03-1.76 (m, 5H), 1.68-1.47 (m, 2H), 1.12 (s, 3H).

$^{13}$C NMR (125 MHz, Methanol-d$_4$) δ 183.6, 177.0, 173.4, 162.1, 142.6, 142.4, 136.1, 134.1, 133.5, 131.9, 131.6, 131.4, 130.8, 130.4, 128.4, 128.4, 126.9, 126.6, 119.9, 114.4, 114.1, 75.1, 64.0, 55.9, 53.6, 50.2, 41.0, 38.4, 21.4, 17.7, 15.5.

LRMS (ESI+APCI) m/z: 604.1, HRMS (ESI) m/z: found: 604.1518, calcd 604.1508 for C$_{31}$H$_{32}$ClN$_3$NiO$_4^+$ [M+H]$^+$.

Example 78

Preparation of Nickel Chelate of 3-amino-3-(3-trifluoromethyl)phenylpropionic Acid The preparation process was substantially the same as those in example 65. 3-amino-3-phenylpropionic acid was replaced by 3-amino-3-(3-trifluoromethyl) phenylpropionic acid to obtain nickel chelate of 3-amino-3-(3-trifluoromethyl)phenylpropionic acid in a yield of 50%.

mp=158-160° C. $[\alpha]^{20}_D$=−3280.6 (c=0.036, CHCl$_3$).

$^1$H NMR (500 MHz, Methanol-d$_4$) δ 8.19 (d, J=9.2 Hz, 1H), 7.86 (dd, J=28.1, 4.2 Hz, 3H), 7.69-7.50 (m, 5H), 7.33 (dd, J=9.1, 2.7 Hz, 1H), 7.18 (d, J=7.7 Hz, 1H), 6.73 (d, J=2.6 Hz, 1H), 4.68 (t, J=3.3 Hz, 1H), 3.24-3.12 (m, 1H), 2.98 (dd, J=18.0, 2.9 Hz, 1H), 2.87-2.73 (m, 2H), 2.45-2.19 (m, 2H), 2.06-1.94 (m, 1H), 1.88 (t, J=7.3 Hz, 3H), 1.72-1.48 (m, 3H), 1.12 (s, 3H).

$^{13}$C NMR (125 MHz, Methanol-d$_4$) δ 183.6, 176.6, 174.2, 142.7, 142.4, 136.0, 134.2, 133.7, 132.8, 132.6, 132.2, 131.7, 131.7, 131.2, 130.9, 130.5, 128.4, 128.2, 127.0, 126.6, 126.5, 123.9, 75.0, 63.6, 53.5, 50.2, 41.1, 38.3, 21.4, 17.7, 15.5.

LRMS (ESI+APCI) m/z: 642.1, HRMS (ESI) m/z: found: 642.1268, calcd 642.1276 for C$_{31}$H$_{29}$ClF$_3$N$_3$NiO$_3^+$ [M+H]$^+$.

Example 79

Preparation of Nickel Chelate of 3-amino-3-(3-pyridyl)propionic Acid

The preparation process was substantially the same as those in example 65. 3-amino-3-phenylpropionic acid was replaced by 3-amino-3-(3-pyridyl)propionic acid to obtain nickel chelate of 3-amino-3-(3-pyridyl)propionic acid in a yield of 80%.

mp=138-140° C. $[\alpha]^{20}{}_D$=−2835.4 (c=0.048, CHCl$_3$).

$^1$H NMR (400 MHz, Methanol-d$_4$) δ 8.78 (d, J=2.5 Hz, 1H), 8.76 (dd, J=4.6, 1.4 Hz, 1H), 8.19 (d, J=9.2 Hz, 1H), 8.00-7.92 (m, 1H), 7.75-7.51 (m, 5H), 7.33 (dd, J=9.2, 2.6 Hz, 1H), 7.24 (d, J=7.7 Hz, 1H), 6.72 (d, J=2.6 Hz, 1H), 4.70 (t, J=3.6 Hz, 1H), 3.29-3.18 (m, 1H), 2.99 (dd, J=17.9, 2.9 Hz, 1H), 2.87-2.73 (m, 2H), 2.44-2.25 (m, 2H), 2.09-1.98 (m, 1H), 1.88 (t, J=7.3 Hz, 3H), 1.74-1.50 (m, 3H), 1.13 (s, 3H).

$^{13}$C NMR (125 MHz, Methanol-d$_4$) δ 183.4, 176.4, 174.4, 150.1, 148.6, 142.7, 137.7, 136.5, 136.0, 134.1, 133.7, 131.7, 131.1, 130.9, 130.5, 128.3, 128.3, 126.9, 126.6, 125.9, 75.1, 62.4, 53.4, 50.3, 41.1, 38.1, 21.4, 17.7, 15.5.

LRMS (ESI+APCI) m/z: 575.1, HRMS (ESI) m/z: found: 575.1347, calcd 575.1354 for C$_{29}$H$_{29}$ClN$_4$NiO$_3{}^+$ [M+H]$^+$.

Example 80

Preparation of Nickel Chelate of 3-amino-3-(2-thienyl)propionic Acid

The preparation process was substantially the same as those in example 65. 3-amino-3-phenylpropionic acid was replaced by 3-amino-3-(2-thienyl)propionic acid to obtain nickel chelate of 3-amino-3-(2-thienyl)propionic acid in a yield of 95%.

mp=145-146° C. $[\alpha]^{20}{}_D$=−2775.0 (c=0.048, CHCl$_3$).

$^1$H NMR (500 MHz, Methanol-d$_4$) δ 8.16 (d, J=9.1 Hz, 1H), 7.72 (d, J=5.1 Hz, 1H), 7.68-7.48 (m, 4H), 7.35-7.25 (m, 2H), 7.19-7.11 (m, 2H), 6.70 (d, J=2.6 Hz, 1H), 4.72 (t, J=4.1 Hz, 1H), 3.39 (ddd, J=13.2, 11.5, 5.4 Hz, 1H), 2.97-2.91 (m, 1H), 2.86-2.68 (m, 2H), 2.50-2.40 (m, 1H), 2.33-2.23 (m, 1H), 2.22-2.12 (m, 1H), 2.08-2.00 (m, 1H), 1.92 (t, J=7.3 Hz, 3H), 1.83-1.71 (m, 1H), 1.64-1.55 (m, 1H), 1.15 (s, 3H).

$^{13}$C NMR (125 MHz, Methanol-d$_4$) δ 183.6, 176.3, 173.3, 145.2, 142.7, 135.8, 134.1, 133.6, 131.7, 131.2, 130.7, 130.4, 129.2, 128.4, 128.4, 127.9, 126.9, 126.7, 126.4, 75.1, 61.9, 53.8, 50.3, 41.3, 39.4, 21.8, 17.8, 15.6.

LRMS (ESI+APCI) m/z: 580.1, HRMS (ESI) m/z: found: 580.0976, calcd 580.0966 for C$_{28}$H$_{28}$ClN$_3$NiO$_3$S$^+$ [M+H]$^+$.

Example 81

Preparation of Nickel Chelate of 3-amino-3-(1-naphthyl)propionic Acid

The preparation process was substantially the same as those in example 65. 3-amino-3-phenylpropionic acid was replaced by 3-amino-3-(1-naphthyl)propionic acid to obtain nickel chelate of 3-amino-3-(1-naphthyl)propionic acid in a yield of 91%.

mp=145-147° C. $[\alpha]^{20}{}_D$=−2292.0 (c=0.05, CHCl$_3$).

$^1$H NMR (400 MHz, Methanol-d$_4$) δ 8.19 (d, J=9.2 Hz, 1H), 8.14 (d, J=8.6 Hz, 1H), 8.02-7.94 (m, 3H), 7.68-7.51 (m, 7H), 7.33 (dd, J=9.1, 2.6 Hz, 1H), 7.31-7.26 (m, 1H), 6.75 (d, J=2.5 Hz, 1H), 4.75 (t, J=3.5 Hz, 1H), 3.10-3.03 (m, 1H), 3.03-2.93 (m, 1H), 2.78 (dd, J=17.9, 4.1 Hz, 1H), 2.72-2.64 (m, 1H), 2.43-2.30 (m, 1H), 2.22-2.11 (m, 1H), 1.86 (t, J=7.3 Hz, 3H), 1.71-1.59 (m, 1H), 1.39 (q, J=9.9 Hz, 1H), 1.22-1.05 (m, 2H), 1.01 (s, 3H).

$^{13}$C NMR (150 MHz, Methanol-d$_4$) δ 182.1, 172.8, 171.3, 142.1, 137.0, 135.0, 133.6, 133.1, 133.0, 130.6, 130.1, 130.0, 129.5, 129.3, 128.5, 127.8, 127.3, 127.1, 127.0, 126.7, 125.7, 125.5, 125.3, 124.9, 63.3, 53.5, 49.0, 40.2, 38.4, 19.9, 17.1, 15.3.

LRMS (ESI+APCI) m/z: 624.2, HRMS (ESI) m/z: found: 624.1576, calcd 624.1558 for C$_{34}$H$_{32}$ClN$_3$NiO$_3{}^+$ [M+H]$^+$.

Example 82

Preparation of Nickel Chelate of Nickel Chelate of 3-Aminobutyric Acid

The preparation process was substantially the same as those in example 65. 3-amino-3-phenylpropionic acid was replaced by 3-aminobutyric acid to obtain nickel chelate of 3-aminobutyric acid in a yield of 87%.

mp=240-242° C. $[\alpha]^{20}{}_D$=−4309.5 (c=0.042, CHCl$_3$).

$^1$H NMR (500 MHz, Methanol-d$_4$) δ 8.14 (d, J=9.1 Hz, 1H), 7.64-7.43 (m, 4H), 7.27 (dd, J=9.1, 2.6 Hz, 1H), 6.98 (d, J=7.6 Hz, 1H), 6.65 (d, J=2.6 Hz, 1H), 4.34-4.23 (m, 1H), 3.62-3.52 (m, 1H), 3.44-3.35 (m, 1H), 3.29-3.16 (m, 1H), 2.50-2.28 (m, 5H), 2.21 (d, J=6.6 Hz, 3H), 2.11 (dd, J=17.5, 2.5 Hz, 1H), 1.94 (t, J=7.3 Hz, 3H), 1.87-1.78 (m, 1H), 1.27 (s, 3H).

$^{13}$C NMR (125 MHz, Methanol-d$_4$) δ 183.1, 176.7, 172.1, 141.9, 136.7, 133.8, 133.1, 131.5, 131.3, 130.8, 130.3, 127.9, 127.9, 126.9, 126.5, 75.9, 58.9, 53.2, 50.7, 41.7, 41.0, 22.4, 22.2, 17.1, 15.5.

LRMS (ESI+APCI) m/z: 512.1, HRMS (ESI) m/z: found: 512.1259, calcd 512.1245 for C$_{25}$H$_{28}$ClN$_3$NiO$_3{}^+$ [M+H]$^+$.

Example 83

Preparation of Nickel Chelate of 3-Aminopentanoic Acid

The preparation process was substantially the same as those in example 65. 3-amino-3-phenylpropionic acid was replaced by 3-aminopentanoic acid to obtain nickel chelate of 3-aminopentanoic acid in a yield of 94%.

mp=248-250° C. $[\alpha]^{20}{}_D$=−4370.5 (c=0.044, CHCl$_3$).

$^1$H NMR (600 MHz, Methanol-d$_4$) δ 8.18 (d, J=9.1 Hz, 1H), 7.59 (tdd, J=9.0, 5.2, 1.6 Hz, 2H), 7.55-7.50 (m, 1H), 7.46 (dt, J=7.0, 1.9 Hz, 1H), 7.28 (dd, J=9.1, 2.6 Hz, 1H), 6.92 (dd, J=7.6, 1.5 Hz, 1H), 6.62 (d, J=2.5 Hz, 1H), 4.22-4.10 (m, 1H), 3.61-3.52 (m, 1H), 3.37-3.32 (m, 2H), 3.26-3.12 (m, 1H), 2.52-2.14 (m, 7H), 1.93 (t, J=7.3 Hz, 3H), 1.87-1.77 (m, 1H), 1.27 (s, 3H), 1.19 (t, J=7.4 Hz, 3H).

$^{13}$C NMR (150 MHz, Methanol-d$_4$) δ 183.2, 176.8, 173.1, 142.2, 136.9, 134.0, 133.2, 131.7, 131.3, 130.6, 130.3, 128.8, 128.1, 126.8, 126.3, 75.8, 64.9, 53.3, 50.6, 41.6, 40.2, 30.6, 22.2, 17.2, 15.5, 11.9.

LRMS (ESI+APCI) m/z: 526.1, HRMS (ESI) m/z: found: 526.1408, calcd 526.1402 for C$_{26}$H$_{30}$ClN$_3$NiO$_3{}^+$ [M+H]$^+$.

Example 84

Preparation of Nickel Chelate of 3-Aminoheptanoic Acid

The preparation process was substantially the same as those in example 65. 3-amino-3-phenylpropionic acid was replaced by 3-aminoheptanoic acid to obtain nickel chelate of 3-aminoheptanoic acid in a yield of 97%.

mp=110-112° C. $[\alpha]^{20}{}_D$=−3400.0 (c=0.046, CHCl$_3$).

$^1$H NMR (400 MHz, Methanol-d$_4$) δ 8.17 (d, J=9.1 Hz, 1H), 7.65-7.42 (m, 4H), 7.29 (dd, J=9.1, 2.6 Hz, 1H), 6.96-6.86 (m, 1H), 6.61 (d, J=2.5 Hz, 1H), 4.18 (td, J=12.3, 6.7 Hz, 1H), 3.60-3.33 (m, 3H), 3.26-3.10 (m, 1H), 2.51-2.11 (m, 7H), 1.93 (t, J=7.3 Hz, 3H), 1.88-1.74 (m, 2H), 1.60-1.36 (m, 2H), 1.27 (s, 3H), 1.24-1.12 (m, 1H), 0.98 (t, J=7.4 Hz, 3H).

$^{13}$C NMR (125 MHz, Methanol-d$_4$) δ 181.5, 172.7, 170.7, 141.4, 135.6, 132.9, 132.6, 130.2, 129.7, 129.2, 127.6, 126.3, 125.5, 125.0, 74.1, 62.7, 52.9, 49.5, 40.8, 40.4, 36.8, 29.1, 22.9, 21.5, 16.8, 15.3, 14.1.

LRMS (ESI+APCI) m/z: 554.2, HRMS (ESI) m/z: found: 554.1720, calcd 554.1715 for $C_{28}H_{34}ClN_3NiO_3^+$ [M+H]$^+$.

Example 85

Preparation of Nickel Chelate of 3-Amino-5-Methylhexanoic Acid

The preparation process was substantially the same as those in example 65. 3-amino-3-phenylpropionic acid was replaced by 3-amino-5-methylhexanoic acid to obtain nickel chelate of 3-amino-5-methylhexanoic acid in a yield of 91%.

mp=248-251° C. $[\alpha]^{20}_D$=−3029.5 (c=0.044, CHCl$_3$).

$^1$H NMR (400 MHz, Methanol-d$_4$) δ 8.16 (d, J=9.1 Hz, 1H), 7.66-7.46 (m, 4H), 7.28 (dd, J=9.1, 2.6 Hz, 1H), 6.96 (dt, J=8.3, 1.4 Hz, 1H), 6.62 (d, J=2.6 Hz, 1H), 4.32-4.18 (m, 1H), 3.58-3.49 (m, 1H), 3.41-3.33 (m, 2H), 3.26-3.10 (m, 1H), 2.56-2.27 (m, 6H), 2.17 (dd, J=17.5, 2.5 Hz, 1H), 1.92 (t, J=7.3 Hz, 3H), 1.86-1.68 (m, 2H), 1.27 (s, 3H), 0.96 (d, J=6.6 Hz, 3H), 0.73 (d, J=6.5 Hz, 3H).

$^{13}$C NMR (125 MHz, CDCl$_3$) δ 181.5, 172.7, 170.5, 141.4, 135.5, 133.0, 132.6, 130.3, 130.2, 129.6, 129.2, 127.8, 126.4, 125.5, 125.0, 74.1, 60.6, 52.8, 49.6, 46.4, 40.8, 40.3, 25.1, 22.8, 22.8, 21.4, 16.8, 15.3.

LRMS (ESI+APCI) m/z: 554.2, HRMS (ESI) m/z: found: 554.1728, calcd 554.1715 for $C_{28}H_{34}ClN_3NiO_3^+$ [M+H]$^+$.

Example 86

Preparation of Nickel Chelate of 3-Amino-4-Methylpentanoic Acid

The preparation process was substantially the same as those in example 65. 3-amino-3-phenylpropionic acid was replaced by 3-amino-4-methylpentanoic acid to obtain nickel chelate of 3-amino-4-methylpentanoic acid in a yield of 76%.

mp=150-152° C. $[\alpha]^{20}_D$=−3242.9 (c=0.042, CHCl$_3$).

$^1$H NMR (400 MHz, Methanol-d$_4$) δ 8.18 (d, J=9.1 Hz, 1H), 7.66-7.42 (m, 4H), 7.29 (dd, J=9.1, 2.6 Hz, 1H), 6.90 (dt, J=7.6, 1.0 Hz, 1H), 6.60 (d, J=2.6 Hz, 1H), 4.27-4.03 (m, 2H), 3.37-3.32 (m, 1H), 3.23-3.09 (m, 1H), 2.99 (dt, J=10.3, 3.3 Hz, 1H), 2.51-2.24 (m, 6H), 1.93 (t, J=7.3 Hz, 3H), 1.88-1.76 (m, 1H), 1.35 (d, J=6.7 Hz, 3H), 1.27 (s, 3H), 0.91 (d, J=6.6 Hz, 3H).

$^{13}$C NMR (125 MHz, CDCl$_3$) δ 181.5, 173.0, 170.7, 141.5, 135.8, 133.0, 132.6, 130.2, 129.6, 129.3, 127.8, 126.3, 125.6, 125.0, 74.0, 69.3, 53.1, 49.5, 40.6, 38.4, 34.0, 21.6, 21.3, 19.9, 17.0, 15.3.

LRMS (ESI+APCI) m/z: 540.1, HRMS (ESI) m/z: found: 540.1556, calcd 540.1558 for $C_{27}H_{32}ClN_3NiO_3^+$ [M+H]$^+$.

Example 87

Preparation of Nickel Chelate of 3-Amino-3-Cyclopropylpropionic Acid

The preparation process was substantially the same as those in example 65. 3-amino-3-phenylpropionic acid was replaced by 3-amino-3-cyclopropylpropionic acid to obtain nickel chelate of 3-amino-3-cyclopropylpropionic acid in a yield of 93%.

mp=150-151° C. $[\alpha]^{20}_D$=−3892.1 (c=0.038, CHCl$_3$).

$^1$H NMR (600 MHz, Methanol-d$_4$) δ 8.18 (dd, J=9.3, 2.9 Hz, 1H), 7.61-7.24 (m, 5H), 6.92 (d, J=7.7 Hz, 1H), 6.58 (d, J=2.6 Hz, 1H), 4.42-4.29 (m, 1H), 4.18-4.02 (m, 1H), 3.42-3.33 (m, 1H), 3.18-3.06 (m, 1H), 2.97-2.85 (m, 1H), 2.56-2.25 (m, 6H), 2.02-1.82 (m, 4H), 1.26 (s, 3H), 1.20-1.12 (m, 1H), 0.85-0.73 (m, 1H), 0.24-0.14 (m, 1H), 0.08-−0.03 (m, 1H).

$^{13}$C NMR (150 MHz, Methanol-d$_4$) δ 183.2, 177.1, 171.8, 142.1, 136.5, 133.9, 133.2, 131.7, 131.4, 130.6, 130.3, 128.8, 128.1, 126.9, 126.4, 75.9, 69.0, 53.4, 50.6, 41.9, 40.3, 22.2, 18.2, 16.9, 15.5, 6.2, 5.4.

LRMS (ESI+APCI) m/z: 538.1, HRMS (ESI) m/z: found: 538.1413, calcd 538.1402 for $C_{27}H_{30}ClN_3NiO_3^+$ [M+H]$^+$.

Example 88

Preparation of Nickel Chelate of 3-Amino-3-Cyclohexylpropionic Acid

The preparation process was substantially the same as those in example 65. 3-amino-3-phenylpropionic acid was replaced by 3-amino-3-cyclohexylpropionic acid to obtain nickel chelate of 3-amino-3-cyclohexylpropionic acid in a yield of 85%.

mp=155-157° C. $[\alpha]^{20}_D$=−2770.0 (c=0.04, CHCl$_3$).

$^1$H NMR (400 MHz, Methanol-d$_4$) δ 8.17 (d, J=9.1 Hz, 1H), 7.63-7.42 (m, 4H), 7.28 (dd, J=9.1, 2.6 Hz, 1H), 6.95-6.86 (m, 1H), 6.58 (d, J=2.6 Hz, 1H), 4.27-4.13 (m, 1H), 4.04-3.88 (m, 1H), 3.39-3.33 (m, 1H), 3.24-3.13 (m, 1H), 3.09-3.00 (m, 1H), 2.64-2.25 (m, 7H), 1.99 (d, J=13.1 Hz, 1H), 1.91 (t, J=7.3 Hz, 3H), 1.86-1.70 (m, 5H), 1.52-1.38 (m, 1H), 1.27 (s, 3H), 1.17-1.09 (m, 1H), 0.81-0.59 (m, 2H).

$^{13}$C NMR (125 MHz, CDCl$_3$) δ 181.4, 173.3, 170.7, 141.5, 135.7, 133.0, 132.6, 130.3, 130.2, 129.6, 129.2, 128.0, 126.3, 125.6, 124.9, 74.2, 68.1, 52.8, 49.6, 43.1, 40.6, 37.7, 31.3, 29.8, 26.4, 26.3, 26.0, 21.5, 16.7, 15.3.

LRMS (ESI+APCI) m/z: 580.2, HRMS (ESI) m/z: found: 580.1876, calcd 580.1871 for $C_{30}H_{36}ClN_3NiO_3^+$ [M+H]$^+$.

Example 89

Preparation of Nickel Chelate of 3-amino-4-(2,4,5-trifluorophenyl)butanoic Acid

The preparation process was substantially the same as those in example 65. 3-amino-3-phenylpropionic acid was replaced by 3-amino-4-(2,4,5-trifluorophenyl)butanoic acid to obtain nickel chelate of 3-amino-4-(2,4,5-trifluorophenyl) butanoic acid in a yield of 87%.

mp=140-141° C. $[\alpha]^{20}_D$=−2814.0 (c=0.05, CHCl$_3$).

$^1$H NMR (500 MHz, Methanol-d$_4$) δ 8.15 (d, J=9.1 Hz, 1H), 7.62-7.48 (m, 2H), 7.46-7.34 (m, 2H), 7.28 (dd, J=9.1, 2.5 Hz, 1H), 7.12 (td, J=9.9, 6.6 Hz, 1H), 7.03 (ddd, J=10.7, 8.7, 6.7 Hz, 1H), 6.59 (d, J=2.6 Hz, 1H), 6.49-6.38 (m, 1H), 4.38 (dd, J=13.8, 6.9 Hz, 1H), 4.20 (ddd, J=13.4, 11.4, 5.7 Hz, 1H), 4.01-3.91 (m, 1H), 3.62 (tdd, J=6.9, 4.3, 2.5 Hz, 1H), 3.51-3.33 (m, 2H), 2.58-2.28 (m, 5H), 2.09 (dd, J=17.6, 2.6 Hz, 1H), 2.01 (t, J=7.3 Hz, 3H), 1.89-1.78 (m, 1H), 1.31 (s, 3H).

$^{13}$C NMR (125 MHz, Methanol-d$_4$) δ 183.4, 176.4, 173.6, 157.6 (ddd, J=245.1, 9.5, 2.2 Hz), 150.6 (dt, J=250.2, 13.8 Hz), 148.07 (ddd, J=244.1, 12.5, 3.1 Hz), 142.2, 136.5, 134.0, 133.4, 131.3, 131.0, 130.4, 130.2, 128.0, 127.8, 126.8, 126.6, 122.1 (dt, J=18.6, 5.0 Hz), 120.0 (dd, J=19.3, 5.9 Hz), 106.9 (dd, J=28.9, 21.2 Hz), 75.7, 64.0, 53.2, 50.9, 41.4, 39.2, 35.9, 22.6, 18.0, 15.6.

LRMS (ESI+APCI) m/z: 642.1, HRMS (ESI) m/z: found: 642.1287, calcd 642.1276 for $C_{31}H_{29}ClF_3N_3NiO_3^+$ [M+H]$^+$.

Example 90 Nickel (II)-(S)—N-(2-benzoyl-4-chlorophenyl)-1-(3,4-dichlorobenzyl)-2-methylpyrrolyl-2-carboxamide/(S)-2-amino-2-benzylacetic acid— Schiff Base Complex Synthesis method: ligand (S)—N-(2-benzoyl-4-chlorophenyl)-1-(3,4-dichlorobenzyl)-2-methylpyrrolyl-2-carboxamide (100.3 mg, 0.2 mmol), DL-phenylalanine (33 mg, 0.2 mmol) and anhydrous nickel acetate (35.3 mg, 0.2 mmol) were dissolved in 4 mL methanol and DBU (149.4 μL, 1.0 mmol) was added and reacted at 60° C. for 72 h. 5% of glacial acetic acid was added to quench the reaction. The mixture was extracted three times with dichloromethane and the combined organic lays were dried, evaporated under reduced pressure to remove solvent and purified by column chromatography (dichloromethane:methanol=20:1) to obtain red solids (136 mg in a yield of 98%).

mp: 116.3-117.5° C. $[\alpha]^{20}_D$=2502 (c=1, CHCl$_3$).

$^1$H NMR (400 MHz, CDCl$_3$) δ 9.08 (d, J=2.1 Hz, 1H), 8.32 (d, J=9.3 Hz, 1H), 7.61-7.49 (m, 3H), 7.42-7.27 (m, 6H), 7.15-7.02 (m, 3H), 6.65 (d, J=7.7 Hz, 1H), 6.61 (d, J=2.6 Hz, 1H), 4.22 (t, J=5.2 Hz, 1H), 3.54 (dd, J=59.9, 13.0 Hz, 2H), 3.36-3.24 (m, 1H), 3.14 (dt, J=17.6, 6.8 Hz, 2H), 2.78 (dd, J=13.8, 5.4 Hz, 1H), 2.42-2.23 (m, 1H), 2.14-2.03 (m, 1H), 1.98 (dd, J=19.7, 9.7 Hz, 1H), 1.87-1.73 (m, 1H), 1.33 (s, 3H).

$^{13}$C NMR (125 MHz, CDCl$_3$) δ 180.5, 178.1, 170.8, 141.5, 135.8, 134.0, 133.4, 133.1, 133.0, 132.7, 132.6, 131.1, 130.5, 130.3, 129.8, 129.5, 129.3, 129.1, 127.9, 127.7, 127.5, 125.8, 124.3, 74.3, 71.8, 57.3, 54.7, 41.4, 39.8, 20.7, 17.8.

MS (ESI, m/z): 704.0 [M−H]$^-$.

Example 91 Nickel (II)-(R)—N-(2-benzoyl-4-chlorophenyl)-1-(3,4-dichlorobenzyl)-2-methylpyrrolyl-2-carboxamide/(R)-2-amino-2-(3-methoxybenzyl) acetic acid—Schiff Base Complex Synthesis method: ligand (R)—N-(2-benzoyl-4-chlorophenyl)-1-(3,4-dichloro benzyl)-2-methylpyrrolyl-2-carboxamide (100.3 mg, 0.2 mmol), DL-3-methoxyphenyl alanine 2-23 (39 mg, 0.2 mmol) and anhydrous nickel acetate (35.3 mg, 0.2 mmol) were dissolved in 4 mL methanol and K$_2$CO$_3$ (138.1 mg, 1.0 mmol) was added and reacted at 60° C. for 24 h. 5% of glacial acetic acid was added to quench the reaction. The mixture was extracted three times with dichloromethane. The combined organic lays were dried, evaporated under reduced pressure to remove solvent and purified by column chromatography (dichloromethane:methanol=20:1) to obtain red solids (132 mg in a yield of 90%).

mp: 104.2-106.1° C. $[\alpha]^{20}_D$=−2923 (c=1, CHCl$_3$).

$^1$H NMR (400 MHz, CDCl$_3$) δ 9.08 (d, J=2.0 Hz, 1H), 8.33 (d, J=9.3 Hz, 1H), 7.62-7.47 (m, 3H), 7.40-7.28 (m, 3H), 7.26-7.18 (m, 1H), 7.12 (dd, J=9.3, 2.6 Hz, 1H), 6.88 (dd, J=8.3, 2.3 Hz, 1H), 6.67 (d, J=7.5 Hz, 1H), 6.60 (d, J=2.6 Hz, 2H), 6.55 (d, J=7.9 Hz, 1H), 4.21 (t, J=5.3 Hz, 1H), 3.65 (s, 3H), 3.55 (dd, J=59.3, 13.1 Hz, 2H), 3.45-3.31 (m, 1H), 3.26-3.03 (m, 2H), 2.81 (dd, J=13.8, 5.1 Hz, 1H), 2.46 (dq, J=14.1, 7.2 Hz, 1H), 2.25-2.11 (m, 1H), 2.07-1.96 (m, 1H), 1.95-1.78 (m, 1H), 1.35 (s, 3H).

$^{13}$C NMR (125 MHz, CDCl$_3$) δ 180.6, 178.3, 170.9, 141.5, 135.8, 135.7, 134.0, 133.4, 133.1, 133.0, 132.7, 132.6, 131.1, 130.3, 129.8, 129.6, 129.5, 129.3, 127.7, 127.4, 126.4, 125.8, 124.3, 124.3, 74.4, 71.3, 57.4, 54.8, 41.5, 34.1, 20.9, 17.9.

MS (ESI, m/z): 734.0 [M−H]$^-$.

Example 92 Nickel (II)-(R)—N-(2-benzoyl-4-chlorophenyl)-1-(3,4-dichlorobenzyl)-2-methylpyrrolyl-2-carboxamide/(R)-2-amino-2-(3-methylbenzyl) acetic acid—Schiff Base Complex According to a synthesis procedure similar to example 91, DL-3-methoxyphenyl alanine was replaced by DL-3-methylphenylalanine and red solids in a yield of 88% were obtained by column chromatography (dichloromethane:methanol=20:1).

mp: 105.3-106.8° C. $[\alpha]^{20}_D$=−1898 (c=1, CHCl$_3$).

$^1$H NMR (400 MHz, CDCl$_3$) δ 9.06 (d, J=1.5 Hz, 1H), 8.34 (d, J=9.3 Hz, 1H), 7.55 (dt, J=17.5, 7.4 Hz, 3H), 7.38 (t, J=7.5 Hz, 1H), 7.31 (t, J=6.7 Hz, 2H), 7.23 (t, J=7.5 Hz, 1H), 7.17-7.09 (m, 2H), 6.87 (d, J=7.8 Hz, 2H), 6.63 (dd, J=12.2, 5.1 Hz, 2H), 4.21 (t, J=5.1 Hz, 1H), 3.53 (dd, J=47.7, 13.1 Hz, 2H), 3.31 (td, J=12.6, 5.8 Hz, 1H), 3.11 (dd, J=13.7, 4.7 Hz, 2H), 2.75 (dd, J=13.7, 5.4 Hz, 1H), 2.47-2.31 (m, 1H), 2.27 (s, 3H), 2.13-2.06 (m, 1H), 1.99 (dd, J=19.4, 9.7 Hz, 1H), 1.84 (dt, J=14.9, 6.7 Hz, 1H), 1.33 (s, 3H).

$^{13}$C NMR (125 MHz, CDCl$_3$) δ 180.4, 178.2, 170.7, 141.5, 138.7, 135.8, 135.6, 134.0, 133.3, 133.1, 133.0, 132.6, 132.6, 131.3, 131.1, 130.2, 129.8, 129.5, 129.2, 128.9, 128.4, 127.9, 127.7, 127.5, 127.5, 125.7, 124.2, 74.3, 71.8, 57.3, 54.7, 41.2, 39.8, 21.6, 20.6, 17.8.

MS (ESI, m/z): 718.0 [M−H]$^-$.

Example 93 Nickel (II)-(R)—N-(2-benzoyl-4-chlorophenyl)-1-(3,4-dichlorobenzyl)-2-methylpyrrolyl-2-carboxamide/(R)-2-amino-2-(4-fluorobenzyl)acetic acid—Schiff Base Complex C4

According to a synthesis procedure similar to example 91, DL-3-methoxyphenyl alanine was replaced by DL-4-fluorophenylalanine and red solids in a yield of 76% was obtained by column chromatography (dichloromethane:methanol=20:1).

mp: 235-236.8° C. $[\alpha]^{20}_D$=−2300 (c=1, CHCl$_3$).

$^1$H NMR (400 MHz, CDCl$_3$) δ 9.06 (d, J=1.5 Hz, 1H), 8.32 (d, J=9.3 Hz, 1H), 7.56 (p, J=7.5 Hz, 3H), 7.43 (t, J=7.3 Hz, 1H), 7.37-7.28 (m, 2H), 7.13 (dd, J=9.3, 2.5 Hz, 1H), 7.05 (d, J=7.0 Hz, 4H), 6.73 (d, J=7.5 Hz, 1H), 6.62 (d, J=2.5 Hz, 1H), 4.21 (t, J=5.0 Hz, 1H), 3.54 (dd, J=47.7, 13.0 Hz, 2H), 3.34 (td, J=12.6, 6.0 Hz, 1H), 3.20-3.01 (m, 2H), 2.74 (dd, J=14.0, 5.4 Hz, 1H), 2.45-2.26 (m, 1H), 2.26-2.12 (m, 1H), 2.00 (dd, J=19.3, 9.6 Hz, 1H), 1.90-1.83 (m, 1H), 1.35 (s, 3H).

$^{13}$C NMR (125 MHz, CDCl$_3$) δ 180.5, 177.9, 170.9, 163.4, 161.8, 141.5, 135.7, 133.9, 133.3, 133.1, 133.0, 132.7, 132.6, 131.9, 131.9, 131.5, 131.5, 131.1, 130.4, 129.8, 129.6, 129.3, 127.7, 127.6, 127.4, 125.9, 124.3, 116.0, 115.8, 74.3, 71.6, 57.4, 54.6, 41.2, 38.8, 20.7, 17.8.

MS (ESI, m/z): 722.0 [M−H]$^-$.

Example 94 Nickel (II)-(R)—N-(2-benzoyl-4-chlorophenyl)-1-(3,4-dichlorobenzyl)-2-methylpyrrolyl-2-carboxamide/(R)-2-amino-2-(3-methoxyphenyl) acetic acid—Schiff Base Complex According to a synthesis procedure similar to example 91, DL-3-methoxyphenyl alanine was replaced by DL-3-methoxyphenylglycine and red solids in a yield of 70% were obtained by column chromatography (dichloromethane:methanol=20:1).

mp: 134.8-136.6° C. $[\alpha]^{20}_D$=−2183 (c=1, CHCl$_3$).

$^1$H NMR (400 MHz, CDCl$_3$) δ 9.18 (d, J=1.6 Hz, 1H), 8.23 (d, J=9.3 Hz, 1H), 7.79 (d, J=8.2 Hz, 1H), 7.54 (t, J=7.6 Hz, 1H), 7.39 (dd, J=15.2, 7.2 Hz, 3H), 7.29 (d, J=7.5 Hz, 1H), 7.22 (t, J=7.9 Hz, 1H), 7.16 (dd, J=9.3, 2.5 Hz, 1H), 7.11-7.02 (m, 2H), 6.80 (dd, J=8.2, 2.3 Hz, 1H), 6.66 (d, J=2.5 Hz, 1H), 6.14 (d, J=7.9 Hz, 1H), 4.71 (s, 1H), 4.08-3.95 (m, 1H), 3.80 (d, J=13.0 Hz, 1H), 3.71 (s, 3H), 3.61 (d, J=13.0 Hz, 1H), 3.34 (t, J=8.9 Hz, 1H), 3.14 (dd,

J=18.8, 9.9 Hz, 1H), 2.46 (dd, J=14.1, 9.9 Hz, 1H), 2.19 (dd, J=17.6, 7.9 Hz, 2H), 1.76 (s, 1H), 1.49 (s, 3H).

$^{13}$C NMR (125 MHz, CDCl$_3$) δ 180.8, 177.4, 171.7, 159.8, 141.3, 139.2, 135.8, 134.0, 133.3, 133.3, 133.1, 132.6, 132.4, 131.2, 130.0, 129.9, 129.7, 129.0, 128.9, 127.7, 127.1, 126.7, 126.0, 124.9, 118.4, 113.8, 112.6, 74.7, 74.4, 57.3, 55.4, 55.3, 41.7, 21.2, 18.3.

MS (ESI, m/z): 720.0 [M–H]$^-$.

Example 95 Nickel (II)-(R)—N-(2-benzoyl-4-chlorophenyl)-1-(3,4-dichlorobenzyl)-2-methylpyrrolyl-2-carboxamide/(R)-2-amino-2-(3-bromophenyl)acetic acid—Schiff Base Complex According to a synthesis procedure similar to example 91, DL-3-methoxyphenyl alanine was replaced by DL-3-bromophenylglycine and red solids in a yield of 85% were obtained by column chromatography (dichloromethane:methanol=20:1).

mp: 102.5-104.4° C. [α]$^{20}_D$=–2069 (c=1, CHCl$_3$).

$^1$H NMR (400 MHz, CDCl$_3$) δ 9.18 (d, J=2.1 Hz, 1H), 8.22 (d, J=9.3 Hz, 1H), 8.15 (s, 1H), 7.80 (dd, J=8.2, 2.2 Hz, 1H), 7.57 (t, J=7.6 Hz, 1H), 7.50-7.38 (m, 3H), 7.32 (dd, J=18.2, 7.8 Hz, 2H), 7.15 (ddd, J=24.1, 12.7, 5.5 Hz, 3H), 6.67 (d, J=2.5 Hz, 1H), 6.13 (d, J=7.8 Hz, 1H), 4.71 (s, 1H), 4.04 (t, J=10.9 Hz, 1H), 3.72 (dd, J=78.9, 13.1 Hz, 2H), 3.41-3.29 (m, 1H), 3.14 (dd, J=21.0, 13.1 Hz, 1H), 2.50 (dd, J=13.7, 10.0 Hz, 1H), 2.30-2.04 (m, 2H), 1.58 (s, 1H), 1.50 (s, 3H), 1.25 (s, 1H).

$^{13}$C NMR (125 MHz, CDCl$_3$) δ 180.8, 176.8, 172.1, 141.4, 139.9, 135.8, 134.0, 133.4, 132.9, 132.9, 132.4, 131.6, 131.3, 130.3, 130.2, 130.0, 129.3, 129.3, 129.1, 127.6, 127.0, 126.7, 126.1, 125.3, 125.0, 122.9, 74.5, 74.1, 57.3, 55.3, 41.8, 21.2, 18.3.

MS (ESI, m/z): 769.7 [M–H]$^-$.

Example 96 Nickel (II)-(R)—N-(2-benzoyl-4-chlorophenyl)-1-(3,4-dichloro benzyl)-2-methylpyrrolyl-2-carboxamide/(R)-2-amino-3-(3,5-diiodo-4-hydroxyphenyl)propionic acid—Schiff Base Complex According to a synthesis procedure similar to example 91, DL-3-methoxyphenylalanine was replaced by DL-2-amino-3-(3,5-diiodo-4-hydroxy phenyl)propionic acid and red solids in a yield of 90% were obtained by column chromatography (dichloromethane:methanol=20:1).

mp: 286.5-287.9° C. [α]$^{20}_D$=2038 (c=1, CHCl$_3$).

1H NMR (400 MHz, CDCl$_3$) δ 9.05 (d, J=2.0 Hz, 1H), 8.43 (d, J=9.3 Hz, 1H), 7.66-7.53 (m, 3H), 7.47 (dd, J=10.8, 5.7 Hz, 1H), 7.33 (t, J=7.2 Hz, 2H), 7.27 (s, 2H), 7.16 (dd, J=9.3, 2.6 Hz, 1H), 6.78 (d, J=7.4 Hz, 1H), 6.66 (d, J=2.5 Hz, 1H), 5.82 (s, 1H), 4.14-4.07 (m, 1H), 3.56 (dd, J=29.2, 13.0 Hz, 2H), 3.46-3.34 (m, 1H), 3.17 (t, J=8.8 Hz, 1H), 2.89 (dd, J=14.1, 4.4 Hz, 1H), 2.67 (dd, J=13.9, 6.2 Hz, 1H), 2.54-2.39 (m, 1H), 2.24 (dd, J=13.8, 9.8 Hz, 1H), 2.02 (td, J=18.7, 9.4 Hz, 2H), 1.37 (s, 3H).

$^{13}$C NMR (125 MHz, CDCl$_3$) δ 180.4, 177.6, 171.0, 153.4, 141.8, 140.6, 135.7, 134.0, 133.2, 133.1, 133.0, 132.6, 131.8, 131.2, 130.6, 129.8, 129.7, 129.4, 127.6, 127.5, 127.4, 125.8, 124.4, 82.8, 74.4, 71.2, 57.5, 54.7, 41.0, 38.0, 21.0, 17.9.

MS (ESI, m/z): 971.8 [M–H]$^-$.

Example 97 Nickel (II)-(R)—N-(2-benzoyl-4-chlorophenyl)-1-(3,4-dichloro benzyl)-2-methylpyrrolyl-2-carboxamide/(R)-2-amino-3-(naphth-1-yl)propionic acid—Schiff Base Complex According to a synthesis procedure similar to example 91, DL-3-methoxyphenyl alanine was replaced by DL-2-amino-3-(naphth-1-yl)propionic acid and red solids in a yield of 92% were obtained by column chromatography (dichloromethane:methanol=20:1).

mp: 114.5-116.1° C. [α]$^{20}_D$=–1812 (c=1, CHCl$_3$).

$^1$H NMR (400 MHz, CDCl$_3$) δ 9.09 (d, J=2.0 Hz, 1H), 8.30 (d, J=9.3 Hz, 1H), 7.78 (t, J=8.0 Hz, 2H), 7.68 (dd, J=8.2, 2.0 Hz, 1H), 7.57 (d, J=8.6 Hz, 1H), 7.43-7.35 (m, 1H), 7.30 (dd, J=15.6, 7.6 Hz, 4H), 7.23-7.11 (m, 3H), 7.08 (dd, J=9.3, 2.6 Hz, 1H), 6.68 (t, J=7.6 Hz, 1H), 6.44 (d, J=2.6 Hz, 1H), 5.64 (d, J=7.7 Hz, 1H), 4.41 (dd, J=8.3, 4.3 Hz, 1H), 4.07 (dd, J=14.2, 8.5 Hz, 1H), 3.79 (dd, J=14.1, 4.3 Hz, 1H), 3.70 (d, J=13.2 Hz, 1H), 3.61 (td, J=13.1, 5.9 Hz, 1H), 3.46 (d, J=13.2 Hz, 1H), 3.24 (t, J=9.1 Hz, 1H), 2.83-2.53 (m, 1H), 2.39-2.22 (m, 1H), 2.12 (dd, J=19.8, 9.6 Hz, 1H), 2.00 (dt, J=15.0, 8.9 Hz, 1H), 1.40 (s, 3H).

$^{13}$C NMR (125 MHz, CDCl$_3$) δ 180.3, 178.3, 170.5, 141.3, 135.8, 134.2, 133.8, 133.3, 133.0, 132.8, 132.6, 132.5, 132.3, 131.7, 131.2, 129.8, 129.6, 128.8, 128.7, 128.6, 128.6, 128.5, 127.7, 127.5, 127.4, 126.5, 126.1, 125.7, 125.6, 124.1, 123.4, 74.4, 71.6, 56.9, 55.1, 41.6, 40.2, 20.9, 17.9.

MS (ESI, m/z): 75.0 [M–H]$^-$.

Example 98 Nickel (II)-(R)—N-(2-benzoyl-4-chlorophenyl)-1-(3,4-dichloro benzyl)-2-methylpyrrolyl-2-carboxamide/(R)-2-amino-3-(benzothiophen-3-yl)propionic acid—Schiff Base Complex According to a synthesis procedure similar to example 91, DL-3-methoxyphenylalanine was replaced by DL-2-amino-3-(benzothiophen-3-yl) propionic acid and red solids in a yield of 94% were obtained by column chromatography (dichloromethane:methanol=20:1).

mp: 127.1-128.9° C. [α]$^{20}_D$=–1836 (c=1, CHCl$_3$).

$^1$H NMR (400 MHz, CDCl$_3$) δ 9.06 (d, J=2.0 Hz, 1H), 8.34 (d, J=9.3 Hz, 1H), 7.86 (d, J=8.0 Hz, 1H), 7.57 (dd, J=8.2, 2.0 Hz, 1H), 7.49 (t, J=7.5 Hz, 1H), 7.45-7.34 (m, 2H), 7.30 (dd, J=11.9, 6.2 Hz, 3H), 7.19-7.08 (m, 4H), 6.59 (d, J=2.6 Hz, 1H), 6.48 (d, J=7.5 Hz, 1H), 4.31 (t, J=5.5 Hz, 1H), 3.71-3.59 (m, 1H), 3.51 (dd, J=57.6, 9.8 Hz, 2H), 3.18 (dd, J=14.5, 4.7 Hz, 1H), 3.03 (dt, J=19.1, 10.3 Hz, 2H), 2.01 (ddd, J=20.7, 18.6, 11.3 Hz, 3H), 1.81-1.69 (m, 1H), 1.30 (s, 3H).

$^{13}$C NMR (125 MHz, CDCl$_3$) δ 180.3, 178.3, 170.8, 141.5, 140.6, 139.3, 135.7, 133.9, 133.2, 133.0, 132.9, 132.7, 131.1, 130.5, 130.1, 129.8, 129.3, 129.0, 127.5, 127.5, 125.9, 125.8, 124.8, 124.5, 124.3, 122.9, 122.1, 74.3, 70.9, 57.2, 54.8, 41.0, 34.0, 20.4, 17.8.

MS (ESI, m/z): 760.0 [M–H]$^-$.

Example 99 Nickel (II)-(R)—N-(2-benzoyl-4-chlorophenyl)-1-(3,4-dichloro benzyl)-2-methylpyrrolyl-2-carboxamide/(R)-2-amino-3-(thiophen-3-yl)propionic acid—Schiff Base Complex According to a synthesis procedure similar to example 91, DL-3-methoxyphenylalanine was replaced by DL-2-amino-3-(thiophen-3-yl)propionic acid and red solids in a yield of 89% were obtained by column chromatography (dichloromethane:methanol=20:1).

mp: 208.5-209.6° C. [α]$^{20}_D$=–2419 (c=1, CHCl$_3$).

$^1$H NMR (400 MHz, CDCl$_3$) δ 9.09 (d, J=2.1 Hz, 1H), 8.34 (d, J=9.3 Hz, 1H), 7.63-7.49 (m, 3H), 7.46-7.39 (m, 1H), 7.38-7.28 (m, 3H), 7.13 (dd, J=9.3, 2.6 Hz, 1H), 7.04 (d, J=1.8 Hz, 1H), 6.86 (dd, J=4.9, 1.2 Hz, 1H), 6.70 (d, J=7.7 Hz, 1H), 6.62 (d, J=2.6 Hz, 1H), 4.18 (t, J=5.1 Hz, 1H), 3.63 (d, J=13.1 Hz, 1H), 3.50 (dq, J=11.9, 5.9 Hz, 2H), 3.25-3.05 (m, 2H), 2.77 (dd, J=14.3, 5.4 Hz, 1H), 2.62-2.41 (m, 1H), 2.29-2.12 (m, 1H), 2.09-1.98 (m, 1H), 1.96-1.84 (m, 1H), 1.36 (s, 3H).
$^{13}$C NMR (125 MHz, CDCl$_3$) δ 180.6, 178.3, 170.9, 141.5, 135.8, 135.7, 134.0, 133.4, 133.1, 133.0, 132.7, 132.6, 131.1, 130.3, 129.8, 129.6, 129.5, 129.3, 127.7, 127.4, 126.4, 125.8, 124.3, 124.3, 74.4, 71.3, 57.4, 54.8, 41.5, 34.1, 20.9, 17.9.
MS (ESI, m/z): 710.0 [M−H]$^-$.

Example 100 Nickel (II)-(S)—N-(2-benzoyl-4-chlorophenyl)-1-(3,4-dichloro benzyl)-2-methylpyrrolyl-2-carboxamide/(S)-2-amino-2-cyclobutylacetic acid—Schiff Base Complex According to a synthesis procedure similar to example 91, DL-3-methoxyphenyl alanine was replaced by DL-2-amino-2-cyclobutylacetic acid and red solids in a yield of 85% were obtained by column chromatography (dichloromethane:methanol=20:1).
mp: 307.5-308.9° C. [α]$^{20}_D$=3252 (c=1, CHCl$_3$).
$^1$H NMR (400 MHz, CDCl$_3$) δ 9.12 (s, 1H), 8.23 (d, J=9.3 Hz, 1H), 7.70 (d, J=8.2 Hz, 1H), 7.60-7.38 (m, 3H), 7.29 (t, J=6.9 Hz, 2H), 7.09 (dd, J=9.3, 2.5 Hz, 1H), 6.87 (d, J=7.4 Hz, 1H), 6.58 (d, J=2.5 Hz, 1H), 4.21-3.95 (m, 1H), 3.82-3.69 (m, 2H), 3.51 (d, J=13.0 Hz, 1H), 3.40 (t, J=8.7 Hz, 1H), 3.17-2.88 (m, 1H), 2.67 (dq, J=17.3, 8.7 Hz, 1H), 2.58-2.33 (m, 3H), 2.29-2.12 (m, 2H), 2.09-1.96 (m, 1H), 1.81 (dd, J=18.1, 8.2 Hz, 1H), 1.70 (dd, J=18.3, 9.0 Hz, 2H), 1.44 (s, 3H).
$^{13}$C NMR (125 MHz, CDCl$_3$) δ 180.3, 177.2, 169.6, 140.9, 135.8, 133.9, 133.3, 133.1, 133.0, 132.5, 132.3, 131.1, 130.3, 129.8, 129.4, 129.1, 128.1, 128.0, 127.8, 125.8, 124.2, 74.5, 74.0, 57.2, 55.0, 41.9, 40.7, 26.0, 25.6, 20.7, 18.1, 17.5.
MS (ESI, m/z): 668.0 [M−H]$^-$.

Example 101 Nickel (II)-(R)—N-(2-benzoyl-4-chlorophenyl)-1-(3,4-dichloro benzyl)-2-methylpyrrolyl-2-carboxamide/(R)-2-amino-4,4,4-trifluorobutanoic acid—Schiff Base Complex According to a synthesis procedure similar to example 91, DL-3-methoxyphenylalanine was replaced by DL-2-amino-4,4,4-trifluorobutanoic acid and red solids in a yield of 92% were obtained by column chromatography (dichloromethane:methanol=20:1).
mp: 274.0-276.0° C. [α]$^{20}_D$=−3150 (c=1, CHCl$_3$).
$^1$H NMR (400 MHz, CDCl$_3$) δ 9.16 (d, J=1.8 Hz, 1H), 8.35 (d, J=9.3 Hz, 1H), 7.68-7.47 (m, 4H), 7.36 (d, J=8.1 Hz, 1H), 7.30 (d, J=6.8 Hz, 1H), 7.16 (dd, J=9.3, 2.5 Hz, 1H), 6.90 (d, J=7.4 Hz, 1H), 6.60 (d, J=2.5 Hz, 1H), 4.16 (ddd, J=10.3, 9.3, 4.7 Hz, 2H), 3.74-3.49 (m, 2H), 3.38 (t, J=8.7 Hz, 1H), 3.09-2.80 (m, 1H), 2.63-2.46 (m, 1H), 2.42 (dd, J=13.7, 9.8 Hz, 1H), 2.23-2.09 (m, 2H), 2.06-1.90 (m, 1H), 1.44 (s, 3H).
$^{13}$C NMR (125 MHz, CDCl$_3$) δ 180.5, 177.2, 172.4, 141.9, 135.8, 134.0, 133.2, 133.2, 133.2, 133.1, 132.5, 131.3, 130.8, 129.9, 129.8, 129.7, 127.6, 127.6, 126.8, 125.8, 124.6, 74.9, 64.5, 57.8, 54.8, 41.2, 35.7, 35.5, 20.3, 17.4.
MS (ESI, m/z): 696.0 [M−H]$^-$.

Example 102 Nickel (II)-(R)—N-(2-benzoyl-4-chlorophenyl)-1-(3,4-dichloro benzyl)-2-methylpyrrolyl-2-carboxamide/(R)-2-aminopentanoic acid—Schiff Base Complex According to a synthesis procedure similar to example 91, DL-3-methoxyphenyl alanine was replaced by DL-2-aminopentanoic acid and red solids in a yield of 90% were obtained by column chromatography (dichloromethane:methanol=20:1).
mp: 277.8-228.9° C. [α]$^{20}_D$=−2430 (c=1, CHCl$_3$).
$^1$H NMR (400 MHz, CDCl$_3$) δ 9.11 (d, J=2.0 Hz, 1H), 8.21 (d, J=9.3 Hz, 1H), 7.73 (dd, J=8.2, 2.0 Hz, 1H), 7.61-7.49 (m, 2H), 7.46 (t, J=7.4 Hz, 1H), 7.31 (dd, J=15.9, 7.6 Hz, 2H), 7.12 (dd, J=9.3, 2.6 Hz, 1H), 6.86 (d, J=7.5 Hz, 1H), 6.60 (d, J=2.6 Hz, 1H), 4.11-3.98 (m, 1H), 3.87 (dd, J=7.6, 3.6 Hz, 1H), 3.65 (dd, J=82.3, 13.0 Hz, 2H), 3.38 (t, J=8.8 Hz, 1H), 3.25-3.02 (m, 1H), 2.48-2.37 (m, 1H), 2.27-2.14 (m, 2H), 2.13-1.97 (m, 1H), 1.84 (dt, J=13.1, 8.4 Hz, 1H), 1.69 (dd, J=13.1, 6.3 Hz, 1H), 1.59-1.49 (m, 1H), 1.45 (s, 3H), 0.79 (t, J=7.2 Hz, 3H). $^{13}$C NMR (125 MHz, CDCl$_3$) δ 180.4, 179.0, 169.8, 140.9, 135.8, 133.9, 133.3, 133.1, 133.1, 132.4, 131.2, 130.3, 129.9, 129.5, 129.3, 128.1, 127.5, 127.5, 125.9, 124.5, 74.5, 70.5, 57.2, 55.0, 41.6, 37.4, 21.0, 18.4, 17.9, 13.9. MS (ESI, m/z): 656.1 [M−H]$^-$.

Example 103 Nickel (II)-(R)—N-(2-benzoyl-4-chlorophenyl)-1-(3,4-dichloro benzyl)-2-methylpyrrolyl-2-carboxamide/(R)-2-amino-3-methylbutanoic acid—Schiff Base Complex According to a synthesis procedure similar to example 91, DL-3-methoxyphenyl alanine was replaced by DL-2-amino-3-methylbutanoic acid and red solids in a yield of 93% were obtained by column chromatography (dichloromethane:methanol=20:1).
mp: 267.5-269.2° C. [α]$^{20}_D$=3016 (c=1, CHCl$_3$).
$^1$H NMR (400 MHz, CDCl$_3$) δ 9.17 (d, J=2.1 Hz, 1H), 8.28 (d, J=9.3 Hz, 1H), 7.65 (dd, J=8.2, 2.1 Hz, 1H), 7.54 (dt, J=16.1, 7.9 Hz, 2H), 7.45 (t, J=6.9 Hz, 1H), 7.31 (dd, J=7.7, 4.2 Hz, 2H), 7.10 (dd, J=9.3, 2.6 Hz, 1H), 6.85 (d, J=7.5 Hz, 1H), 6.61 (d, J=2.6 Hz, 1H), 4.14-3.97 (m, 1H), 3.83-3.72 (m, 2H), 3.53 (d, J=13.1 Hz, 1H), 3.40 (t, J=9.0 Hz, 1H), 3.00 (td, J=12.5, 4.0 Hz, 1H), 2.53-2.34 (m, 1H), 2.27-2.08 (m, 2H), 1.84 (d, J=6.6 Hz, 3H), 1.80-1.67 (m, 1H), 1.45 (s, 3H), 0.73 (d, J=6.8 Hz, 3H).
$^{13}$C NMR (125 MHz, CDCl$_3$) δ 180.4, 177.4, 170.3, 141.0, 135.9, 134.0, 133.2, 133.2, 133.0, 132.5, 132.4, 131.2, 130.2, 129.8, 129.5, 129.1, 127.9, 127.9, 127.5, 125.8, 124.2, 75.6, 74.4, 57.3, 54.9, 41.7, 34.4, 20.5, 19.9, 17.8, 17.7.
MS (ESI, m/z): 656.0 [M−H]$^-$.

Example 104 Nickel (II)-(R)—N-(2-benzoyl-4-chlorophenyl)-1-(3,4-dichloro benzyl)-2-methylpyrrolyl-2-carboxamide/(R)-2-amino-4-methylthiobutanoic acid—Schiff Base Complex According to a synthesis procedure similar to example 91, DL-3-methoxyphenyl alanine was replaced by DL-2-amino-4-methylthiobutanoic acid and red solids in a yield of 90% were obtained by column chromatography (dichloromethane:methanol=20:1).
mp: 123.4-125.8° C. [α]$^{20}_D$=−2202 (c=1, CHCl$_3$).
$^1$H NMR (400 MHz, CDCl$_3$) δ 9.11 (d, J=1.5 Hz, 1H), 8.21 (d, J=9.3 Hz, 1H), 7.72 (d, J=6.7 Hz, 1H), 7.60-7.51 (m, 2H), 7.47 (t, J=7.4 Hz, 1H), 7.32 (dd, J=14.6, 7.6 Hz, 2H), 7.13 (dd, J=9.3, 2.5 Hz, 1H), 6.88 (d, J=7.5 Hz, 1H), 6.60 (d, J=2.5 Hz, 1H), 4.09-3.96 (m, 1H), 3.93 (dd, J=8.3, 3.6 Hz, 1H), 3.66 (dd, J=74.8, 13.0 Hz, 2H), 3.37 (t, J=8.9 Hz, 1H), 3.17 (dd, J=16.5, 10.3 Hz, 1H), 3.09-3.01 (m, 1H), 2.67-2.53 (m, 1H), 2.49-2.37 (m, 1H), 2.19 (dd, J=15.7, 6.7 Hz, 3H), 1.97 (s, 3H), 1.91-1.77 (m, 1H), 1.45 (s, 3H).

$^{13}$C NMR (125 MHz, CDCl$_3$) δ 180.4, 178.3, 170.3, 141.1, 135.7, 133.9, 133.3, 133.2, 132.9, 132.6, 132.4, 131.2, 130.4, 129.9, 129.6, 129.4, 127.9, 127.5, 127.4, 125.9, 124.6, 74.5, 69.8, 57.3, 55.0, 41.6, 35.1, 29.8, 21.3, 18.0, 15.8.

MS (ESI, m/z): 688.0 [M−H]$^-$.

Example 105 Nickel (II)-(R)—N-(2-benzoyl-4-chlorophenyl)-1-(3,4-dichloro benzyl)-2-methylpyrrolyl-2-carboxamide/(R)-2-amino-3-(1H-indol)propionic acid—Schiff Base Complex According to a synthesis procedure similar to example 91, DL-3-methoxyphenylalanine was replaced by DL-2-amino-3-(1H-indol)propionic acid and red solids in a yield of 93% were obtained by column chromatography (dichloromethane:methanol=20:1).

$^1$H NMR (400 MHz, CDCl$_3$) δ 8.90 (d, J=1.9 Hz, 1H), 8.45 (s, 1H), 8.17 (d, J=9.3 Hz, 1H), 7.60-7.55 (m, 2H), 7.52 (t, J=7.5 Hz, 1H), 7.44 (d, J=8.2 Hz, 1H), 7.40-7.26 (m, 4H), 7.19 (t, J=7.7 Hz, 1H), 7.11 (dd, J=9.3, 2.6 Hz, 1H), 7.03 (d, J=2.0 Hz, 1H), 6.96 (t, J=7.5 Hz, 1H), 6.85 (d, J=7.7 Hz, 1H), 6.63 (d, J=2.6 Hz, 1H), 4.31 (t, J=4.7 Hz, 1H), 4.08 (d, J=12.4 Hz, 1H), 3.32 (dd, J=14.7, 4.5 Hz, 1H), 3.01 (ddd, J=19.7, 11.9, 6.0 Hz, 3H), 2.88-2.82 (m, 1H), 2.13 (tt, J=13.5, 8.1 Hz, 1H), 1.65 (s, 3H), 1.88-1.70 (m, 2H), 1.51-1.42 (m, 1H).

MS (ESI, m/z): 741.1 [M−H]$^-$.

Example 106 Nickel (II)-(R)—N-(2-benzoyl-4-chlorophenyl)-1-(3,4-dichloro benzyl)-2-methylpyrrolyl-2-carboxamide/(R)-2-amino-5-methyl-4-hexenoic acid—Schiff Base Complex According to a synthesis procedure similar to example 91, DL-3-methoxyphenylalanine was replaced by DL-2-amino-5-methyl-4-hexenoic acid and red solids in a yield of 90% were obtained by column chromatography (dichloromethane:methanol=20:1).

$^1$H NMR (400 MHz, CDCl$_3$) δ 8.90 (d, J=2.0 Hz, 1H), 8.11 (d, J=9.3 Hz, 1H), 7.74 (dd, J=8.2, 2.0 Hz, 1H), 7.58-7.50 (m, 2H), 7.46 (ddd, J=7.3, 4.5, 1.8 Hz, 1H), 7.34 (d, J=8.1 Hz, 1H), 7.30-7.27 (m, 1H), 7.10 (dd, J=9.3, 2.6 Hz, 1H), 6.89 (d, J=7.5 Hz, 1H), 6.57 (d, J=2.5 Hz, 1H), 5.66 (t, J=7.6 Hz, 1H), 4.30 (d, J=12.6 Hz, 1H), 4.01 (dd, J=6.4, 4.6 Hz, 1H), 3.67-3.45 (m, 2H), 3.35 (dd, J=10.9, 6.2 Hz, 1H), 3.20 (d, J=12.6 Hz, 1H), 2.78-2.52 (m, 3H), 2.43-2.32 (m, 1H), 2.05 (td, J=10.7, 6.3 Hz, 1H), 1.86 (s, 3H), 1.70 (s, 3H), 1.54 (s, 3H).

MS (ESI, m/z): 680.09 [M−H]$^-$.

Example 107 Nickel (II)-(R)—N-(2-benzoyl-4-chlorophenyl)-1-(3,4-dichloro benzyl)-2-methylpyrrolyl-2-carboxamide/(R)-2-aminoglutaric acid—Schiff Base Complex According to a synthesis procedure similar to example 91, DL-3-methoxyphenylalanine was replaced by DL-2-aminoglutaric acid and red solids in a yield of 89% were obtained by column chromatography (dichloromethane:methanol=20:1).

$^1$H NMR (400 MHz, CDCl$_3$) δ 8.90 (s, 1H), 8.02 (d, J=9.2 Hz, 1H), 7.74 (d, J=7.8 Hz, 1H), 7.57-7.50 (m, 2H), 7.47 (t, J=6.9 Hz, 1H), 7.32 (d, J=8.1 Hz, 1H), 7.26-7.23 (m, 1H), 7.11-7.01 (m, 2H), 6.57 (d, J=2.3 Hz, 1H), 4.27 (d, J=12.4 Hz, 1H), 3.93 (dd, J=8.0, 3.4 Hz, 1H), 3.61 (dd, J=19.2, 9.7 Hz, 1H), 3.55-3.48 (m, 1H), 3.40 (dd, J=11.1, 5.4 Hz, 1H), 3.20 (d, J=12.4 Hz, 1H), 3.06 (dt, J=17.1, 6.9 Hz, 1H), 2.71-2.62 (m, 1H), 2.56-2.44 (m, 2H), 2.35 (dq, J=15.7, 7.8 Hz, 1H), 2.22-2.13 (m, 1H), 2.05 (td, J=10.8, 6.0 Hz, 1H), 1.90 (s, 3H).

MS (ESI, m/z): 684.09 [M−H]$^-$.

Example 108 Nickel (II)-(R)—N-(2-benzoyl-4-chlorophenyl)-1-(3,4-dichloro benzyl)-2-methylpyrrolyl-2-carboxamide/(R)-2,5-diamino-5-pentanone acid—Schiff Base Complex According to a synthesis procedure similar to example 91, DL-3-methoxyphenylalanine was replaced by DL-2,5-diamino-5-pentanone acid and red solids in a yield of 88% were obtained by column chromatography (dichloromethane:methanol=20:1).

$^1$H NMR (400 MHz, CDCl$_3$) δ 8.88 (d, J=0.9 Hz, 1H), 8.05 (d, J=9.2 Hz, 1H), 7.75 (dd, J=8.1, 1.2 Hz, 1H), 7.58-7.49 (m, 3H), 7.37 (d, J=8.2 Hz, 1H), 7.22 (s, 1H), 7.12 (dd, J=9.2, 2.3 Hz, 1H), 6.94 (d, J=7.0 Hz, 1H), 6.59 (d, J=2.4 Hz, 1H), 6.00 (s, 1H), 5.21 (s, 1H), 4.30 (d, J=12.6 Hz, 1H), 3.82 (dd, J=10.9, 4.3 Hz, 1H), 3.74-3.59 (m, 1H), 3.52 (dd, J=10.5, 5.6 Hz, 1H), 3.38 (dd, J=11.4, 5.4 Hz, 1H), 3.22 (d, J=12.4 Hz, 1H), 2.76-2.54 (m, 3H), 2.50-2.42 (m, 1H), 2.31-2.20 (m, 2H), 2.08 (td, J=10.9, 5.6 Hz, 1H), 1.98 (s, 3H).

MS (ESI, m/z): 683.06 [M−H]$^-$.

Example 109 Nickel (II)-(R)—N-(2-benzoyl-4-chlorophenyl)-1-(3,4-dichloro benzyl)-2-methylpyrrolyl-2-carboxamide/(R)-homocysteine—Schiff Base Complex According to a synthesis procedure similar to example 91, DL-3-methoxyphenylalanine was replaced by DL-homocysteine and red solids in a yield of 93% were obtained by column chromatography (dichloromethane:methanol=20:1).

$^1$H NMR (400 MHz, CDCl$_3$) δ 8.88 (d, J=1.2 Hz, 1H), 8.05 (d, J=9.3 Hz, 1H), 7.75 (dd, J=8.0, 1.0 Hz, 1H), 7.50 (ddt, J=29.3, 14.8, 7.3 Hz, 3H), 7.36 (d, J=8.1 Hz, 1H), 7.24 (s, 1H), 7.11 (dd, J=9.3, 2.4 Hz, 1H), 6.89 (d, J=7.4 Hz, 1H), 6.57 (d, J=2.4 Hz, 1H), 4.30 (d, J=12.5 Hz, 1H), 3.87 (dd, J=8.2, 3.4 Hz, 1H), 3.68-3.56 (m, 1H), 3.55-3.49 (m, 1H), 3.37 (dd, J=10.9, 5.8 Hz, 1H), 3.21 (d, J=12.6 Hz, 1H), 2.95 (dd, J=17.5, 9.3 Hz, 1H), 2.75-2.64 (m, 1H), 2.63-2.45 (m, 3H), 2.29-2.19 (m, 1H), 2.10 (s, 3H), 1.96 (dd, J=24.2, 10.7 Hz, 1H).

MS (ESI, m/z): 672.03 [M−H]$^-$.

Example 110 Nickel (II)-(R)—N-(2-benzoyl-4-chlorophenyl)-1-ethyl-2-methylpyrrolyl-2-carboxamide/(S)-3-amino-2-benzylpropionic acid—Schiff Base Complex According to a synthesis procedure similar to example 65, brown solids (yield 68%) were obtained.

mp 128-130° C. [α]$^{20}_D$=+2426.5 (c=0.034, CHCl$_3$).

$^1$H NMR (400 MHz, Methanol-d$_4$) δ 8.91 (d, J=2.1 Hz, 1H), 8.32 (dd, J=8.3, 2.1 Hz, 1H), 7.74 (d, J=9.2 Hz, 1H), 7.48 (d, J=8.2 Hz, 1H), 7.39-7.25 (m, 2H), 7.23-7.12 (m, 4H), 7.06 (dd, J=9.2, 2.6 Hz, 1H), 7.03-6.95 (m, 3H), 6.64 (dt, J=7.6, 1.6 Hz, 1H), 6.42 (d, J=2.6 Hz, 1H), 3.98-3.83 (m, 2H), 3.77 (d, J=13.3 Hz, 1H), 3.58-3.48 (m, 1H), 3.40 (d, J=13.3 Hz, 1H), 3.27-3.18 (m, 1H), 3.14-3.02 (m, 2H), 2.68-2.62 (m, 1H), 2.51-2.10 (m, 4H), 1.43 (s, 3H).

$^{13}$C NMR (125 MHz, Methanol-d$_4$) δ 182.5, 180.4, 173.1, 141.3, 139.8, 138.2, 134.9, 134.6, 133.9, 133.5, 133.1, 132.7, 132.4, 132.2, 131.2, 131.0, 130.3, 130.2, 129.9, 129.6, 128.1, 127.7, 127.6, 126.8, 125.9, 74.9, 56.7, 56.3, 55.3, 49.3, 42.8, 37.2, 22.2, 18.6.
LRMS (ESI+APCI) m/z: 718.0, HRMS (ESI) m/z: found: 718.0940, calcd 718.0935 for $C_{35}H_{32}Cl_3N_3NiO_3^+$ [M+H]$^+$.

Example 111 Nickel (II)-(R)—N-(2-benzoyl-4-chlorophenyl)-1-ethyl-2-methylpyrrolyl-2-carboxamide/(S)-3-amino-2-(4-fluorobenzyl)propionic acid—Schiff Base Complex According to a synthesis procedure similar to example 65, brown solids (yield 58%) were obtained.
mp 123-124° C. $[\alpha]^{20}_D$=−3310.5 (c=0.038, CHCl$_3$).
$^1$H NMR (400 MHz, Methanol-d$_4$) δ 8.15 (d, J=9.1 Hz, 1H), 7.41-7.33 (m, 2H), 7.26 (dd, J=9.1, 2.6 Hz, 1H), 7.21-7.13 (m, 1H), 7.03-6.94 (m, 3H), 6.90-6.82 (m, 2H), 6.78 (dt, J=6.6, 1.9 Hz, 1H), 6.53 (d, J=2.6 Hz, 1H), 3.96 (t, J=12.3 Hz, 1H), 3.86-3.73 (m, 2H), 3.22-3.06 (m, 3H), 2.62-2.29 (m, 6H), 1.94-1.86 (m, 4H), 1.24 (s, 3H). $^{13}$C NMR (125 MHz, Methanol-d$_4$) δ 183.7, 180.3, 173.0, 163.9, 162.0, 141.9, 136.1, 136.1, 135.1, 133.4, 133.0, 131.7, 131.6, 131.6, 130.9, 130.2, 130.2, 128.1, 127.8, 126.9, 126.6, 116.3, 116.1, 75.0, 56.9, 54.5, 49.7, 49.1, 41.9, 36.3, 23.4, 18.1, 15.5. LRMS (ESI+APCI) m/z: 606.1, HRMS (ESI) m/z: found: 606.1476, calcd 606.1464 for $C_{31}H_{31}ClFN_3NiO_3^+$ [M+H]$^+$.

Example 112 Nickel (II)-(R)—N-(2-benzoyl-4-chlorophenyl)-1-ethyl-2-methylpyrrolyl-2-carboxamide/(S)-3-amino-2-(4-methoxybenzyl)propionic acid—Schiff Base Complex According to a synthesis procedure similar to example 65, brown solids (yield 62%) were obtained.
mp 127-130° C. $[\alpha]^{20}_D$=−3618.8 (c=0.032, CHCl$_3$). $^1$H NMR (400 MHz, Methanol-d$_4$) δ 8.14 (d, J=9.1 Hz, 1H), 7.41-7.32 (m, 2H), 7.26 (d, J=9.1 Hz, 1H), 7.15 (t, J=8.5 Hz, 1H), 6.99 (d, J=7.6 Hz, 1H), 6.91-6.84 (m, 2H), 6.77 (d, J=7.6 Hz, 1H), 6.72-6.66 (m, 2H), 6.53 (d, J=2.6 Hz, 1H), 3.94 (t, J=12.4 Hz, 1H), 3.79 (s, 3H), 3.78-3.71 (m, 1H), 3.20-3.02 (m, 3H), 2.64-2.49 (m, 2H), 2.45-2.26 (m, 4H), 1.91 (t, J=7.4 Hz, 3H), 1.24 (s, 3H).
$^{13}$C NMR (125 MHz, Methanol-d$_4$) δ 183.69, 180.68, 173.00, 159.80, 141.96, 135.13, 133.45, 133.01, 131.93, 131.70, 130.97, 130.94, 130.24, 130.17, 128.13, 127.91, 126.92, 126.55, 115.03, 75.01, 57.02, 55.68, 54.58, 49.69, 49.30, 41.97, 36.33, 23.41, 18.08, 15.50.
LRMS (ESI+APCI) m/z: 618.1, HRMS (ESI) m/z: found: 618.1667, calcd 618.1664 for $C_{32}H_{34}ClN_3NiO_3^+$ [M+H]$^+$.

Example 113 Nickel (II)-(R)—N-(2-benzoyl-4-chlorophenyl)-1-ethyl-2-methylpyrrolyl-2-carboxamide/(S)-3-amino-2-methylpropionic acid—Schiff Base Complex According to a synthesis procedure similar to example 65, brown solids (yield 76%) were obtained.
mp 257-259° C. $[\alpha]^{20}_D$=−4854.5 (c=0.044, CHCl$_3$).
$^1$H NMR (400 MHz, Methanol-d$_4$) δ 8.17 (d, J=9.1 Hz, 1H), 7.66-7.49 (m, 3H), 7.45-7.35 (m, 1H), 7.29 (dd, J=9.1, 2.5 Hz, 1H), 6.99 (d, J=7.6 Hz, 1H), 6.65 (d, J=2.6 Hz, 1H), 4.26-3.53 (m, 3H), 3.29-3.18 (m, 3H), 3.12-2.90 (m, 1H), 2.64-2.18 (m, 5H), 2.06-1.76 (m, 4H), 1.26 (s, 3H), 0.98 (d, J=7.3 Hz, 3H).

$^{13}$C NMR (125 MHz, Methanol-d$_4$) δ 183.7, 182.0, 172.7, 142.0, 135.8, 133.6, 133.1, 131.5, 130.6, 130.1, 128.7, 128.3, 126.9, 126.6, 75.1, 59.8, 54.4, 49.8, 42.1, 41.9, 23.4, 18.1, 15.5, 15.2.
LRMS (ESI+APCI) m/z: 512.0, HRMS (ESI) m/z: found: 512.1256, calcd 512.1245 for $C_{25}H_{28}ClN_3NiO_3^+$ [M+H]$^+$.

Example 114 Nickel (II)-(R)—N-(2-benzoyl-4-chlorophenyl)-1-ethyl-2-methylpyrrolyl-2-carboxamide/(S)-2-(aminomethyl)-4-methylpentanoic acid—Schiff Base Complex According to a synthesis procedure similar to example 65, brown solids (yield 62%) were obtained.
mp 120-122° C. $[\alpha]^{20}_D$=−4383.3 (c=0.048, CHCl$_3$).
$^1$H NMR (400 MHz, Methanol-d$_4$) δ 8.19 (d, J=9.1 Hz, 1H), 7.60-7.52 (m, 3H), 7.44-7.42 (m, 1H), 7.29 (dd, J=9.1, 2.6 Hz, 1H), 6.99 (dd, J=7.7, 1.7 Hz, 1H), 6.67 (d, J=2.6 Hz, 1H), 3.95-3.73 (m, 3H), 3.25-3.14 (m, 2H), 2.62-2.53 (m, 1H), 2.41-2.32 (m, 3H), 2.24-2.17 (m, 1H), 1.94-1.86 (m, 4H), 1.74-1.67 (m, 1H), 1.26 (s, 3H), 1.25-1.05 (m, 2H), 0.78 (dd, J=6.5, 3.8 Hz, 6H).
$^{13}$C NMR (125 MHz, Methanol-d$_4$) δ 183.6, 181.9, 172.9, 142.0, 135.9, 133.5, 133.1, 131.4, 131.3, 130.7, 130.2, 128.5, 128.4, 126.9, 126.6, 75.1, 58.0, 54.3, 49.8, 45.2, 41.9, 40.8, 26.8, 23.6, 23.4, 22.2, 18.1, 15.5.
LRMS (ESI+APCI) m/z: 554.2, HRMS (ESI) m/z: found: 554.1727, calcd 554.1719 for $C_{28}H_{34}ClN_3NiO_3^+$ [M+H]$^+$.

Example 115 Nickel (II)-(R)—N-(2-benzoyl-4-chlorophenyl)-1-ethyl-2-methylpyrrolyl-2-carboxamide/(S)-3-amino-2-cyclohexylpropionic acid—Schiff Base Complex According to a synthesis procedure similar to example 65, brown solids (yield 87%) were obtained.
mp 145-147° C. $[\alpha]^{20}_D$=−3161.8 (c=0.034, CHCl$_3$).
$^1$H NMR (400 MHz, Methanol-d$_4$) δ 8.18 (d, J=9.1 Hz, 1H), 7.66-7.51 (m, 3H), 7.42-7.37 (m, 1H), 7.28 (dd, J=9.1, 2.6 Hz, 1H), 6.98 (d, J=7.6 Hz, 1H), 6.65 (d, J=2.6 Hz, 1H), 4.02-3.69 (m, 2H), 3.26-3.03 (m, 2H), 2.65-2.50 (m, 1H), 2.41-2.32 (m, 2H), 2.27-2.19 (m, 1H), 2.14-2.05 (m, 1H), 1.96-1.54 (m, 8H), 1.46-0.54 (m, 11H).
$^{13}$C NMR (125 MHz, Methanol-d$_4$) δ 183.6, 180.9, 173.0, 142.0, 135.7, 133.5, 133.0, 131.5, 131.4, 130.6, 130.2, 128.6, 128.4, 126.9, 126.6, 75.1, 54.8, 54.3, 52.9, 49.9, 41.9, 40.2, 32.5, 29.3, 27.8, 27.6, 27.2, 23.3, 18.0, 15.5.
LRMS (ESI+APCI) n/z: 580.2, HRMS (ESI) m/z: found: 580.1881, calcd 580.1871 for $C_{30}H_{36}ClN_3NiO_3^+$ [M+H]$^+$.

Example 116 Nickel (II)-(R)—N-(2-benzoyl-4-chlorophenyl)-1-ethyl-2-methylpyrrolyl-2-carboxamide/(S)-3-amino-2-phenylpropionic acid—Schiff Base Complex According to a synthesis procedure similar to example 65, brown solids (yield 55%, dr 55/45) were obtained.
mp 150-151° C. $[\alpha]^{20}_D$=−3648.0 (c=0.05, CHCl$_3$).
$^1$H NMR (400 MHz, Methanol-d$_4$) δ 8.20 (d, J=9.1 Hz, 1H), 7.66-7.52 (m, 3H), 7.46 (t, J=7.6 Hz, 1H), 7.31 (dd, J=9.1, 2.6 Hz, 1H), 7.28-7.16 (m, 3H), 7.10-7.03 (m, 2H), 6.91 (d, J=7.7 Hz, 1H), 6.69 (d, J=2.6 Hz, 1H), 4.34 (t, J=13.0 Hz, 1H), 3.89-3.86 (m, 2H), 3.53 (dd, J=11.8, 3.5 Hz, 1H), 3.29-3.97 (m, 1H), 3.15 (dd, J=13.0, 3.6 Hz, 1H), 2.65-2.56 (m, 1H), 2.46-2.29 (m, 3H), 1.99-1.90 (m, 4H), 1.27 (s, 3H).

¹³C NMR (125 MHz, Methanol-d₄) δ 183.7, 180.1, 173.3, 142.2, 139.1, 135.8, 133.7, 133.2, 131.6, 131.4, 130.6, 130.1, 129.8, 129.1, 128.5, 128.4, 128.4, 126.9, 126.7, 75.2, 60.1, 54.5, 54.3, 49.9, 41.9, 23.5, 18.1, 15.5.

LRMS (ESI+APCI) m/z: 574.1, HRMS (ESI) m/z: found: 574.1410, calcd 574.1402 for $C_{30}H_{30}ClN_3NiO_3^+$ [M+H]⁺.

Example 117 Nickel (II)-(R)—N-(2-benzoyl-4-chlorophenyl)-1-ethyl-2-methylpyrrolyl-2-carboxamide/(S)-3-amino-2-(4-chlorophenyl)propionic acid—Schiff Base Complex According to a synthesis procedure similar to example 65, brown solids (yield 59%, dr 59/41) were obtained.

mp=130-132° C. $[\alpha]^{20}_D$=−3312.5 (c=0.048, CHCl₃).

¹H NMR (400 MHz, Methanol-d₄) δ 8.20 (d, J=9.1 Hz, 1H), 7.65-7.44 (m, 4H), 7.31 (dd, J=9.1, 2.6 Hz, 1H), 7.28-7.23 (m, 2H), 7.08-7.01 (m, 2H), 6.93 (d, J=7.7 Hz, 1H), 6.69 (d, J=2.6 Hz, 1H), 4.35 (t, J=12.5 Hz, 1H), 3.97-3.81 (m, 2H), 3.54 (dd, J=12.0, 3.4 Hz, 1H), 3.29-3.27 (m, 1H), 3.12 (dd, J=12.9, 3.5 Hz, 1H), 2.63-2.50 (m, 1H), 2.46-2.31 (m, 3H), 1.98-1.90 (m, 4H), 1.27 (s, 3H).

¹³C NMR (125 MHz, Methanol-d₄) δ 183.7, 179.6, 173.4, 142.2, 137.8, 135.7, 134.2, 133.7, 133.3, 131.6, 131.4, 130.8, 130.7, 130.1, 129.8, 128.6, 128.4, 127.0, 126.7, 75.2, 59.8, 54.4, 49.5, 41.9, 23.5, 18.1, 15.5.

LRMS (ESI+APCI) m/z: 608.0, HRMS (ESI) m/z: found: 608.1026, calcd 608.1012 for $C_{30}H_{29}Cl_2N_3NiO_3^+$ [M+H]⁺.

Example 118 Nickel (II)-(R)—N-(2-benzoyl-4-chlorophenyl)-1-ethyl-2-methylpyrrolyl-2-carboxamide/(S)-3-amino-2-(4-methoxyphenyl)propionic acid—Schiff Base Complex According to a synthesis procedure similar to example 65, brown solids (yield 65%, dr 50/50) were obtained.

mp=146-148° C. $[\alpha]^{20}_D$=−3052.4 (c=0.042, CHCl₃).

¹H NMR (400 MHz, Methanol-d₄) δ 8.19 (d, J=9.1 Hz, 1H), 7.68-7.52 (m, 3H), 7.48 (t, J=7.5 Hz, 1H), 7.31 (dd, J=9.1, 2.6 Hz, 1H), 7.01-6.95 (m, 2H), 6.93 (d, J=7.7 Hz, 1H), 6.84-6.77 (m, 2H), 6.69 (d, J=2.6 Hz, 1H), 4.29 (t, J=12.9 Hz, 1H), 3.91-3.78 (m, 2H), 3.73 (s, 3H), 3.48 (dd, J=11.7, 3.6 Hz, 1H), 3.29-3.23 (m, 1H), 3.12 (dd, J=13.0, 3.6 Hz, 1H), 2.64-2.56 (m, 1H), 2.44-2.34 (m, 3H), 1.95 (q, J=10.3, 8.7 Hz, 4H), 1.27 (s, 3H).

¹³C NMR (125 MHz, Methanol-d₄) δ 183.7, 180.6, 173.3, 160.4, 142.2, 135.8, 133.7, 133.2, 131.6, 131.4, 131.0, 130.6, 130.1, 128.5, 128.5, 126.9, 126.6, 115.2, 75.2, 60.2, 55.7, 54.4, 53.5, 49.9, 41.9, 23.5, 18.1, 15.5.

LRMS (ESI+APCI) m/z: 604.1, HRMS (ESI) m/z: found: 604.1503, calcd 604.1508 for $C_{31}H_{32}ClN_3NiO_3^+$ [M+H]⁺

Example 119 Nickel (II)-(R)—N-(2-benzoyl-4-chlorophenyl)-1-ethyl-2-methylpyrrolyl-2-carboxamide/(S)-3-amino-2-(naphth-1-yl)propionic acid—Schiff Base Complex According to a synthesis procedure similar to example 65, brown solids (yield 63%, dr 50/50) were obtained.

mp=146-147° C. $[\alpha]^{20}_D$=−3440.0 (c=0.046, CHCl₃).

¹H NMR (400 MHz, Methanol-d₄) δ 8.21 (d, J=9.1 Hz, 1H), 7.80-7.72 (m, 3H), 7.65 (d, J=4.6 Hz, 2H), 7.58-7.37 (m, 5H), 7.32 (dd, J=9.1, 2.6 Hz, 1H), 7.18 (dd, J=8.5, 1.8 Hz, 1H), 6.89 (dd, J=7.8, 1.4 Hz, 1H), 6.70 (d, J=2.6 Hz, 1H), 4.45 (t, J=12.9, 11.8 Hz, 1H), 3.92-3.79 (m, 2H), 3.71 (dd, J=11.7, 3.5 Hz, 1H), 3.38-3.32 (m, 1H), 3.22 (dd, J=13.0, 3.5 Hz, 1H), 2.69-2.53 (m, 1H), 2.48-2.27 (m, 3H), 2.02-1.87 (m, 4H), 1.26 (s, 3H).

¹³C NMR (125 MHz, Methanol-d₄) δ 183.7, 180.1, 173.4, 142.2, 136.4, 135.8, 134.9, 134.0, 133.7, 133.3, 131.6, 131.4, 130.6, 130.1, 129.5, 128.7, 128.6, 128.5, 128.5, 128.2, 127.3, 127.0, 127.0, 126.9, 126.7, 75.2, 60.0, 54.4, 54.4, 49.9, 41.9, 23.5, 18.1, 15.5.

LRMS (ESI+APCI) m/z: 624.1, HRMS (ESI) m/z: found: 624.1566, calcd 624.1558 for $C_{34}H_{32}ClN_3NiO_3^+$ [M+H]⁺.

Example 120 Nickel (II)-(R)—N-(2-benzoyl-4-chlorophenyl)-1-ethyl-2-methylpyrrolyl-2-carboxamide/(S)-3-amino-2-(4-methylbenzyl)propionic acid—Schiff Base Complex According to a synthesis procedure similar to example 65, brown solids (yield 70%, dr 84/16) were obtained.

mp 124-126° C. $[\alpha]^{20}_D$=−3277.3 (c=0.034, CHCl₃).

¹H NMR (400 MHz, Methanol-d₄) δ 8.13 (d, J=9.1 Hz, 1H), 7.40-7.32 (m, 2H), 7.28-7.21 (m, 1H), 7.15-7.09 (m, 1H), 6.99-6.93 (m, 3H), 6.85 (d, J=8.0 Hz, 2H), 6.77 (d, J=7.2 Hz, 1H), 6.53 (d, J=2.6 Hz, 1H), 3.93 (t, J=12.4 Hz, 1H), 3.84-3.68 (m, 2H), 3.20-3.06 (m, 3H), 2.62-2.53 (m, 2H), 2.44-2.39 (m, 1H), 2.39-2.34 (m, 1H), 2.32 (s, 3H), 2.31-2.22 (m, 2H), 1.92-1.87 (m, 4H), 1.24 (s, 3H).

¹³C NMR (125 MHz, Methanol-d₄) δ 183.7, 180.6, 173.0, 142.0, 137.1, 136.9, 135.1, 133.5, 133.0, 131.7, 130.8, 130.3, 130.1, 129.9, 128.1, 127.9, 126.9, 126.6, 75.0, 57.0, 54.7, 49.69, 42.0, 36.8, 23.4, 21.1, 18.1, 15.5.

LRMS (ESI+APCI) m/z: 601.8, HRMS (ESI) m/z: found: 602.1705, calcd 602.1715 for $C_{32}H_{35}ClN_3NiO_3^+$ [M+H]⁺.

Example 121 Nickel (II)-(R)—N-(2-benzoyl-4-chlorophenyl)-1-ethyl-2-methylpyrrolyl-2-carboxamide/(S)-3-amino-2-(4-trifluoromethylbenzyl)propionic acid—Schiff Base Complex According to a synthesis procedure similar to example 65, brown solids (yield 72%, dr 89/11) were obtained.

mp 137-139° C. $[\alpha]^{20}_D$=−3950.5 (c=0.046, CHCl₃).

¹H NMR (400 MHz, Methanol-d₄) δ 8.14 (d, J=9.1 Hz, 1H), 7.45 (d, J=8.0 Hz, 2H), 7.35-7.25 (m, 3H), 7.17 (d, J=8.1 Hz, 2H), 7.05-6.95 (m, 2H), 6.78 (d, J=7.6 Hz, 1H), 6.52 (d, J=2.5 Hz, 1H), 4.00 (t, J=12.3 Hz, 1H), 3.88-3.78 (m, 2H), 3.30-3.26 (m, 1H), 3.21 (dd, J=11.1, 7.4 Hz, 1H), 3.07 (dd, J=12.7, 3.4 Hz, 1H), 2.61-2.44 (m, 3H), 2.39-2.30 (m, 3H), 1.94-1.87 (m, 4H), 1.25 (s, 3H).

¹³C NMR (125 MHz, Methanol-d₄) δ 183.7, 179.9, 173.1, 145.1, 142.0, 135.1, 133.4, 133.1, 131.4, 131.0, 130.6, 130.1, 130.0, 129.8, 129.5, 128.0, 127.7, 126.9, 126.6, 126.5, 126.5, 75.0, 56.8, 54.5, 49.7, 42.0, 36.9, 23.4, 18.1, 15.5.

LRMS (ESI+APCI) m/z: 655.8, HRMS (ESI) m/z: found: 656.1431, calcd 656.1432 for $C_{32}H_{32}CF_3N_3NiO_3^+$ [M+H]⁺.

Example 122 Nickel (II)-(R)—N-(2-benzoyl-4-chlorophenyl)-1-ethyl-2-methylpyrrolyl-2-carboxamide/(S)-3-amino-2-tert-butyl propionic acid—Schiff Base Complex mp=136-137° C. $[\alpha]^{20}_D$=−3670.0 (c=0.048, CHCl₃).

¹H NMR (400 MHz, Methanol-d₄) δ 8.21 (d, J=9.1 Hz, 1H), 7.63-7.58 (m, 2H), 7.56-7.52 (m, 1H), 7.42-7.37 (m, 1H), 7.29 (dd, J=9.1, 2.6 Hz, 1H), 6.99 (d, J=7.6 Hz, 1H), 6.67 (d, J=2.6 Hz, 1H), 4.27 (t, J=12.5 Hz, 1H), 4.07-3.97 (m, 1H), 3.93-3.84 (m, 1H), 3.33 (d, J=4.7 Hz, 1H), 3.13 (dd, J=10.9, 7.8 Hz, 1H), 2.66 (dq, J=15.0, 7.5 Hz, 1H), 2.44-

2.34 (m, 2H), 2.28 (dq, J=14.1, 7.1 Hz, 1H), 2.07 (dd, J=12.5, 4.7 Hz, 1H), 2.03-1.95 (m, 1H), 1.89 (t, J=7.3 Hz, 3H), 1.24 (s, 3H), 0.84 (s, 9H).

$^{13}$C NMR (125 MHz, Methanol-$d_4$) δ 183.8, 181.5, 173.1, 142.3, 135.6, 133.5, 133.2, 131.7, 131.7, 130.6, 130.1, 128.8, 128.6, 126.9, 126.5, 74.9, 57.8, 56.4, 55.0, 49.5, 42.2, 33.9, 28.5, 23.7, 18.1, 15.5.

LRMS (ESI+APCI) m/z: 655.8, HRMS (ESI) m/z: found: 554.1704, calcd 554.1715 for $C_{28}H_{35}ClN_3NiO_3^+$ [M+H]$^+$.

Example 123 Nickel (II)-(R)—N-(2-benzoyl-4-chlorophenyl)-1-ethyl-2-methylpyrrolyl-2-carboxamide/ (S)-3-amino-2-isopropylpropionic acid—Schiff Base Complex mp 130-132° C. $[α]^{20}_D$=−3241.0 (c=0.034, CHCl$_3$).

$^1$H NMR (400 MHz, Methanol-$d_4$) δ 8.18 (d, J=9.1 Hz, 1H), 7.61-7.53 (m, 3H), 7.46-7.39 (m, 1H), 7.29 (dd, J=9.1, 2.6 Hz, 1H), 7.00 (d, J=7.5 Hz, 1H), 6.66 (d, J=2.6 Hz, 1H), 4.03-3.87 (m, 2H), 3.85-3.74 (m, 1H), 3.24-3.16 (m, 2H), 2.60-2.46 (m, 2H), 2.41-2.32 (m, 3H), 2.14-2.08 (m, 1H), 1.95-1.87 (m, 4H), 1.26 (s, 3H), 0.72 (d, J=6.9 Hz, 3H), 0.65 (d, J=7.1 Hz, 3H).

$^{13}$C NMR (125 MHz, Methanol-$d_4$) δ 183.6, 181.0, 173.1, 142.1, 135.7, 133.4, 133.1, 131.5, 130.6, 130.2, 128.6, 128.5, 126.9, 126.6, 75.1, 54.3, 54.0, 53.1, 49.8, 42.0, 29.7, 23.4, 20.9, 18.1, 17.9, 15.5.

LRMS (ESI+APCI) m/z: 539.9, HRMS (ESI) m/z: found: 540.1543, calcd 540.1558 for $C_{27}H_{33}ClN_3NiO_3^+$ [M+H]$^+$.

Example 124

The chelates prepared in examples 72-89 were hydrolyzed in substantially same manner as in example 66 to give: (S)-3-amino-3-(2-fluoro)phenylpropionic acid, (S)-3-amino-3-(4-chloro)phenylpropionic acid, (S)-3-amino-3-(3,4-dimethoxy)phenylpropionic acid, (S)-3-amino-3-(4-isopropyl)phenylpropionic acid, (S)-3-amino-3-(4-methoxy)phenylpropionic acid, (S)-3-amino-3-(3-methoxy)phenylpropionic acid, (S)-3-amino-3-(3-trifluoromethyl)phenylpropionic acid, (S)-3-amino-3-(3-pyridyl)propionic acid, (S)-3-amino-3-(2-thienyl)propionic acid, (S)-3-amino-3-(1-naphthyl)propionic acid, (S)-3-aminobutanoic acid, (S)-3-aminopentanoic acid, (S)-3-aminoheptanoic acid, (S)-3-amino-5-methylhexanoic acid, (S)-3-amino-4-methylpentanoic acid, (S)-3-amino-3-cyclopropylpropionic acid, (S)-3-amino-3-cyclohexylpropionic acid and (S)-3-amino-4-(2,4,5-trifluorophenyl)butanoic acid, respectively.

All documents mentioned in the present invention are hereby incorporated by reference, just as each document is cited separately as a reference. In addition, it should be understood that various modifications and changes may be made by those skilled in the art after reading the above teachings of the present invention and these equivalent forms also fall within the scope defined by the claims appended hereto.

The invention claimed is:

1. A novel resolution method for an alpha amino acid, an alpha substituted beta amino acid and a beta substituted beta amino acid comprising the step of hydrolyzing a compound of formula VI to obtain the alpha amino acid, the alpha substituted beta amino acid and the beta substituted beta amino acid of formula VII,

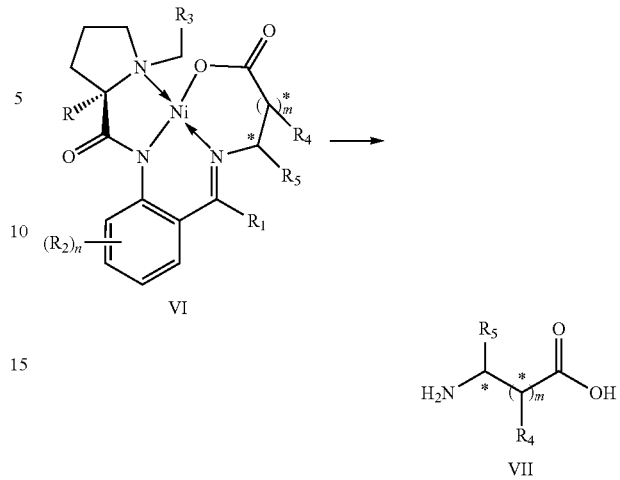

wherein n is an integer from 1 to 4, m is an integer from 0 to 1;

R is selected from the group consisting of C1-C4 alkyl, C1-C4 haloalkyl and unsubstituted or substituted phenyl, wherein the substituted phenyl means that the phenyl has 1-5 substituents, and each substituent is independently selected from the group consisting of amino, halogen, hydroxyl, C1-C4 alkyl and C1-C4 haloalkyl;

R$_1$ is selected from the group consisting of H, C1-C4 alkyl, C1-C4 haloalkyl and unsubstituted or substituted phenyl, wherein the substituted phenyl means that the phenyl has 1-5 substituents, and each substituent is independently selected from the group consisting of amino, halogen, hydroxyl, C1-C4 alkyl and C1-C4 haloalkyl;

R$_2$ is selected from the group consisting of H, halogen, amino, hydroxyl, C1-C4 alkyl and C1-C4 haloalkyl;

R$_3$ is selected from the group consisting of H, C1-C4 alkyl, C1-C4 haloalkyl, unsubstituted or substituted phenyl and —(C1-C4 alkylene)-(unsubstituted or substituted phenyl); wherein the substituted phenyl means that the phenyl has 1-5 substituents, and each substituent is independently selected from the group consisting of amino, halogen, hydroxyl, C1-C4 alkyl and C1-C4 haloalkyl;

R$_4$ is selected from the group consisting of H, unsubstituted or substituted C6-C10 aryl, unsubstituted or substituted C3-C6 heteroaryl and unsubstituted or substituted C3-C6 cycloalkyl, wherein the "substituted" means that there are 1-5 substituents, and each substituent is independently selected from the group consisting of amino, halogen, hydroxyl, nitro, cyano, C1-C4 alkyl, C1-C4 alkoxy and C1-C4 haloalkyl;

R$_5$ is selected from the group consisting of H, unsubstituted or substituted C6-C10 aryl, unsubstituted or substituted C3-C6 heteroaryl and unsubstituted or substituted C3-C6 cycloalkyl, wherein the "substituted" means that there are 1-5 substituents, and each substituent is independently selected from the group consisting of amino, halogen, hydroxyl, nitro, cyano, C1-C4 alkyl, C1-C4 alkoxy and C1-C4 haloalkyl.

2. The resolution method of claim 1, wherein the compound of VI is synthesized by the following step:

reacting a compound of formula IV with an unnatural amino acid of formula V under the action of a nickel salt to form the compound of formula VI,

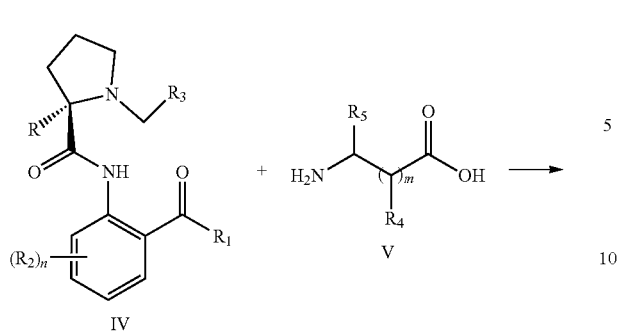
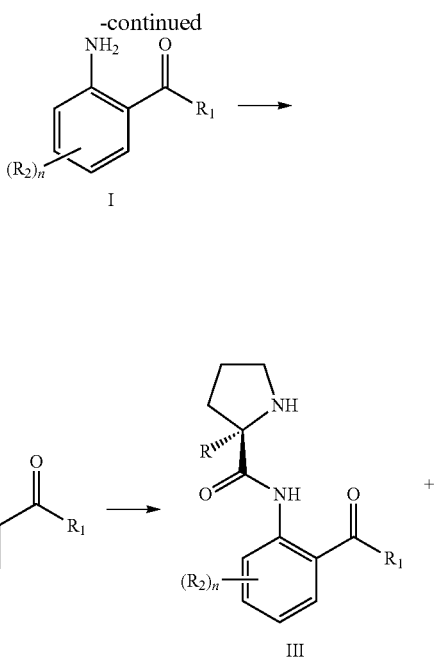

wherein n, m, R, $R_1$, $R_2$, $R_3$, $R_4$ and $R_5$ are as defined in claim 1.

3. A Maraviroc intermediate having a structure of formula VI:

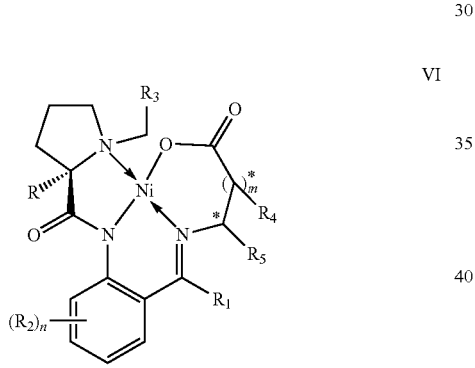

wherein n, m, $R_1$, $R_2$, $R_3$, $R_4$ an $R_5$ areas defined in claim 1.

4. The resolution method of claim 2, wherein the compound of IV is synthesized by the following step:

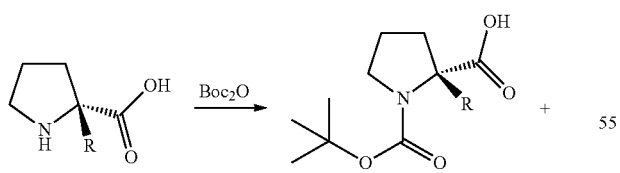

(i) reacting (R)-2-substituted proline with di-tert-butyl dicarbonate to form (R)-1-(tert-butoxycarbonyl)-2-methylproline;

(ii) subjecting (R)-1-(tert-butoxycarbonyl)-2-substituted proline to a condensation reaction with a compound of formula I to obtain a compound of formula II;

(iii) removing tert-butoxycarbonyl from the compound of formula II to obtain a compound of formula III;

(iv) subjecting the compound of formula III to a reductive amination reaction with $R_3CHO$ or $R_3CH_2Cl$ to obtain a compound of formula IV, wherein n, R, $R_1$, $R_2$ and $R_3$ are as defined in claim 1.

* * * * *

UNITED STATES PATENT AND TRADEMARK OFFICE
CERTIFICATE OF CORRECTION

Page 1 of 1

PATENT NO. : 10,875,883 B2
APPLICATION NO. : 16/337338
DATED : December 29, 2020
INVENTOR(S) : Hong Liu et al.

It is certified that error appears in the above-identified patent and that said Letters Patent is hereby corrected as shown below:

In the Claims

Column 92, Lines 44-45, Claim 4: please delete the term "(R)-1-(tert-butoxycarbonyl)-2-methylproline" and insert -- (R)-1-(tert-butoxycarbonyl)-2-substituted proline --

Signed and Sealed this
Eighth Day of June, 2021

Drew Hirshfeld
*Performing the Functions and Duties of the*
*Under Secretary of Commerce for Intellectual Property and*
*Director of the United States Patent and Trademark Office*